(12) United States Patent
Nirenberg

(10) Patent No.: US 9,220,634 B2
(45) Date of Patent: Dec. 29, 2015

(54) RETINA PROSTHESIS

(75) Inventor: Sheila Nirenberg, New York, NY (US)

(73) Assignee: Cornell University, Ithaca, NY (US)

( * ) Notice: Subject to any disclaimer, the term of this patent is extended or adjusted under 35 U.S.C. 154(b) by 418 days.

(21) Appl. No.: 13/595,812

(22) Filed: Aug. 27, 2012

(65) Prior Publication Data

US 2013/0110236 A1   May 2, 2013

Related U.S. Application Data

(63) Continuation-in-part of application No. PCT/US2011/026526, filed on Feb. 28, 2011.

(60) Provisional application No. 61/308,681, filed on Feb. 26, 2010, provisional application No. 61/359,188, filed on Jun. 28, 2010, provisional application No. 61/378,793, filed on Aug. 31, 2010, provisional application No. 61/382,280, filed on Sep. 13, 2010.

(51) Int. Cl.
| | |
|---|---|
| *G06K 9/00* | (2006.01) |
| *A61F 9/08* | (2006.01) |
| *G06N 3/04* | (2006.01) |
| *A61K 35/30* | (2015.01) |
| *A61N 1/05* | (2006.01) |
| *A61N 1/36* | (2006.01) |

(52) U.S. Cl.
CPC ........... *A61F 9/08* (2013.01); *G06N 3/049* (2013.01); *A61N 1/0543* (2013.01); *A61N 1/36046* (2013.01)

(58) Field of Classification Search
USPC .......... 382/100, 103, 106–107, 128–134, 382/154–155, 162, 168, 173, 181, 199, 224, 382/232, 254, 260, 266, 274–276, 286–291, 382/299, 305, 312; 800/18; 607/54, 89, 53, 607/88; 623/11.11
See application file for complete search history.

(56) References Cited

U.S. PATENT DOCUMENTS

| | | | |
|---|---|---|---|
| 5,836,996 | A | 11/1998 | Doorish |
| 5,856,152 | A | 1/1999 | Wilson et al. |

(Continued)

FOREIGN PATENT DOCUMENTS

| | | |
|---|---|---|
| CN | 101239008 A | 8/2008 |
| CN | 101336856 A | 1/2009 |

(Continued)

OTHER PUBLICATIONS

Office Action received in Japanese Patent Application No. 2012-555211 mailed Nov. 5, 2014, 9 pages—with English translation.

(Continued)

*Primary Examiner* — Seyed Azarian
(74) *Attorney, Agent, or Firm* — Foley & Lardner LLP

(57) ABSTRACT

The invention provides a retinal prosthetic method and device that mimics the responses of the retina to a broad range of stimuli, including natural stimuli. Ganglion cell firing patterns are generated in response to a stimulus using a set of encoders, interfaces, and transducers, where each transducer targets a single cell or a small number of cells. The conversion occurs on the same time scale as that carried out by the normal retina. In addition, aspects of the invention may be used with robotic or other mechanical devices, where processing of visual information is required. The encoders may be adjusted over time with aging or the progression of a disease.

17 Claims, 23 Drawing Sheets

(56) References Cited

U.S. PATENT DOCUMENTS

| | | | |
|---|---|---|---|
| 6,400,989 B1* | 6/2002 | Eckmiller | 607/54 |
| 6,458,157 B1 | 10/2002 | Suaning | |
| 6,530,954 B1* | 3/2003 | Eckmiller | 623/11.11 |
| 6,533,798 B2 | 3/2003 | Greenberg et al. | |
| 7,149,586 B2 | 12/2006 | Greenberg et al. | |
| 8,103,352 B2 | 1/2012 | Fried et al. | |
| 8,956,396 B1* | 2/2015 | Friend et al. | 607/89 |
| 2002/0161417 A1 | 10/2002 | Scribner | |
| 2003/0088081 A1 | 5/2003 | Maliga et al. | |
| 2003/0093129 A1 | 5/2003 | Nicolelis et al. | |
| 2003/0105409 A1 | 6/2003 | Donoghue et al. | |
| 2004/0147975 A1 | 7/2004 | Popovic et al. | |
| 2004/0176821 A1 | 9/2004 | Delbeke et al. | |
| 2005/0015120 A1 | 1/2005 | Seibel et al. | |
| 2006/0129207 A1 | 6/2006 | Fried et al. | |
| 2006/0184062 A1 | 8/2006 | Greenberg et al. | |
| 2006/0251621 A1 | 11/2006 | Campochiaro et al. | |
| 2007/0050046 A1 | 3/2007 | Georgopoulos | |
| 2007/0261127 A1* | 11/2007 | Boyden et al. | 800/18 |
| 2008/0021515 A1 | 1/2008 | Horsager et al. | |
| 2008/0021516 A1 | 1/2008 | Greenberg et al. | |
| 2008/0086206 A1 | 4/2008 | Nasiatka et al. | |
| 2008/0221653 A1 | 9/2008 | Agrawal et al. | |
| 2008/0234781 A1 | 9/2008 | Einav et al. | |
| 2008/0249588 A1 | 10/2008 | Greenberg et al. | |
| 2008/0294217 A1 | 11/2008 | Lian et al. | |
| 2009/0088399 A1 | 4/2009 | Balya et al. | |
| 2009/0105786 A1 | 4/2009 | Fetz et al. | |
| 2009/0118793 A1 | 5/2009 | McClure et al. | |
| 2009/0118794 A1 | 5/2009 | McClure et al. | |
| 2009/0326623 A1 | 12/2009 | Greenberg et al. | |
| 2010/0015095 A1 | 1/2010 | Pan et al. | |
| 2010/0016732 A1 | 1/2010 | Wells et al. | |
| 2010/0152849 A1 | 6/2010 | Degenaar et al. | |
| 2010/0234273 A1 | 9/2010 | Boyden et al. | |
| 2010/0262212 A1* | 10/2010 | Shoham et al. | 607/88 |
| 2010/0272688 A1 | 10/2010 | Acland et al. | |
| 2010/0286748 A1 | 11/2010 | Midani et al. | |
| 2011/0213266 A1 | 9/2011 | Williams et al. | |
| 2011/0270352 A1* | 11/2011 | Nanduri et al. | 607/53 |
| 2011/0307079 A1 | 12/2011 | Oweiss et al. | |
| 2012/0123293 A1 | 5/2012 | Shah et al. | |

FOREIGN PATENT DOCUMENTS

| | | |
|---|---|---|
| CN | 101393789 A | 3/2009 |
| EP | 1864690 A2 | 12/2007 |
| EP | 1 891 976 A1 | 2/2008 |
| JP | 2009-540900 | 11/2009 |
| WO | WO-96/13598 | 5/1996 |
| WO | WO-98/48027 | 10/1998 |
| WO | WO-00/15822 | 3/2000 |
| WO | WO-01/94605 A2 | 12/2001 |
| WO | WO-03/047525 A2 | 6/2003 |
| WO | WO-03/080648 A2 | 10/2003 |
| WO | WO-03/093479 A1 | 11/2003 |
| WO | WO-03/104413 A2 | 12/2003 |
| WO | WO-2005/080573 A1 | 9/2005 |
| WO | WO-2007/127428 A2 | 11/2007 |
| WO | WO-2009/126112 | 10/2009 |
| WO | WO-2010/011404 A2 | 1/2010 |
| WO | WO-02/082904 A2 | 10/2012 |

OTHER PUBLICATIONS

Second Office Action received for Chinese Patent Application No. 201180021117.2 mailed Feb. 2, 2015, 9 pages—with English translation.
Ahuja A. et al., "Blind Subjects Implanted With the Argus II Retinal Prosthesis Are Able to Improve Performance in a Spatial-Motor Task," British Journal of Ophthalmology (2010).
Arenkiel et al., "In Vivo Light-Induced Activation of Neural Circuitry in Transgenic Mice Expressing Channelrhodopsin-2," Neuron, 54(2):205-218 (2007).
Asher, et al., "Image Processing for a High-Resolution Optoelectronic Retinal Prosthesis", IEEE Transactions on Biomedical, Engineering, vol. 54, No. 6, Jun. 2007, pp. 993-1004.
Ausubel et al., Current Protocols in Molecular Biology, "Overview of the HIV-1 Lentivivral Vector System", John Wiley & Sons, New York, (1989), Unit 16.21, 15 pgs.
Ausubel et al., Current Protocols in Molecular Biology, "Production of Recombinant Adeno-Associated Viral Vectors for In Vitro and In Vivo Use", John Wiley & Sons, New York, (1989), Unit 16.25, 24 pgs.
Averback et al., Effects of Noise Correlations on Information Encoding and Decoding, J Neurophysiol, vol. 95, 2006, pp. 3633-3644.
Bach et al., "Visual Evoked Potential-Based Acuity Assessment in Normal Vision, Artificially Degraded Vision, and in Patients," British Journal of Ophthalmology, 92:396-403 (2008).
Ballard et al., Computer Vision, Prentice-Hall Inc New Jersey, 1982, (Table-of Contents).
Barnstable et al., "Thy-1 Antigen: A Ganglion Cell Specific Marker in Rodent Retina," Neuroscience, 11(4):847-855 (1984).
Bi A, et al., "Ectopic Expression of a Microbial-Type Rhodopsin Restores Visual Responses in Mice With Photoreceptor Degeneration," Neuron, 50:23-33 (2006).
Bomash I, et al., "A Virtual Retina That Works on a Broad Array of Stimuli Including Natural Scenes: A Tool to Simplify the Problem of Population Coding," Society for Neuroscience, Program No. 891.5 (2010).
Bookstein et al., "Promoter Deletion and Loss of Retinoblastoma Gene Expression in Human Prostate Carcinoma," Proceedings of the National Academy Sciences, USA, 87(19):7762-7766 (1990).
Brown CJ et al., The Relationship Between EAP and EABR Thresholds and Levels Used to PRogram the Nucleus 24 Speech Processor: Data from Adults, Ear and Hearing, vol. 21, No. 2, 2000, pp. 151-163.
Busskamp et al., "Genetic Reactivation of Cone Photoreceptors Restores Visual Responses in Retinitis Pigmentosa," Science, 329:413-417 (2010).
Cai et al., "Gene Delivery to Mitotic and Postmitotic Photoreceptors Via Compacted Dna Nanoparticles Results in Improved Phenotype in a Mouse Model of Retinitis Pigmentosa," The FASEB Journal, 24:1178-1191 (2010).
Campagnola L, et al., "Fiber-Coupled Light-Omitting Diode for Localized Photostimulation of Neurons Expressing Channelrhodopsin-2," Journal of Neuroscience Methods, 169:27-33 (2008).
Cardin et al., "Targeted Optogenetic Stimulation and Recording of Neurons in Vivo Using Cell-Type-Specific Expression of Channelrhodopsin-2," Nature Protocols, 5(2):247-254 (2010).
Cescon C. et al., "Non-invasive characterization of single motor unit electromyographic and mechanomyographic activities in the biceps brachii muscle", J Electromyogr Kinesiol, vol. 16, No. 1, Epub Aug. 19, 2005, pp. 17-24.
Chader GJ, et al., "Artificial Vision: Needs, Functioning, and Testing of a Retinal Electronic Prosthesis", Progress in Brain Research, 175:317-332 (2009).
Chen, C A et al. "HSV amplicon-mediated neurotrophin-3 expression protects murine spiral ganglion neurons from cisplatin-induced damage", Mol Ther., vol. 3., No. 6, pp. 958-963.
Chestek CA et al., "HermesC: Low-Power Wireless Neural Recording System for Freely Moving Primates" IEEE Transactions on Neural Systems and Rehabilitation Engineering, vol. 17, No. 4, 2009, pp. 268-275.
Chiappa, "Evoked Potentials in Clinical Medicine", Third Edition, Lippincott Raven (1997).
Chichilnisky, "A Simple White Noise Analysis of Neuronal Light Responses," Network 12(2):199-213 (2001).
Chopdar A, et al., "Age Related Macular Degeneration,"—Clincial Review—British Medical Journal, 326:485-488 (2003).
Communication pursuant to Rules 161(2) and 162 EPC in EP Appln No. 118223282.5 dated Apr. 12, 2013.
Dann JF, et al., "Retinal Ganglion Cells Projecting to the Accessory Optic System in the Rat," The Journal of Comparative Neurology, 262(1):141-158 (1987).
Dedek et al, "Ganglion Cell Adaptability: Does the Coupling of Horizontal Cells Play a Role?", Public Library of Science (Plos One), 3(3):E1714 (2008).

(56) References Cited

OTHER PUBLICATIONS

Douglas et al., "Independent Visual Threshold Measurements in the Two Eyes of Freely Moving Rats and Mice Using a Virtual-Reality Optokinetic System," Visual Neuroscience, 22(5):677-684 (2005).
Duda RO, et al., Multilayer Neural Networks, Pattern Classification (2nd Edition) Chapter 6, Wiley, NY (2001).
Eckmiller et al., Tunable Retina Encoders for Retina Implants: Why and How; Journal of Nueral Engineering, Institute of Physics Publishing, Bristol, GB, 2(1):s91-s104, Mar. 1, 2005.
Enroth-Cugell et al., "The Contrast Sensitivity of Retinal Ganglion Cells of the Cat," The Journal of Physiology, 187(3):517-552 (1966).
Extended European Search Report and Search Opinion for European Application No. 11748237.2, mailed Jul. 19, 2013.
Famulare M, Fairhall A., "Feature Selection in Simple Neurons: How Coding Depends on Spiking Dynamics," Neural Computation 22(3):581-598 (2010).
Field et al., "Information Processing in the Primate Retina: Circuitry and Coding," Annual Review of Neuroscience, 30:1-30 (2007).
Fitzgerald et al., "Retinal Signal Transmission in Duchenne Muscular Dystrophy," Journal of Clinical Investigation, 93:2425-2430 (1994).
Foley JM, et al., "Contrast Detection and Near-Threshold Discrimination in Human Vision," Vision Research, 21(7):1041-1053 (1981).
Franck KH., "A model of a nucleus 24 cochlear implant fitting protocol based on the electrically evoked whole nerve action potential", Ear & Hearing, vol. 23, No. 18, 2002, pp. 67S-71S.
Freund et al., "A Decision-Theoretic Generalization of On-Line Learning and an Application to Boosting," Journal of Computer and System Sciences, 55:119-139 (1997).
Friedman DS, et al., "Prevalence of Age-Related Macular Degeneration in the United States," Epidemiology, Eye Diseases Prevalence Research Group, Archives of Ophthalmology 122(4):564-572 (Apr. 2004).
Geisler, "Visual Perception and the Statistical Properties of Natural Scenes," Annual Review of Psychology, 59:167-192 (2008).
Gerding H, et al., "Experimental Implantation of Epiretinal Retina Implants (EPI-RET) With an IOL-Type Receiver Unit," Journal Neural Engineering, 4:S38-S49 (2007).
Giolli RA, et al., "The Accessory Optic System: Basic Organization With an Update on Connectivity, Neurochemistry, and Function," Progress in Brain Research, 151:407-440 (2005).
Golan L, et al., "Design and Characteristics of Holographic Neural Photo-Stimulation Systems," Journal of Neural Engineering, 066004, vol. 6, (2009), pp. 1-14.
Graham-Rowe, "A Brighter Future for Retinal Implants," Technology Review, http://www.technologyreview.com/biomedicine/23539/, Boston, MA: MIT (2009).
Greenberg et al., "Differential Targeting of Optical Neuromodulators to Ganglion Cell Soma and Dendrites Allows Dynamic Control of Center-Surround Antagonism," Neuron, 69:713-720 (2011).
Grossman N, et al., "Multi-Site Optical Excitation Using Chr2 and Micro-LED Array," Journal of Neural Engineering, 7(1):1-13 (2010).
Guiraud D. et al., "An implantable neuroprosthesis for standing and walking in paraplegia: 5-year patient follow-up", Journal of Neural Engineering, 2006, vol. 3, pp. 268-275.
Han et al., "Millisecond-Timescale Optical Control of Neural Dynamics in the Nonhuman Primate . Brain," Neuron, 62:191-198 (Apr. 30, 2009).
Hand, "Discrimination and Classification," Wiley Series in Probability and Mathematical Statistics (1981).
Hochberg LR, et al., "Neuronal ensemble control of prosthetic devices by a human with tetraplegia", Nature, Jul. 13, 2006, vol. 442, pp. 164-171.
Huang et al., "An Optoelectronic Platform for Retinal Prosthesis," Biomedical Circuits and Systems Conference (BIOCAS 2006), IEEE, pp. 110-113, Nov. 29, 2006.
Huberman AD, et al., "Architecture and Activity-Mediated Refinement of Axonal Projections From a Mosaic of Genetically Identified Retinal Ganglion Cells," Neuron, 59(3):425-38 (2008).
Huberman AD, et al., "Genetic Identification of an On-Off Direction-Selective Retinal Ganglion Cell Subtype Reveals a Layer-Specific Subcortical Map of Posterior Motion," Neuron, 62(3):327-334 (2009).
International Preliminary Report on Patentability in PCT/US2011/049188 mailed Mar. 14, 2013.
International Search Report and Written Opinion of PCT/US2011/49188 dated Jan. 27, 2012.
International Search Report in PCT/US2011/026526 dated Apr. 22, 2011.
Ivanova E, et al., "Evaluation of the Adeno-Associated Virus Mediated Long-Term Expression of Channelrhodopsin-2 in the Mouse Retina," Molecular Vision, 15:1680-1689 (2009).
Izhikevich, "Dynamical Systems in Neuroscience: The Geometry of Excitability and Bursting," MIT Press, Cambridge, MA (2007).
Izhikevich, "Hybrid Spiking Models," Review, Philosophical Transactions of Royal Society A, 368:5061-5070 (2010).
Jacobs et al., "Ruling Out and Ruling in Neural Codes," Proceedings of the National Academy of Sciences, vol. 106, No. 14:5936-5941 (Apr. 7, 2009).
Kass RE, et al., "Statistical Issues in the Analysis of Neuronal Data," Journal of Neurophysiology, 94(1):8-25 (2005).
Kawasaki et al., "Variability of the Relative Afferent Pupillary Defect," American Journal of Ophthalmology, 120:622-633 (1995).
Kay MA, et al., "Viral Vectors for Gene Therapy: The Art of Turning Infectious Agents Into Vehicles of Therapeutics," Nature Medicine, 7(1):33-40, Review (2001).
Kelly S, et al., "Realization of a 15-Channel, Hermetically-Encased Wireless Subretinal Prosthesis for the Blind," In, pp. 200-203 (2009).
Kibbel S, et al., "Design and Performance Ofan Improved Active Subretinal Chip," World Congress on Medical Physics and Biomedical Engineering, Sep. 7-12, 2009, Munich, Germany (Kim SI, Suh TS, Dassel O, Schlegel WC, Eds), pp. 192-195, Springer Berlin Heidelberg (2009).
Kim RH et al., "Waterproof AIInGaP optoelectronics on stretchable substrates with applications in biomedicine and robotics", Nature Materials, 2010, vol. 9, pp. 929-937.
Koilkonda RD, et al., "Efficient Expression of Self-Complementary AAV in Ganglion Cells of the Ex Vivo Primate Retina," Molecular Vision, 15:2796-2802 (2009).
Kuffler, "Discharge Patterns and Functional Organization of Mammalian Retina," Journal of Neurophysiology, 6(1):37-68 (1953).
Lagali PS, et al., "Light-Activated Channels Targeted to ON Bipolar Cells Restore Visual Function in Retinal Degeneration," Nature Neuroscience, 11 (6):667-675 (Jun. 2008).
Lee et al., "Variability and Correlated Noise in the Discharge of Neurons in Motor and Parietal Areas of the Primate Cortex", The Journal of Neuroscience, Feb. 1, 1998, vol. 18, No. 3, pp. 1161-1170.
Lei L. et al., "Efficient transduction of spiral ganglion cells using adenovirus type 5 vector in the rat", Acta Oto-Laryngologica, 2010, vol. 130, pp. 810-814.
Lesica et al., "Adaptation to Stimulus Contrast and Correlations During Natural Visual Stimulation," Neuron, 55(3):479-491 (Aug. 2, 2007).
Lettvin et al., "What the Frog's Eye Tells the Frog's Brain," Proceedings of the Institute of Radio Engineers 47(11): 1940-1951 (1959); Reprinted from: "The Mind: Biological Approaches to its Functions", Editors: William Corning, et al. 1968, pp. 233-258.
Liao et al., "In Vivo Gene Delivery in the Retina Using Polyethylenimine," Biotechniques, 42 (3):285-288 (2007).
Liu Y. et al., "Promoter effects of adeno-associated viral vector for transgene expression in the cochlea in vivo", Experimental and Molecular Medicine, Apr. 2007, vol. 38, No. 2, pp. 170-175.
Loewenstein JI, et al., "Outer Retinal Degeneration: An Electronic Retinal Prosthesis as a Treatment Strategy," Archives of Ophthalmology, 122 (4):587-596 (2004).
Luebke AE et al., "Adenoviral and AAV-mediated gene transfer to the inner ear: role of serotype, promoter, and viral load on in vivo and in vitro infection efficiencies", Adv. Otorhinolaryngol.Basel, Karger, 2009, vol. 66, pp. 87-98.
Maguire et al., "Safety and Efficacy of Gene Transfer for Leber's Congenital Amaurosis," The New England Journal of Medicine, 358 (21):2240-2248 (May 22, 2008).

(56) References Cited

OTHER PUBLICATIONS

Mancuso et al., "Gene Therapy for Red-Green Colour Blindness in Adult Primates," Nature, 461:784-787 (Oct. 8, 2009).
Martin et al., "Gene Delivery to the Eye Using Adeno-Associated Viral Vectors," Methods, 28:267-275 (2002).
McGowan et al., "Characterization of the Mouse Aldose Reductase Gene and Promoter in a Lens Epithelial Cell Line," Molecular Vision, 4:2 (1998).
Mclaughlin SK, et al., "Adeno-Associated Virus General Transduction Vectors: Analysis of Proviral Structures," Journal of Virology, 62(6):1963-1973 (1988).
Meytlis M, et al., "Assessing the Importance of Correlated Firing Using Large Populations of Neurons," Society for Neuroscience, Program No. 165.3 (2009).
Meytlis, et al. "Determining the role of correlated firing in large populations of neurons using white noise and natural scene stimuli", Vision Research, 2012, vol. 70, pp. 44-53.
Morgans et al., "TRPM1 is Required for the Depolarizing Light Response in Retinal ON-Bipolar Cells," Proceedings of the National Academy Sciences, USA, 106(45):19174-19178 (2009).
Moritz CT et al., "Direct control of paralysed muscles by cortical neurons", Nature, Dec. 2008, vol. 456, vol. 456, pp. 639-643.
Nanduri, et al. "Retinal Prosthesis Phosphene Shape Analysis," 30th Annual International Conference of the IEEE Engineering in Medicine and Biology Society, pp. 1785-1788 (2008).
New Zealand IPO First Examination Report dated Sep. 20, 2013 for New Zealand patent application 608804.
Nirenberg et al., "Heterogeneous Response Dynamics in Retinal Ganglion Cells: The Interplay of Predictive Coding and Adaptation," Journal of Neurophysiology, 103(6):3184-3194 (2010).
Nirenberg et al., "Retinal Ganglion Cells Act Largely as Independent Encoders," Nature 411(6838):698-701 (Jun. 7, 2001).
Nirenberg S, et al, "Targeted Ablation of Diverse Cell Classes in the Nervous System in Vivo," The Journal of Neuroscience, 13(8):3238-3251 (1993).
Nirenberg S, et al., "Population Coding in the Retina," Current Opinion in Neurobiology, 8(4):488-493 (1998).
Nirenberg S, et al., "The Light Response of Retinal Ganglion Cells is Truncated by a Displaced Amacrine Circuit," Neuron, 18:637-650 (1997).
Nirenberg, "Photoablation of Cells Expressing Beta-Galactosidase," Methods in Molecular Biology, 135:475-480 (2000).
Norcia et al., "Measurement of Spatial Contrast Sensitivity With the Swept Contrast VEP," Vision Research, 29(5):627-637 (1989).
Norcia, AM et al. , "Spatial Frequency Sweep VEP: Visual Acuity During the First Year of Life," Vision Research, 25(10):1399-1408 (1985).
Novin et al., "Transforming of Images Information to the Implant Part of Retinal Prothesis, by Converting of Images to Bit Formats," Biomedical Engineering (ICBME), 2010 17th Iranian Conference of IEEE, pp. 1-4, Nov. 3, 2010.
Okuyama et al., "Binocular Infrared Optometer for Measuring Accommodation in Both Eyes Simultaneously in Natural-Viewing Conditions," Applied Optics, 32(22):4147(1993).
Pandarinath et al., "A Novel Mechanism for Switching a Neural System From One State to Another," Frontiers in Computational Neuroscience, 31(4):2 (2010), p. 1-18.
Pandarinath et al., "Symmetry Breakdown in the on and off Pathways of the Retina at Night: Functional Implications," Journal of Neuroscience, 30(30):10006-10014 (Jul. 28, 2010).
Paninski, "Maximum Likelihood Estimation of Cascade Point-Process Neural Encoding Models," Network: Comput. Neural Syst., 15(4):243-262 (2004).
Paninski, et al. "Statistical models for neural encoding, decoding, and optimal stimulus design", Progress in Brain Research, vol. 165, 2007, pp. 493-507.
Panzeri et al., "Correcting for the Sampling Bias Problem in Spike Train Information Measures," Journal of Neurophysiology, 98(3):1064-1072, Review (2007).
Pelli DO, et al., "The Design of a New Letter Chart for Measuring Contrast Sensitivity," Clinical Vision Sciences, 2:187-199 (1988).
Perry VH et al., "Functional lamination in the ganglion cell layer of the macaque's retina", Neuroscience, vol. 25, No. 1, 1988, pp. 217-223.
Petersen-Jones et al., "AAV Retinal Transduction in a Large Animal Model Species: Comparison of a Self-Complementary AAV2/5 With a Single-Stranded AAV2/5 Vector," Molecular Vision, 15:1835-1842 (2009).
Petrs-Silva et al., "High-Efficiency Transduction of the Mouse Retina by Tyrosinemutant AAV Serotype Vectors," Molecular Therapy, 17(3):463-471 (2009).
Pillow, et al. "Spatio-Temporal Correlations and Visual Signalling in a Complete Neuronal Population," Nature 454(7207):995-999 (2008).
Prusky et al., "Rapid Quantification of Adult and Developing Mouse Spatial Vision Using a Virtual Optomotor System," Investigative Ophthalmology & Visual Science, 45(12):4611-4616 (2004).
Pun, Introduction to Optimization Practice, ISBN 471-70233-1 (1969).
Purpura K, et al. "Light Adaptation in the Primate Retina: Analysis of Changes in Gain and Dynamics of Monkey Retinal Ganglion Cells," Visual Neuroscience 4(1):75-93 (1990).
Rolls ET, et al., "Role of Low and High Spatial Frequencies in the Face Selective Responses of Neurons in the Cortex in the Superior Temporal Sulcus in the Monkey," Vision Research, 25(8):1021-1035 (1985).
Rubinstein JT et al., "How do cochlear prostheses work?", Current Opinion in Neurobiology, 1999, vol. 9, 1999, pp. 399-404.
Sauer "Functional Expression of the Ere-Lox Site-Specific Recombination System in the Yeast Saccharomyces Cerevisiae," Molecular and Cellular Biology, 7(6):2087-2096 (1987).
Sellick PM et al., "Modulation of responses of spiral ganglion cells in the guinea pig cochlea by low frequency sound", Hearing Research, 1982, vol. 7, pp. 199-221.
Shapley RM, et al., "How the Contrast Gain Control Modifies the Frequency Responses of Cat Retinal Ganglion Cells," The Journal of Physiology, 318:161-179 (1981).
Sharpee et al., "On the Importance of Static Nonlinearity in Estimating Spatiotemporal Neural Filters With Natural Stimuli," Journal of Neurophysiology 99(5):2496-2509 (2008).
Sheridan, "Gene Therapy Finds Its Niche," Nature Biotechnology, 29(2):121-128 (2011).
Siegert S, et al., Genetic Address Book for Retinal Cell Types, Nature Neuroscience, 12 (9) :1197-1204 (2009).
Simoncelli et al., "Characterization of Neural Responses With Stochastic Stimuli," The Cognitive Neurosciences, 3rd edition, 327-338 (2004).
Simonelli et al., "Gene Therapy for Leber's Congenital Amaurosis Is Safe and Effective Through 1.5 Years After Vector Administration," Molecular Therapy, 18(3):643-650 (2010).
Sinclair, Jr. et al., Selective Ablation of a Class of Amacrine Cells Alters Spatial Processing in the Retina, Journal of Neuroscience, 24(6):1459-1467 (2004).
Sjostrand et al., "Morphometric Study of the Displacement of Retinal Ganglion Cells Subserving Cones Within the Human Fovea," Graefe's Archive Clinical Experimental Ophthalmology 237:1014-1023 (1999).
Soucy et al., "A Novel Signaling Pathway From Rod Photoreceptors to Ganglion Cells in Mammalian Retina", Neuron, 21:481-493 (1998).
Stone et al., "Response Properties of Ganglion Cells in the Isolated Mouse Retina," Visual Neuroscience 10(1):31-39 (1993).
Thyagarajan S, et al., Visual Function in Mice With Photoreceptor Degeneration and Transgenic Expression of Channelrhodopsin 2 in Ganglion Cells, The Journal of Neuroscience, 30 (26) :8745-8758 (2010).
Tomita H, et al., "Channelrhodopsin-2 Gene Transduced Into Retinal Ganglion Cells Restores Functional Vision in Genetically Blind Rats", Experimental Eye Research 90:429-436 (2010).
Troy JB, et al., "Spatial Properties of the Cat X-Cell Receptive Field as a Function of Mean Light Level," Visual Neuroscience, 16(6):1089-1104 (1999).

(56) References Cited

OTHER PUBLICATIONS

Troy JB, et al., "Spatiotemporal Integration of Light by the Cat X-Cell Center Under Photopic and Scotopic Conditions," Visual Neuroscience, 22(4):493-500 (2005).
Turchinovich et al., "Non-Viral Sirna Delivery Into the Mouse Retina In Vivo," Boston Medical Center (BMC) Ophthalmology, 10:25 (2010).
Ueda et al., "The mGluR6 5' Upstream Transgene Sequence Directs a Cell-Specific and Developmentally Regulated Expression in Retinal Rod and ON-Type Cone Bipolar Cells," The Journal of Neuroscience, 17(9):3014-3023 (1997).
van Adel et al., "Delivery of Ciliary Neurotrophic Factor Via Lentiviral-Mediated Transfer Protects Axotomized Retinal Ganglion Cells for an Extended Period of Time," Human Gene Therapy, 14:103-115 (2003).
Victor JD, et al., "The Nonlinear Pathway of Y Ganglion Cells in the Cat Retina", Journal of Genetic Physiology, 74(6):671-689 (1979).
Victor, "The Dynamics of the Cat Retinal X Cell Centre," The Journal of Physiology, 386(1):219-246 (1987).
Volgyi B, et al., "Convergence and Segregation of the Multiple Rod Pathways in Mammalian Retina," The Journal of Neuroscience, 24(49):11182-11192 (2004).
Walther W, et al., Viral Vectors for Gene Transfer: A Review of Their Use in the Treatment of Human Diseases, Drugs, 60(2):249-271, Review (2000).
Wang H. et al., "Efficient cochlear gene transfection in guinea-pigs with adeno-associated viral vectors by partial digestion of round window membrane", Gene Therapy, 2012, vol. 19, pp. 255-263.
Wassle, "Parallel Processing in the Mammalian Retina," National Review of Neuroscience Journal, 5(10):747-757 (2004).
Wells et al., "Optical Stimulation of Neural Tissue In Vivo," Optics Letters 30(5):504-506 (2005).
Winter JO et al., "Retinal Prostheses: Current Challenges and Future Outlook," Journal of Biomaterials Science Polymer Edn, 18(8):1031-1055 (2007).
Wright, "Gene Therapy for the Eye," British Journal of Ophthalmology, 81(8):620-622, Review (1997).
Yonehara K, et al., "Identification of Retinal Ganglion Cells and Their Projections Involved in Central Transmission of Information About Upward and Downward Image Motion," Public Library of Science (Plos ONE), 4(1):E4320 (2009).
Yonehara K, et al., "Expression of SPIG1 Reveals Development of a Retinal Ganglion Cell Subtype Projecting to the Medial Terminal Nucleus in the Mouse," Public Library of Science (Plos ONE), 3(2):E1533 (2008).
Zeng, et al. "Cochlear Damage Changes the Distribution of Vesicular Glutamate Transporters Associated with Auditory and Nonauditory Inputs to the Cochlear Nucleus", The Journal of Neuroscience, Apr. 1, 2009, vol. 29, No. 13, pp. 4210-4217.
Zhang Y, et al., "Ectopic Expression of Multiple Microbial Rhodopsins Restores On and Off Light Responses in Retinas With Photoreceptor Degeneration," The Journal of Neuroscience, 29(29):9186-9196 (2009).
Zierhofer CM et al., "Electronic Design of a Cochlear Implant for Multichannel High-Rate Pulsatile Stimulation Strategies", IEEE, Transactions on Rehabilitation Engineering, Mar. 1995, vol. 3, No. 1, pp. 112-116.
Zou et al., "Extraocular Image Processing for Retinal Prothesis Based on DSP," Nano/Micro Engineered and Molecular Systems (NEMS 2009), 4th IEEE International Conference on IEEE, pp. 563-566, Jan. 5, 2009.
Zrenner et al., "Subretinal Microelectrode Arrays Allow Blind Retinitis Pigmentosa Patients to Recognize Letters and Combine Them to Words," Biomedical Engineering and Informatics (BMEI) '09. 2nd International Conference on Biomedical Engineering and Informatics, ISBN: 978-1-4244-4134-1. pp. 1 013 4 (2009).
Communication (Supplementary EP Search Report) in EP Appln No. 11 82 2382 dated Feb. 17, 2014.
Communication pursuant to Article 94(3) EPC in EP Appln No. 11 748 237.2 dated Apr. 16, 2014.
First Office Action from Chinese Application No. 201180021117.2 dated May 6, 2014.
Douglas, R.M. et al., "Independent visual threshold measurements in the two eyes of freely moving rats and mice using a virtual-reality optokinetic system," Vis Neurosci., (2005), vol. 22, pp. 677-684.
First Examination Report received in Australian Patent Application No. 2011220367 issued Jul. 13, 2015, 5 pages.
Non-Final Office Action received in U.S. Appl. No. 13/230,488 mailed Jul. 2, 2015, 15 pages.
Notice of Allowance received in U.S. Appl. No. 13/821,187 issued Jul. 8, 2015, 23 pages.
Paninski, L. et al., "Statistical models for neural encoding, decoding, and optimal stimulus design," Prog Brain Res. (2007) 165:493-507.
Eckmiller, R. et al., "Dialog Concepts for Learning Retina Encoders," IEEE International Conference on Neural Networks Proceedings, (Jun. 1, 1997), vol. 4, pp. 2315-2320.
Examination Report received in European Patent Application 11748237.2 issued Sep. 3, 2014, 5 pages.
Non-Final Office Action received in U.S. Appl. No. 13/821,187 mailed Jul. 30, 2014, 20 pages.
Examination Report received in European Patent Application No. 11822382.5 mailed Oct. 27, 2014, 6 pages.
Final Office Action received in U.S. Appl. No. 13/230,488 issued Nov. 26, 2014, 24 pages.
First Office Action received in Chinese Patent Application No. 201180051504.0 issued Oct. 10, 2014, first received Nov. 25, 2014, 16 pages with English translation.

\* cited by examiner

RETINA PROSTHESIS

CROSS REFERENCE TO RELATED APPLICATION

This application is a continuation-in-part of International Patent Application No. PCT/US2011/026526 (filed on Feb. 28, 2011) which in turn claims the benefit under 35 U.S.C. §119(e) of U.S. Provisional Application Nos. 61/308,681 (filed on Feb. 26, 2010), 61/359,188 (filed on Jun. 28, 2010), 61/378,793 (filed on Aug. 31, 2010), and 61/382,280 (filed on Sep. 13, 2010).

STATEMENT REGARDING FEDERALLY SPONSORED RESEARCH OR DEVELOPMENT

This invention was made with U.S. Government support under GM0779 awarded by the National Institute of Health (NIH), and under FEY019454A awarded by the National Eye Institute. The U.S. Government has certain rights in the invention.

FIELD OF THE INVENTION

The present invention relates to methods and devices for restoring or improving vision, and for treating blindness or visual impairment. In particular, the present invention relates to methods and devices for restoring or improving vision using a set of encoders that produce normal or near-normal retinal output together with a high resolution transducer targeted to retinal cells.

BACKGROUND OF THE INVENTION

Retinal prosthetics are targeted for patients with retinal degenerative diseases, such as age-related macular degeneration (AMD), and retinitis pigmentosa (RP), which together affect 2 million people in the US (Friedman et al., 2004; Chader et al., 2009) and 25 million worldwide (Chopdar et al., 2003). In both diseases, it is the input side of the retina that degenerates: cones degenerate in AMD and rods in RP.

What the prosthetics aim to do is bypass the degenerated tissue and stimulate the surviving cells, so that visual information can once again reach the brain. The main targets of the prosthetics are the retinal ganglion cells and the retinal bipolar cells (Loewenstein et al., 2004; Gerding et al., 2007; Winter et al., 2007; Lagali et al., 2008; Chader et al., 2009; Zrenner et al., 2009; Thyagarajan et al., 2010).

Currently, the main strategy for retinal prostheses involves the implantation of electrode arrays into the patient's retina in close proximity to either the bipolar cells or ganglion cells (Gerding et al., 2007; Winter et al., 2007; Chader et al., 2009; Zrenner et al., 2009). The patient is then outfitted with a camera/signal-processing device that takes images and converts them into electronic signals; the signals are then passed to the electrodes, which stimulate the cells (reviewed in (Chader et al., 2009)). While the patients can see some light, the performance of the devices is still quite limited: patients are, for example, able to see spots and edges (Nanduri et al., 2008; Chader et al., 2009), which provide some ability for navigation and gross feature detection, but nothing close to normal vision has been possible. (With respect to navigation, patients can detect light sources, such as doorways, windows and lamps. With respect to detecting shapes, patients can discriminate objects or letters if they span ~7 degrees of visual angle (Zrenner et al., 2009); this corresponds to about 20/1400 vision (20/200 is the acuity-definition of legal blindness in most places).

Efforts to improve the electrode-based retinal prosthetics have been directed primarily toward increasing their resolution; the focus has been on decreasing the size of the electrodes and increasing their density in the arrays (Chader et al., 2009), as currently, the electrodes range from 50 and 450 microns in diameter (Kelly et al., 2009; Zrenner et al., 2009; Ahuja et al., 2010), which is 10 to 100 times the size of a retinal cell. While there have been some increases in resolution, the current technology does not achieve the resolution of the normal retina, as it is not yet practical to stimulate individual cells with electrodes, and the technical challenge is severe: finer electrodes require more current, which leads to tissue burning (see, for example, the title and agenda for a recent conference on retinal prosthetics: "The Eye and The Chip 2010: 2010 Special Emphasis on Retinal Stimulation Safety for Neuro-Prosthetic Devices").

As an alternative to stimulating cells with electrodes, optogenetics has been used. The optogenetics approach involves expression of proteins such as channelrhodopsin-2 (ChR2) or one of its derivatives in the ganglion cells or bipolar cells. ChR2 is light sensitive; cells expressing it undergo voltage changes upon light activation, which allows the cells to send electrical signals. (Bi et al., 2006; Lagali et al., 2008; Zhang et al., 2009; Tomita et al., 2010) This approach offers the potential for much higher resolution—cells can, in principle, be stimulated individually. While experiments in animals have demonstrated that the potential for high resolution is real, the achievement of near normal or even partially normal vision does not occur as indicated in several recent papers in the field (Bi et al., 2006; Lagali et al., 2008; Zhang et al., 2009; Thyagarajan et al., 2010; Tomita et al., 2010).

Little attention has been paid by either leading approach to driving the stimulators (either the electrodes or a channelrhodopsin) in a way that closely resembles endogenous signaling from retina to brain. Endogenous retinal signaling is complex. When the normal retina receives an image, it carries out a series of operations on it—that is, it extracts information from it and converts the information into a code the brain can read.

Current electrode-based devices have used much simpler signal processing than the retina, e.g., they just convert light intensity at each point in the image into pulse rate with linear scaling (Loewenstein et al., 2004; Fried et al., 2006; Kibbel et al., 2009; Ahuja et al., 2010). Because of this, the retinal output generated by these devices is very different from normal retinal output; the brain is expecting signals in one code and is getting them in another.

Current optogenetic approaches are similarly limited. Efforts to improve them have focused largely on developing the properties of channelrhodopsin (e.g., increasing its sensitivity to light and altering its kinetics) and have not devoted significant effort to mimicking endogenous retinal signal processing (Bi et al., 2006; Lagali et al., 2008; Zhang et al., 2009; Thyagarajan et al., 2010; Tomita et al., 2010).

Thus, there exists a need to develop a retinal prosthesis that converts visual input into normal retinal output that the brain can readily interpret. The retinal prosthesis also needs to provide high resolution signaling, ideally targeting individual retinal cells such as retinal ganglion cells. The present invention sets forth such a prosthesis; it combines an encoding step that produces normal or near-normal retinal output together with high resolution transducer to provide normal or near normal vision to the blind.

SUMMARY OF THE INVENTION

In one aspect, a method is disclosed comprising: receiving raw image data corresponding to a series of raw images; and processing the raw image data with an encoder to generate encoded data, wherein the encoder is characterized by an input/output transformation that substantially mimics the input/output transformation of one or more retinal cells of a vertebrate retina.

In some embodiments, the encoder is characterized by an input/output transformation that substantially mimics the input/output transformation of one or more retinal cells of a vertebrate retina over a range of input that includes natural scene images, including spatio-temporally varying images.

In some embodiments, processing the raw image data with an encoder to generate encoded data includes: processing the raw image data to generate a plurality of values, X, transforming the plurality of X values into a plurality of response values, lm, indicative of a corresponding response of a retinal cell in the retina, m, and generating the encoded data based on the response values. In some embodiments, the response values correspond to retinal cell firing rates. In some embodiments, the response values correspond to a function of the retinal cell firing rates. In some embodiments, the response values correspond to retinal cell output pulses. In some embodiments, the response values correspond to retinal cell generator potential, i.e., the output of the convolution of the image with the spatiotemporal filter(s).

In some embodiments, processing the raw image data with an encoder to generate encoded data includes: receiving images from the raw image data and, for each image, rescaling the luminance or contrast to generate a rescaled image stream; receiving a set of N rescaled images from the rescaled image stream and applying a spatiotemporal transformation to the set of N images to generate a set of retinal response values, each value in the set corresponding to a respective one of the retinal cells; generating the encoded data based on the retinal response values.

In some embodiments, the response values include retina cell firing rates. In some embodiments N is at least 5, at least about 20, at least about 100 or more, e.g., in the range of 1-1,000 or any subrange thereof.

In some embodiments, applying a spatiotemporal transformation includes: convolving of the N rescaled images with a spatiotemporal kernel to generate one or more spatially-temporally transformed images; and applying a nonlinear function to the spatially-temporally transformed images to generate the set of response values.

In some embodiments, applying a spatiotemporal transformation includes: convolving the N rescaled images with a spatial kernel to generate N spatially transformed images; convolving the N spatially transformed images with a temporal kernel to generate a temporal transformation output; and applying a nonlinear function to the temporal transformation output to generate the set of response values.

In some embodiments, the encoder is characterized by a set of parameters, and where the values of the parameters are determined using response data obtained experimentally from a vertebrate retina while said retina is exposed to white noise and natural scene stimuli.

In some embodiments, the encoder is configured such that the Pearson's correlation coefficient between a test input stimulus and a corresponding stimulus reconstructed from the encoded data that would be generated by the encoder in response to the test input stimulus is at least about 0.35, 0.65, at least about 0.95, or more, e.g., in the range of 0.35-1.0 or any subrange thereof. In some embodiments, the test input stimulus includes a series of natural scenes.

In another aspect, an apparatus is disclosed including: at least one memory storage device configured to store raw image data; at least one processor operably coupled with the memory and programmed to execute one or more of the methods described herein.

In some embodiments, a non-transitory computer-readable medium having computer-executable instructions for implementing the steps of one or more of the methods described herein.

The methods and systems of the present invention provide for restoring or improving vision. Vision is restored or improved using a method that receives a stimulus, transforms the stimulus into a set of codes with a set of encoders, transforms the codes into signals with an interface, which then activate a plurality of retinal cells with a high resolution transducer driven by the signals from the interface. Activation of the plurality of retinal cells results in retinal ganglion cell responses, to a broad range of stimuli, that are substantially similar to the responses of retinal ganglion cells from a normal retina to the same stimuli.

The performance of the methods to restore or improve vision may have the following characteristics: (i) the fraction correct on a forced choice visual discrimination task performed using the codes is at least about 95 percent, 65 percent or 35 percent of the fraction correct on the forced choice visual discrimination task performed using retinal ganglion cell responses from a normal retina; or, (ii) the Pearson's correlation coefficient between a test stimulus and the stimulus reconstructed from the codes when the test stimulus was presented is at least about 0.95, 0.65 or 0.35.

Alternatively, the performance of the methods to restore or improve vision may have the following characteristics: (i) the fraction correct on a forced choice visual discrimination task performed using retinal ganglion cell responses from the activated retina is at least about 95 percent, 65 percent, or 35 percent of the fraction correct on a forced choice visual discrimination task performed using retinal ganglion cell responses from a normal retina; or (ii) the Pearson's correlation coefficient between a test stimulus and the stimulus reconstructed from retinal ganglion cell responses from the activated retina when the test stimulus is presented is at least about 0.95, 0.65 or 0.35.

The encoding step can include the following steps: (i) preprocessing the stimulus into a plurality of values, X; (ii) transforming the plurality of X values into a plurality of firing rates, $\lambda_m$, for a retinal ganglion cell in the retina, m; and, (iii) generating a code representing spikes from said firing rates. The encoding step can include a step for modifying the code with a burst elimination step. The code may be non-transiently stored during the burst elimination step. The burst elimination step can include the steps of: (i) defining the duration of a segment to be examined and a criterion number of pulses for a segment of said duration; (ii) counting pulses in the segment; and, (iii) if the number of pulses exceeds the criterion number, replacing the segment by an alternative in which the time between pulses is approximately maximal.

The encoder can have parameters. The values of these parameters are determined using response data obtained from a retina while said retina is exposed to white noise and natural scene stimuli.

The code can be transformed into output using an interface where the output is a plurality of visible light pulses. The transducer can be a visible light responsive element, such as, for example, a protein. The protein can be Channelrhodopsin-1, Channelrhodopsin-2, LiGluR, ChETA, SFO (step function opsins), OptoXR (light-sensitive GPCR), Volvox Channelrhodopsin-1, Volvox Channelrhodopsin-2, ChIEF, NpHr, eNpHR, or combinations of any of them.

The gene encoding the protein can be introduced into the cell using a viral vector. The viral vector can be recombinant adeno-associated virus. The gene can be expressed selectively in at least one retinal ganglion cell type. In one embodiment, the gene can be selectively expressed using a two vector cre-lox system, where the expression patterns of the two vectors overlap only within the selected cell type. In this embodiment, the two vectors are: (a) a first vector having an inverted gene expressing a light-sensitive protein that is flanked by loxP sites oriented in opposite directions and that is under the regulation of a promoter for a second gene that is expressed at least in the selected cell type; and (b) a second vector comprising a Cre recombinase that is under the regulation of a promoter for a third gene that is expressed at least in the selected cell type and a nonoverlapping set of other cell classes.

The device implementing the method to restore or improve vision can be used to treat a subject with a retinal degenerative disease, such as macular degeneration or retinitis pigmentosa. When treated, the subject is able to achieve at least about 95%, 65% or 35% normal visual acuity as measured with EVA or the ETDRS protocols. Alternatively, when treated, the subject experiences a change of a factor of two or more using the pattern VEP test or Sweep VEP test.

The methods of the invention also provide for a method for activating a plurality of retinal cells involving, receiving a stimulus, transforming the stimulus into a set of codes with a set of encoders, transforming the codes into signals with an interface and activating a plurality of retinal cells with a high resolution transducer driven by the signals from the interface. Activation of the plurality of retinal cells results in responses to a broad range of stimuli, where the stimuli comprise artificial and natural stimuli, and said responses are substantially similar to the responses of normal retinal cells to the same stimuli.

Alternatively, the performance of the method to activate a plurality of retinal cells may exhibit the following characteristics: (i) the fraction correct on a forced choice visual discrimination task performed using the codes is at least about 95 percent, 65 percent, or 35 percent of the fraction correct on a forced choice visual discrimination task performed using retinal ganglion cell responses from a normal retina, or where the Pearson's correlation coefficient between a test stimulus and the stimulus reconstructed from the codes when the test stimulus was presented is at least about 0.95, 0.65 or 0.35.

The methods and systems of the invention also provide for an apparatus for restoring or improving vision in a subject in need thereof, where the apparatus has: (i) a device for receiving a stimulus; (ii) a processing device comprising: (a) non-transient computer readable media storing a set of encoders to generate a set of codes from the stimulus, (b) at least one processor, and (c) non-transient computer readable media storing the codes; (iii) an interface for converting the codes into an output; and, (iv) a high resolution transducer for activating a plurality of retinal cells. The performance of the apparatus for restoring or improving vision is such that activation of the plurality of retinal cells results in retinal ganglion cell responses, to a broad range of stimuli, that are substantially similar to the responses of retinal ganglion cells from a normal retina to the same stimuli. Alternatively, the performance of the apparatus exhibits the following characteristics: (i) the fraction correct on a forced choice visual discrimination task performed using the codes is at least about 95 percent, 65 percent or 35 percent of the fraction correct on a forced choice visual discrimination task performed using retinal ganglion cell responses from a normal retina; or (ii) the Pearson's correlation coefficient between a test stimulus and the stimulus reconstructed from the codes when the test stimulus was presented is at least about 0.95, 0.65 or 0.35. When treated with the apparatus for restoring or improving vision, the subject can achieve at least about 35% normal visual acuity as measured with EVS or the ETDRS protocols. Alternatively, the treated subject experiences a change of a factor of two or more using the pattern VEP test or Sweep VEP test. The apparatus for restoring or improving vision can be used to treat a subject who has a retinal degenerative disease, such as macular degeneration or retinitis pigmentosa.

The methods and systems of the present invention also provide for a non-transitory computer readable medium having computer-executable instructions. The computer-excutable instructions are a set of instructions for converting at least one stimulus into non-transitory codes, where the code is capable of activating a plurality of retinal cells with a high resolution transducer. The performance of the system is such that when measured, the fraction correct on a forced choice visual discrimination task performed using the codes is at least about 35 percent of the fraction correct on a forced choice visual discrimination task performed using retinal ganglion cell responses from a normal retina, or the Pearson's correlation coefficient between a test stimulus and the stimulus reconstructed from the codes when the test stimulus was presented is at least about 0.35. The set of instructions has parameters and the values of these parameters may be determined using response data obtained from a retina while said retina is exposed to white noise and natural scene stimuli.

The methods and systems of the present invention also provide for non-transitory computer-readable medium having computer-executable instruction which has a signal, corresponding to a stimulus, for controlling at least one transducer capable of activating at least one cell in an impaired retina to produce a response which is substantially similar to a response to the stimulus of a corresponding ganglion cell in a normal retina. The signal can be a set of codes, where when measured for performance, the fraction correct on a forced choice visual discrimination task performed using the codes is at least about 35 percent of the fraction correct on a forced choice visual discrimination task performed using retinal ganglion cell responses from a normal retina, or the Pearson's correlation coefficient between a test stimulus and the stimulus reconstructed from the codes when the test stimulus was presented is at least about 0.35.

The methods and systems of the present invention also provide for a method for generating a representation of a stimulus using an encoder for a retina. The methods comprises the following steps: (i) preprocessing the stimulus into a plurality of values, X; (ii) transforming the plurality of X values into a plurality of firing rates, $\lambda_m$; and, (iii) converting the firing rate, $\lambda_m$, to a code. In this case, the performance of the method may be measured as follows: (i) the fraction correct performance on a discrimination task by the output of the encoder is within 35 percent of the fraction correct performance on a discrimination task by a normal retina; (ii) the Pearson's correlation coefficient between the stimulus reconstructed from the output of the encoder and the original stimulus will be at least about 0.35, or where performance of the output of the encoder on an error pattern test is at most about 0.04. The transformation step may involve spatiotemporally transforming the plurality of X values into a plurality of firing rates, $\lambda_m$, where, $\lambda_m$, for each retinal ganglion cell in the retina, m, is a function of $L_m$ which is a linear filter corresponding to the spatiotemporal kernel from a mth retinal ganglion cell, and $N_m$ is a function that describes the mth retinal ganglion cell's nonlinearity. There may be a plurality of encoders $e_m$, where $e_m$ is the encoder for the mth ganglion cell. The code may have a discrete plurality of bits forming a bit stream. Alternatively, the code is a continuous wave.

The stimulus can be electromagnetic radiation. For example, the electromagnetic radiation can be visible light. The code can be transformed using an interface into output which may be a plurality of visible light pulses. Activation of a plurality of cells in a retina with the plurality of visible light pulses can generate at least one first set of spike trains, where at least a fraction of the cells in the retina have at least one transducer which is a visible light responsive element.

The method for generating a representation of a stimulus using an encoder for a retina can further involve driving activation of a plurality of cells in a retina with the plurality of visible light pulses to generate at least one first set of spike trains, where at least a fraction of the cells in the retina have at least one transducer comprising at least one visible light responsive element. The cells can be retinal ganglion cells. The visible light responsive element can be synthetic photoisomerizable azobenzene regulated K+ (SPARK), deopolarizing SPARK (D-SPARK) or combinations of any of the foregoing. The visible light responsive element may be a protein such as, Channelrhodopsin-1, Channelrhodopsin-2, LiGluR, ChETA, SFO (step function opsins), OptoXR (light-sensitive GPCR), Volvox Channelrhodopsin-1, Volvox Channelrhodopsin-2, ChIEF, NpHr, eNpHR or combinations of any of the foregoing. The proteins, genes encoding for them and the viral vectors are all as mentioned previously. The stimulus can vary in a spatio-temporal fashion or may be static. The present invention also provides for a method for determining a set of parameters for an encoder which has the steps of: (a) recording electrical signal data comprising action potential times from retinal ganglion cells of a retina while the retina is exposed to white noise and natural scene stimuli and storing the data; (b) calculating the reverse correlation between the ganglion cell action potential times and the stimulus intensity is calculated, to determine a starting set of values for the linear filter $L_m$; (c) treating $L_m$ as a product of a spatial function and a temporal function wherein the spatial function is parameterized as a grid of weights, and the temporal function is parameterized as the sum of weighted temporal basis functions and $N_m$ is assumed to be an exponential function to ensure there are no local maxima; (d) calculating the likelihood for this set of parameters for the given stimulus and recorded ganglion cell's responses; (e) identifying the initial optimal parameters for the spatial function, temporal function, and exponential nonlinearity by maximizing the likelihood of these parameters; (f) replacing the exponential nonlinearity by a cubic spline; (g) optimizing the parameters of the spline to maximize the likelihood; (h) optimizing the parameters of the spatial and temporal functions to maximize the likelihood while holding the results of step (g) constant; (i) step (g) is repeated while holding results of step (h) constant, and step (h) is repeated; and, (j) step (i) is repeated until the change in likelihood from the two steps is less than an arbitrarily chosen small number. The foregoing method may be embodied in a nontransitory computer-readable medium having computer-executable instructions for determining values for a plurality of parameters which are used for converting at least one first stimulus into a non-transitory code, the parameters for a linear filter, $L_m$, a spatial function and a temporal function, where the parameters are determined by the steps comprising: (a) recording electrical signal data comprising action potential times from retinal ganglion cells of a retina while said retina is exposed to white noise and natural scene stimuli and storing said data; (b) calculating a reverse correlation between retinal ganglion cell action potential times and intensity of each stimulus, to determine a starting set of values for the linear filter $L_m$; (c) establishing a set of parameters for a spatial function; (d) establishing a set of parameters for a temporal function; (e) calculating the likelihood for the set of parameters for the spatial function and the temporal function for a given stimulus and recording responses from the retinal ganglion cell; and, (f) finding optimal sets of parameters for the spatial function, temporal function, and nonlinearity by maximizing the likelihood of the parameters.

DETAILED DESCRIPTION OF THE INVENTION

Figure 1:
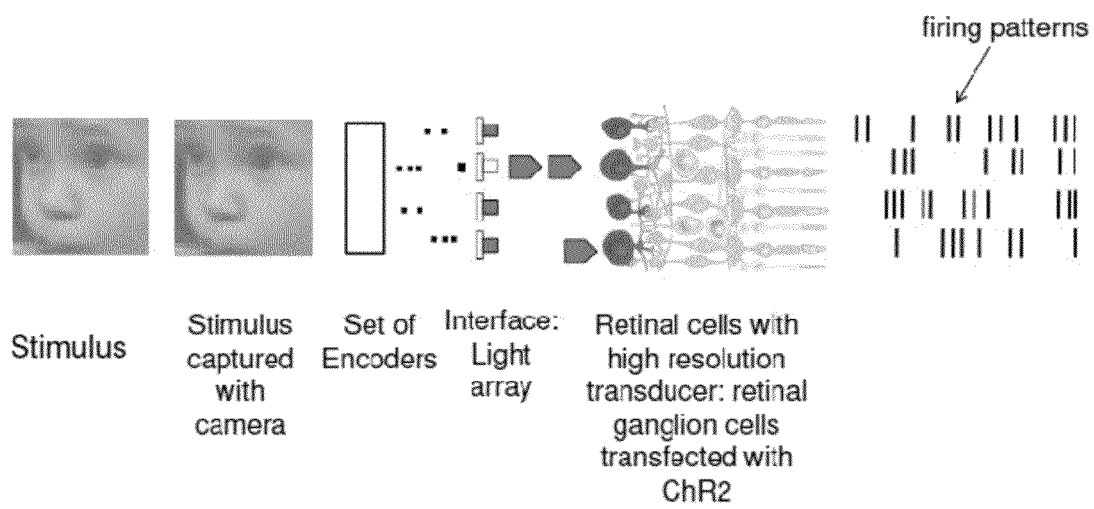
FIG. 1 is a schematic of one embodiment of the prosthetic method. The stimulus is shown on the left, followed by an image—the captured stimulus. The captured stimulus is then processed through a set of encoders, which in turn drive an interface device. The interface device then fires light pulses at retinal ganglion cells that have been transfected with a light-sensitive element, channelrhodopsin-2 (ChR2). The retina produces spike patterns similar to those produced by a healthy retina.

The present invention provides for a method and device for restoring or improving vision, increasing visual acuity, or treating blindness or visual impairment, or activating retinal cells. The method comprises capturing a stimulus, encoding the stimulus, transforming the code into transducer instructions at an interface, and transducing the instructions to retinal cells. The device comprises a way to capture a stimulus, a processing device executing a set of encoders, an interface, and a set of transducers, where each transducer targets a single cell or a small number of cells; the set of transducers is referred to as a high resolution transducer. In one embodiment, each encoder executes a preprocessing step, a spatiotemporal transforming step as well as an output-generating step. The present method can be used for a retinal prosthesis to generate representations for a broad range of stimuli, including artifical and natural stimuli.

The present methods and devices may process any type of stimulus. For example, the stimulus may include visible light, but may also include other types of electromagnetic radiation such as infrared, ultraviolet or other wavelengths across the electromagnetic spectrum. The stimulus may be a single image or a plurality of images; additionally, the images may be static or may vary in a spatiotemporal fashion. Simple shapes such as diagrams or comparatively complex stimuli such as natural scenes may be used. Additionally, the images may be grayscale or in color or combinations of grey and color. In one embodiment, the stimuli may comprise white noise ("WN") and/or natural stimuli ("NS") such as a movie of natural scenes or combinations of both.

The stimulus is converted or transformed into a proxy of normal retinal output, that is, a form of output the brain can readily interpret and make use of as a representation of an image. The conversion occurs on about the same time scale as that carried out by the normal or near-normal retina, i.e., the initial retinal ganglion cell response to a stimulus occurs in a time interval ranging from about 5-300 ms. The methods and devices of the present invention can help restore near-normal to normal vision, or can improve vision, including both grayscale vision and color vision, in a patient or affected mammal with any type of retinal degenerative disease where retinal ganglion cells (which may also be referred to herein as "ganglion cells") remain intact. Nonlimiting examples of retinal degenerative diseases include retinitis pigmentosa, age-related macular degeneration, Usher syndrome, Stargardt macular dystrophy, Leber congenital amaurosis and Bardet-Biedl syndrome, retinal detachment, and retinal vessel occlusion.

Diseases in which retinal degeneration occurs as a complication include: Snowflake vitreoretinal degeneration; Choroidal neovasculatization caused by adult-onset foveomacular dystrophy; Bietti crystalline corneoretinal dystrophy; and diabetic retinopathy. A partial list of diseases in which retinal degeneration occurs as a symptom include: Aceruloplasminemia; Adrenoleukodystrophy; Alstrom disease; Alström Syndrome; Asphyxiating Thoracic Dystrophy; Bonneman-Meinecke-Reich syndrome; Bonnemann-Meinecke-Reich syndrome; CDG syndrome type 1A; Chorioretinopathy dominant form—microcephaly; Choroideremia—hypopituitarism; Congenital disorder of glycosylation type 1A; Congenital Disorders of Glycosylation Type Ia; Cystinosis; Hypotrichosis, syndactyly and retinal degeneration; Jeune syndrome; Mucolipidosis IV; Mucolipidosis type 4; Mucopolysaccharidoses; Muscle-eye-brain syndrome; Neonatal ALD; Olivopontocerebellar atrophy type 3; Osteopetrosis, autosomal recessive 4; Pigmentary retinopathy; Pseudoadrenoleukodystrophy; Retinoschisis, X-linked; Retinoschisis1, X-linked, Juvenile; Santavuori Disease; Spastic paraplegia 15, autosomal recessive; and Werner syndrome The present methods and devices can be used to treat any mammalian subject who has a fraction of retinal ganglion cells, part of the optic nerve originating therefrom as well as some portion of other functional central visual system processing functions remaining intact. Conversely, the range of loss of retinal ganglion cells that is treatable with the methods and devices of the present invention can include only a portion of the total number of retinal ganglion cells or may encompass the total number of retinal ganglion cells present in the retina.

The retina prosthesis, like the normal retina, is an image processor—it extracts essential information from the stimuli it receives, and reformats the information into patterns of action potentials the brain can understand. The patterns of action potentials produced by the normal retinal are in what is referred to as the retina's code or the ganglion cell's code. The retina prosthesis converts visual stimuli into this same code, or a close proxy of it, so that the damaged or degenerated retina can produce normal or near-normal output. Because the retina prosthesis uses the same code as the normal retina or a close proxy of it, the firing patterns of the ganglion cells in the damaged or degenerated retina, that is, their patterns of action potentials are the same, or substantially similar, to those produced by normal ganglion cells. A subject treated with the present devices will have visual recognition ability closely matching the ability of a normal or near-normal subject.

As measured by a variety of different criteria described below, the methods and devices of the present invention reproduce normal or near normal ganglion cell output for a broad range of stimuli, including artifical and natural stimuli. In the retinal prosthetic method, the methods of the invention use an encoding step, an interfacing step, and a transducing step. The methods and devices of the present invention can drive the activation of different retinal cell classes, including, but not limited to, retinal ganglion cells and retinal bipolar cells.

In one embodiment, the prosthesis targets retinal ganglion cells. In this embodiment, the encoding step converts visual stimuli into the code, or a close proxy of the code, used by the ganglion cells, and the transducer, via an interface, drives the ganglion cells to fire as the code specifies. The result is that the damaged or degenerated retina produces normal or near normal output, that is, normal or near normal firing patterns. In another embodiment, the prosthesis targets the retinal bipolar cells (i.e., the transducer is targeted to the retinal bipolar cells, which may also be referred to herein as "bipolar cells"). In this case, the encoding step occurs one stage earlier, that is, the encoding step converts visual stimuli into a code that will drive the bipolar cells to drive the ganglion cells to produce normal output. The use of other codes is also possible. In both cases, the prosthesis comprises a set of encoders and a set of transducers that interact: the encoders drive the transducers. As described below, the encoders drive the transducers via an interface. The result is a method that causes the retinal output cells to produce normal or near normal firing patterns, and deliver normal or near normal visual signals to the brain.

Different encoders may be used, since there are different types of retinal cells. Differences may correspond to a particular cell type or to the cell position on the retina. When a retina prosthesis has more than one encoder, the encoders may operate in parallel, either independently or through at least one or more coupling mechanisms.

Figure 2:
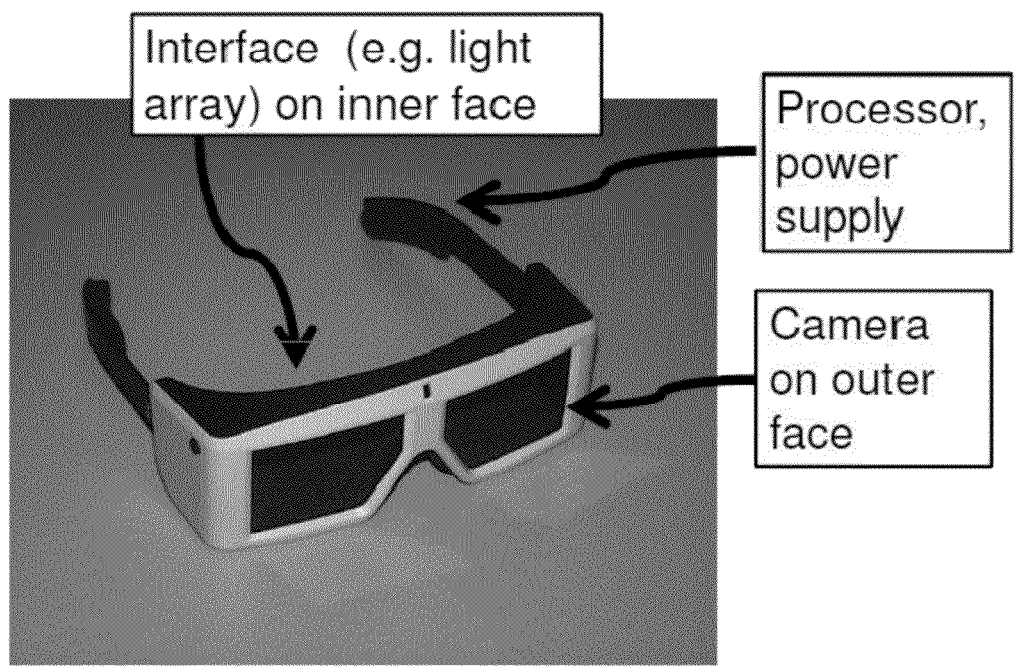
FIG. 2 is a schematic of an embodiment of the device. On the outward face of each lens region in the pair of eyeglasses is a camera; signals from the cameras are directed to the processing device, which, in this embodiment, is located on the arm of the glasses. The processing device controls the light array, which is on the inner face of each lens region.

As mentioned above, in one embodiment, the retinal prosthesis targets the retinal ganglion cells. In this embodiment, the retinal ganglion cells of a subject (e.g., a blind patient) are first engineered via gene therapy to express a transducer, e.g., light-sensitive protein (for example, ChR2). The subject then wears glasses that carry a camera, a processing device executing a set of encoders (one or more), and an interface for generating light pulses. The camera captures images (stimuli), and passes them through the set of encoders. The encoders perform a series of operations on the stimuli and convert them into a coded output, that is, patterns (also referred to as streams) of electrical pulses that correspond to the patterns (or streams) of action potentials the normal ganglion cells would produce to the same stimuli. The streams of electrical pulses are then converted into streams of light pulses to drive the ChR2-expressing cells in the subject's retina. FIG. 1 shows schematically the steps of converting a stimulus (an image) into streams of electrical pulses, which are then converted into streams of light pulses, which then drive the transducers in the retinal cells. FIG. 2 shows an embodiment of the device as it would be provided to patients (the external device that interacts with the transducers operating in vivo.)

Alternatively, instead of the patient receiving gene therapy to provide the transducer, ChR2, electrodes are implanted in the patient's retina in close proximity to the ganglion cells or bipolar cells. In this case, the patient then wears glasses that carry a camera and a processing device executing a set of encoders, and the electrical pulses or bit streams are stored in memory and converted to signals that direct the electrodes to emit electrical pulses that ultimately drive the ganglion cells to fire.

The present methods and devices can be used in a mammal, such as a human. Mammals include, but are not limited to, a rodent (e.g., a guinea pig, a hamster, a rat, a mouse), a primate, a marsupial (e.g., kangaroo, wombat), a monotreme (e.g., duckbilled platypus), murine (e.g., a mouse), a lagomorph (e.g., a rabbit), canine (e.g., a dog), feline (e.g., a cat), equine (e.g., a horse), porcine (e.g., a pig), ovine (e.g., a sheep), bovine (e.g., a cow), simian (e.g., a monkey or ape), a monkey (e.g., marmoset, baboon), an ape (e.g., gorilla, chimpanzee, orangutang, gibbon).

The methods and devices of the present invention may also be used together with robotic or other type of mechanical devices, where processing of visual information or light patterns is required.

The algorithms and/or parameters of the encoders may vary from one patient to another, and may be adjusted over time with aging or the progression of the disease. In addition, a single patient may be equipped with multiple encoders in a single prosthesis where the encoders vary by the spatial position on the retina or other factors, such as cell type, as described herein. The present invention allows ability to conveniently and safely alter the algorithm from outside the body of the patient. Adjustment of the algorithm may be done by one of ordinary skill in the art.

The encoder (or the encoding step) and the transducer (or the transducing step) are described below.

Encoders

An encoder is an input/output model for a cell in the retina (e.g., a ganglion cell or a bipolar cell). It provides the stimulus/response relationship. The encoder operates as an algorithm; the algorithm may be executed by a processing device with dedicated circuitry and/or using computer-readable media, as described herein.

Figure 11:
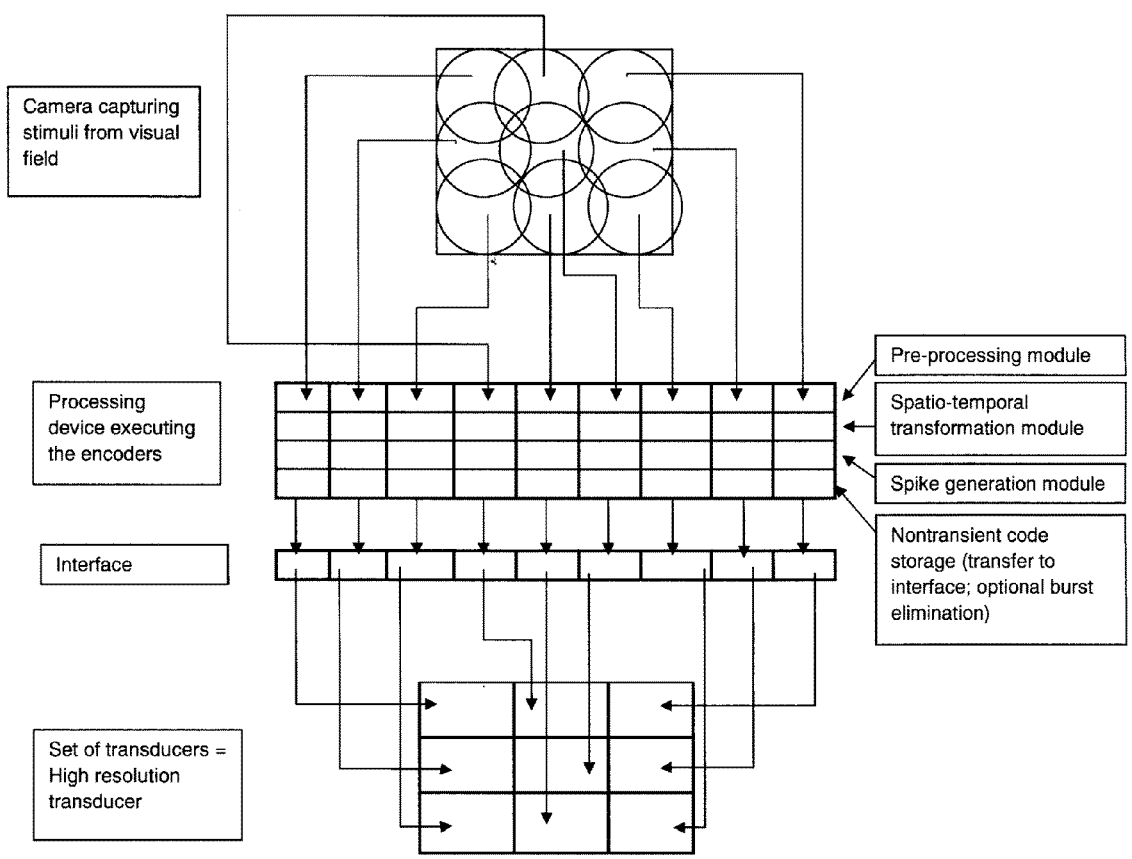
FIG. 11 shows a schematic of the device. A camera (top) captures stimuli from the visual field. The signals from the camera are fed to a processing device that executes the encoders. Execution of the encoders proceeds in a series of steps, indicated in the figure as modules: preprocessing, spatiotemporal transformation, and spike generation. The output of the spike generation step is nontransiently stored in preparation for conversion to a format suitable for the transducers, which includes a burst elimination step. The output is then converted to the format suitable for the transducers in the interface, and the interface then sends its converted signals to the transducers. Arrows show the flow of signals from specific regions of the visual field through the modules of the encoders, through the interface device, to the transducers, which are in the retinal cells. The overlapping circles indicate that the encoders carry information from overlapping regions of the visual field, representing images in a way that is analogous to that of the normal retina.

In one embodiment, the encoders are input/output models for the ganglion cells. These encoders comprise an algorithm that converts stimuli into patterns of electrical signals that are the same, or substantially similar, to those produced by normal ganglion cells to the same stimuli. The retinal prosthetic can use multiple encoders which can be assembled in a parallel manner as shown, for example, in FIG. 11, where different segments of the stimulus (or put another way, different regions of the visual field) are run through separate encoders, which, in turn, control different, specified transducers. In this embodiment, each encoder may have parameters suited for its targeted transducers, which may, for example, take into account the location and/or type of retinal cell or cells being emulated by the encoder or being driven by the encoder's output. The term "code" can refer to a pattern of electrical pulses that corresponds to a pattern of action potentials (also referred to as spike trains) that the retina produces in response to a stimulus. The term "code" may refer to bit streams corresponding to a pattern of spike trains. Each bit may correspond to the activity of one neuron (e.g., 1 means the neuron fires; 0 means the neuron does not fire). The code may also be a continuous wave. Any type of waveform may be encompassed by the present invention, including nonperiodic waveforms and periodic waveforms, including but not limited to, sinusoidal waveforms, square waveforms, triangle waveforms, or sawtooth waveforms.

The general overview of operations performed by one embodiment of the encoder is shown in the flowchart below.

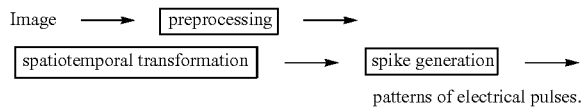

patterns of electrical pulses.

Preprocessing Step

This is a rescaling step, which may be performed in a preprocessor module of the processing device, that maps the real world image, I, into quantities, X, that are in the operating range of the spatiotemporal transformation. Note that I and X are time-varying quantities, that is, I(j,t) represents the intensity of the real image at each location j and time t, and X(j,t) represents the corresponding output of the preprocessing step. The preprocessing step may map as follows: I(j,t) is mapped to X(j,t) by X(j,t)=a+bI(j,t), where a and b are constants chosen to map the range of real world image intensities into the operating range of the spatiotemporal transformation.

The rescaling can also be done using a variable history to determine the quantities a and b, and a user-operated switch can be used to set the values of these quantities under different conditions (e.g., different lighting or different contrast).

For grayscale images, both I(j,t) and X(j,t) have one value for each location j and time t.

For color images, the same strategy is used, but it is applied separately to each color channel, red, green, and blue. In one embodiment, the intensity I(j,t) has three values ($I_1$, $I_2$, $I_3$) for each location j and time t, where the three values $I_1$, $I_2$, $I_3$ represent the red, green, and blue intensities, respectively. Each intensity value is then rescaled into its corresponding X value ($X_1$, $X_2$, $X_3$) by the above transformation.

Spatiotemporal Transformation Step

In one embodiment, the transformation is carried out using a linear-nonlinear cascade (reviewed in Chichilnisky E J 2001; Simoncelli et al 2004), where the firing rate, $\lambda_m$, for each ganglion cell, m, is given by $$\lambda_m(t;X) = N_m((X*L_m)(j,t)) \quad (1)$$

where * denotes spatiotemporal convolution, $L_m$ is a linear filter corresponding to the mth cell's spatiotemporal kernel, and $N_m$ is a function that describes the mth cell's nonlinearity, and, as in the previous section X is the output of the preprocessing step, j is the pixel location, and t is time. The firing rate, $\lambda_m$, is converted into a code that is used to drive the interface (discussed subsequently). This spatiotemporal transformation step may be performed by a spatiotemporal transforming module of the processing device.

$L_m$ is parameterized as a product of a spatial function and a temporal function. For example, in one embodiment, the spatial function consists of a weight at each pixel on a grid (e.g., the digitized image in a camera), but other alternatives, such as a sum of orthogonal basis functions on the grid, can be used. In this embodiment, the grid consists of a 10 by 10 array of pixels, subserving a total of 26 by 26 degrees of visual space (where each pixel is 2.6 by 2.6 degrees in visual space), but other alternatives can be used. For example, because the area of visual space that corresponds to a retinal ganglion cell varies with spatial position on the retina and from species to species, the total array size can vary (e.g., from at or around from 0.1 by 0.1 degree to 30 by 30 degrees, which corresponds to at or around 0.01 by 0.01 degree to 3 by 3 degrees in visual space for each pixel in a 10 by 10 array of pixels.) It is appreciated that the angle ranges and size of the pixel array are only provided for illustration of one particular embodiment and that other ranges of degrees or size of pixel arrays are encompassed by the present invention. For any chosen array size, the number of pixels in the array can also vary, depending on the shape of the area in visual space that the cell represents (e.g., an array of at or around from 1 by 1 to 25 by 25 pixels). Similarly, the temporal function consists of a sum of weights at several time bins and raised cosine functions in logarithmic time at other time bins (Nirenberg et al. 2010; Pillow J W et al. 2008). Other alternatives, such as a sum of orthogonal basis functions, can also be used.

In this embodiment, the time samples span 18 time bins, 67 ms each, for a total duration of 1.2 sec, but other alternatives can be used. For example, because different ganglion cells have different temporal properties, the duration spanned by the bins and the number of bins needed to represent the cell's dynamics can vary (e.g., a duration at or around from 0.5 to 2.0 sec and a number of bins at or around from 5 to 20). Temporal properties can also vary across species, but this variation will be encompassed by the above range.

Eq. 1 can also be modified to include terms that modify the encoder's output depending on its past history (i.e., the spike train already produced by cell m), and on the past history of the output of other ganglion cells (Nirenberg et al. 2010; Pillow J W et al. 2008).

For both sets of parameters for L (spatial and temporal), the choice of resolution (pixel size, bin size) and span (number of pixels, number of time bins) is determined by two factors: the need to obtain a reasonably close proxy for the retina's code, and the need to keep the number of parameters small enough so that they can be determined by a practical optimization procedure (see below). For example, if the number of parameters is too small or the resolution is too low, then the proxy will not be sufficiently accurate. If the number of parameters is too large, then the optimization procedure will suffer from overfitting, and the resulting transformation (Eq. 1) will not generalize. The use of a suitable set of basis functions is a strategy to reduce the number of parameters and hence avoids overfitting, i.e., a "dimensionality reduction" strategy. For example, the temporal function (that covers 18 time bins, 67 ms each) may be parameterized by a sum of 10 weights and basis functions; see section "Example 1, Method of building the encoder" and (Nirenberg et al., 2010; Pillow J W et al. 2008)

The nonlinearities $N_m$ are parameterized as cubic splines, but other parameterizations can be used, such as, piecewise linear functions, higher-order splines, Taylor series and quotients of Taylor series. In one embodiment, the nonlinearities $N_m$ are parameterized as cubic spline functions with 7 knots. The number of knots is chosen so that the shape of the nonlinearity is accurately captured, while overfitting is avoided (see above discussion of overfitting). At least two knots are required to control the endpoints, and thus the number of knots can range from about 2 to at least about 12. Knots are spaced to cover the range of values given by the linear filter output of the models.

For the spatiotemporal transformation step, in addition to the linear-nonlinear (LN) cascade described above, alternative mappings are also within the scope of the present invention. Alternative mappings include, but are not limited to, artificial neural networks and other filter combinations, such as linear-nonlinear-linear (LNL) cascades. Additionally, the spatiotemporal transformation can incorporate feedback from the spike generator stage (see below) to provide history-dependence and include correlations among the neurons as in (Pillow J W et al. 2008; Nichols et al, 2010). For example, this can be implemented by convolving additional filter functions with the output of the spike generator and adding the results of these convolutions to the argument of the nonlinearity in Eq. 1.

Other models may also be used for the spatiotemporal transformation step. Non-limiting examples of the models include the model described in Pillow J W et al. 2008, dynamic gain controls, neural networks, models expressed as solutions of systems of integral, differential, and ordinary algebraic equations approximated in discrete time steps, whose form and coefficients are determined by experimental data, models expressed as the result of a sequence of steps consisting of linear projections (convolution of the input with a spatiotemporal kernel), and nonlinear distortions (transformations of the resulting scalar signal by a parameterized nonlinear function, whose form and coefficients are determined by experimental data, models in which the spatiotemporal kernel is a sum of a small number of terms, each of which is a product of a function of the spatial variables and a function of the spatial variables and a function of the temporal variables, determined by experimental data, models in which these spatial and/or temporal functions are expressed as a linear combination of a set of basic functions, with the size of the set of basis function smaller than the number of spatial or temporal samples, with the weights determined by experimental data, models in which the nonlinear functions are composed of one or segments, each of which is a polynomial, whose cut points and/or coefficients are determined by experimental data, and models that combine the outputs of the above models, possibly recursively, via computational steps such as addition, subtraction, multiplication, division, roots, powers, and transcendental functions (e.g., exponentiation, sines, and cosines).

Spike Generation Step

In the spike generation step, the ganglion cell firing rates are converted into patterns (also referred to as streams) of pulses, equivalent to ganglion cell spike trains. This step may be performed by an output generating module of the processing device.

In one embodiment, for each cell m, an inhomogeneous Poisson process with instantaneous firing rate $\lambda_m$ is created. In one embodiment, time intervals (bins) of length $\Delta t$ are used. For each neuron, the output of the spatiotemporal transformation, $\lambda_m(t;X)$ as given in Eq. 1 above is multiplied by $\Delta t$, yielding a firing probability. A random number chosen from a uniform distribution between 0 and 1 is chosen. If this number is less than the firing probability, a spike at the beginning of this time interval is generated. In one embodiment, $\Delta t$ is 0.67 ms, but other bin widths may be used. This number for $\Delta t$ was chosen in the standard way for generating a Poisson process, that is, the bin width is chosen so that the product of the bin width and the maximum firing rate is a number much less than 1. The choice of bin size is a compromise between computational efficiency and enabling high temporal resolution and wide dynamic range. The choice may be made by one of ordinary skill in the art without undue experimentation. That is, smaller bin sizes increase computational time, while large bin sizes blur resolution of spike patterns.

For the spike generation step, alternative approaches can also be used, including, but not limited to, inhomogeneous gamma processes and integrate-and-fire processes, and Hodgkin-Huxley spike generators (Izhikevich EM 2007; Izhikevich EM 2010)

The output of the encoders—the streams of pulses—are ultimately converted to a format suitable for driving the transducers, for example, electrodes, ChR2 proteins, or other light-sensitive elements. A potential problem is that the output of a given encoder may include pulse sequences where several pulses occur in rapid succession (a "burst" of spikes or spike burst or a burst of pulses or pulse burst). If a particular kind of transducer (for example, ChR2) cannot follow bursts, performance of a prosthesis may be slightly degraded.

The methods of the present invention provide for elimination of this problem, and this method is referred to as the burst elimination step or the correcting or modifying step. If an encoder's output contains a burst sequence, then it is replaced by an alternative in which the occurrence of very short intervals between spikes (or pulses) is minimized. To address this, Poisson variations of the code may be generated. To carry this out in a manner compatible with the real time requirement of the prosthesis, the following operation may be employed: As each brief segment of the spike generator's output is generated (that is, the output of the rescaling, spatiotemporal transformation, and spike generating step) it is inspected. Segments containing a number of pulses greater than or equal to a defined criterion number $N_{seg}$ are replaced by segments in which the number of pulses is made equal to $N_{seg}$ and are approximately equally spaced. In one embodiment with ChR2, segments are of duration $T_{seg}$=33 ms, and the criterion number of pulses for replacement, $N_{seg}$, is 3. $T_{seg}$ may be chosen between at or about 3 ms to 66 ms, and $N_{seg}$ may be chosen between at or about 2 to 20. As an alternative to this procedure, the burst elimination step may delete any pulses that occur within a window $T_{win}$ of a previous pulse, to ensure that no more than a criterion number $N_{win}$ of pulses occur within this window. Here, $T_{win}$ may be chosen in the same manner as $T_{seg}$ above, and $N_{win}$ may be chosen in the same manner as $N_{seg}$ above. The values of $T_{seg}$, $N_{seg}$, $T_{win}$, and $N_{win}$ are selected to accommodate the dynamics of the particular transducer that is being used.

As mentioned above the problem of spike bursts can cause degradation of the performance of the encoder. The problem appears to occur rarely; for example, among the 12,000 1-second long spike trains used to generate the baby face depicted in FIG. 9, the spike correction step was needed for approximately 1% of the pulse sequences.

Note that our encoder can produce spikes with less variability than the normal retina, typically, because of less noise. Thus, the encoder can carry more information about stimuli than real cells do.

Determining the Values of the Parameters for the Spatiotemporal Transformation

As mentioned in the previous section, in one embodiment, the spatiotemporal transformation is carried out via a linear-nonlinear (LN) cascade, as given in Eq. 1. This section describes one method for determining the parameters for $L_m$ and $N_m$ in that equation. First, the normal biological retina is presented with two kinds of stimuli: white noise (WN) and a natural scene movie (NS). To generate the encoders used in the data presented in FIGS. 3-9, 12, 13, and 14 the stimuli were presented for 10 min each, and ganglion cell responses were recorded continuously through both; the data set comprised the responses to both stimuli. The presentation may last at least about 5 min each, at least about 10 min each, at least about 15 min each or at least about 20 min each, although other time intervals may also be used. Determination of the length of measurement time may be done by one of ordinary skill in the art without undue experimentation. The values of the parameters, $L_m$ and $N_m$ are then chosen to maximize the log likelihood of the observed spike trains under the rate function of Eq. 1, where the log likelihood, Z, is given by $$Z = \left\{ \sum_m \left( \sum_i \log[\lambda_m(\tau_m(i); X)] - \int_{t=0}^{end} \lambda_m(t; X) dt \right) \right\}_X \quad (2)$$

where all terms are as defined above, and in addition, $\tau_m(i)$ is the time of the ith spike in the mth cell in response to stimulus X. Note that in Eq. 2, Z depends on $L_m$ and $N_m$ implicitly, because these quantities are involved the calculation of $\lambda_m$ via equation 1. To maximize the log likelihood, the following procedure may be followed. The nonlinearity $N_m$ is first assumed to be exponential, since in this case, the log likelihood, Z, has no local maxima (Paninski et al. 2007). After optimizing the linear filters and the exponential nonlinearity (for example, by coordinate-ascent), the nonlinearity is replaced by a spline. Final model parameters are then determined by alternating stages of maximizing the log likelihood with respect to (i) the spline parameters and (ii) the filter parameters, until a maximum is reached.

This approach can also be used for extensions of Eq 1, which may include history dependence and correlations among ganglion cells as in (Pillow J W et al. 2008; Nichols et al, 2010)

Alternatively, instead of using maximum likelihood, other suitable optimization methods may be used to determine the parameters. Non-limiting examples include, optimization of a cost function, such as, the mean-squared error between the calculated rate function $\lambda_m$ for each stimulus X, and the measured firing rate of the mth cell in response to the stimulus X. Additionally, the parameter estimation procedure can make use of other optimization methods (as alternatives to gradient ascent), such as line search or simplex methods. Other optimization techniques may also be used (see, for example, Pun L 1969).

The use of WN and NS stimuli to find the parameters for the spatiotemporal transformations, or more generally, to find the parameters for the encoders (also referred to as the input/output models for the cells), provides for a unique set of parameters as compared with the use of a single type of stimulus (e.g. either WN or NS alone).

Developing input/output models for retinal ganglion cells, or other retinal cells has been a long-standing difficult problem: models that work well for one kind of stimulus do not work well for others. For example, models optimized for WN stimuli do not perform optimally for NS stimuli and vice versa.

Strategies to address this problem have focused on using biological approaches, whereby the model has a mechanism for adaptation incorporated into it to allow it to adapt to different image statistics. Approaches include quasi-linear models that have components that explicitly adapt (e.g, parameters that depend on the statistics of the input (see, for example, Victor (1987) where the time constant of a filter was made to explicitly depend on input contrast), or nonlinear models in which the adaptation is an emergent property of the nonlinear dynamics (see Famulare and Fairhall (2010). These strategies, however, are not practical to implement in a data-driven way for a broad range of stimuli as needed for this invention: for the quasi-linear model, the number of parameters is too large for the amount of data that can be provided in experimental retinal recordings, potentially precluding its use, and for the nonlinear model, even getting off the ground is difficult, as it's not clear what functional form should be use for the dynamics (e.g., to get it to accurately capture responses to both WN and NS).

As shown in the examples throughout this document, the approach taken here is highly effective, that is, it is able to produce a very reliable mapping of input/output relations for a broad range of stimuli, including artifical and natural stimuli. It is effective in large part because WN and NS are complementary. Specifically, in both the temporal and spatial domains, the NS stimuli are much more heavily weighted towards low frequencies than the WN stimuli (and the WN stimuli are much more heavily weighted towards high frequencies than the NS stimuli). Their complementary nature has a major benefit. The combined stimulus sets sample a diverse space of inputs that drives the optimization to a different location in parameter spaces than would be found by either stimulus set alone. The parameters are not the average of those found using WN and NS alone, but are a distinct set of model parameters that describe the response to both stimulus sets and other stimuli (gratings, etc) as well. The latter is what makes the models generalizable; that is, the latter is what allows the encoders to perform well on a broad range of stimuli (including artificial and natural stimuli), i.e., produce responses that are the same, or substantially similar, to those produced by normal retinal cells when exposed to the same stimuli.

Although we have described and built the encoders in a modular fashion with a specific set of algorithmic steps, it is evident that algorithms or devices with substantially similar input/output relationships can be built with different steps, or in a non-modular fashion, for example, by combining any two or three of the steps in to a single computational unit, such as an artificial neural network.

Given the encoders of the present invention, it is possible to generate data sets, without the collection of physiological data, that can be used, for example, to develop parameters for alternate spatiotemporal transformations, or to train a neural net, to produce identical or similar output using methods that are well known in the art. The explicit description of the encoders thus enables the development of prosthetics, as well as other devices, such as, but not limited to, bionics (e.g., devices providing supranormal capability) and robotics (e.g., artificial vision systems).

For example, such an artificial neural network could use an input layer in which each node receives input from a pixel of the image, followed by one or more hidden layers, whose nodes receive input from the nodes of the input layer and/or from each other, followed by an output layer, whose nodes receive input from the nodes of the hidden layer(s). The output nodes' activity corresponds to the output of the encoder(s). To train such a network, one could use any standard training algorithm, such as back propagation, with the training input consisting of the stimuli we used to build our encoder(s) (i.e., white noise and natural scene movies) and the training output consisting of the output of our encoder(s). This exemplifies that alternative methods could be developed even without collecting further physiological data. (Duda and Hart 2001)

The parameters may be developed using various models of the relationships among the neural cells. Parameters may be developed for neuronal models where the neurons are considered independent, or in which they are coupled or correlated. For the coupled model, terms are added that allow for a spike occurring in one neuron to influence the probability of future spikes in other neurons. (Nichols et al 2010; Pillow J W et al. 2008).

Determining the Signaling Patterns to Drive Bipolar Cells to Drive Ganglion Cells to Produce Normal or Near-Normal Retinal Output.

As shown above, the transducers are targeted for ganglion cells. Here, a transducer that targets bipolar cells is described. In particular, ChR2 is used as an example.

Here, a method for determining the patterns of light stimulation to give to the ChR2-expressing bipolar cells so they produce normal ganglion cell firing patterns is provided. Using the ganglion cell for input/output relations, or the encoders for ganglion cells as described above, the light patterns to drive bipolar cells may be derived through reverse engineering. Briefly, the transformations known, that is, the transformations from image to ganglion cell output, are used to find the light patterns that may be presented to the ChR2-expressing bipolar cells to produce that same ganglion cell output.

The method is as follows. In a multi-electrode recording experiment, arbitrary light patterns are presented to the ChR2-expressing bipolar cells, and ganglion cell responses are recorded; these data are used to determine the transformation between the ChR2-expressing bipolar cells and the ganglion cells. This transformation is then inverted. The inverse transformation goes from any desired ganglion cell output back to the patterns of light to be presented the ChR2-expressing bipolar cells.

To carry this out, the spatiotemporal transformation from bipolar cells to ganglion cells is determined according to the following equation $$\lambda_m(t) = N_m((S*L_m)(t)) \quad (3)$$

where here S is the input to the ChR2-expressing bipolar cells, and L and N are the linear and nonlinear filters for the bipolar to ganglion cell transformation, and λ is the firing rate of the ganglion cell. To obtain the parameters L and N, we drive the ChR2-expressing bipolar cells with light patterns, record ganglion cell responses, and optimize model parameters as described in the section above. With the model parameters in hand, the inputs to ChR2 needed to produce a desired ganglion cell output can be determined. Formally, this involves inverting the transformation expressed by Eq. 3. For example, the following equation may be used:

$$S(t) = \frac{1}{L(0) \cdot \Delta t}\left(N^{-1}(\lambda(t)) - \sum_{a=1}^{A} S(t - a\Delta t)L(a\Delta t)\right)$$

What this equation gives is the next input, S(t), as a function of the desired output λ(t), and the inputs delivered at prior times, S(t−aΔt). The summation over a spans the range of times for which the filter function L is nonzero. This inversion algorithm follows from $$\lambda_m(t) = N_m((S*L_m)(t))$$

by expressing the convolution as a discrete sum and carrying out straightforward algebra.

The above equation represents a formal inversion, and to make it practical, the choice of time step, Δt, and the number of lags, A, can be done empirically, without undue experimentation. Note also that the nonlinearity, N, may not have a unique inverse, but this is not a problem, since, for these purposes, one just needs a solution, not a unique solution— that is, one just needs some pattern to drive the bipolar to produce the correct output, that is, normal or near-normal output. One may, therefore, choose any inverse, as it will work. It is important to note that the ganglion cell encoders serve as the underpinnings for this approach. The knowledge of the of input/output (stimulus/response) relationships of the ganglion cells that are provided by the ganglion cell encoders permit the finding of the light patterns needed to drive the bipolar cells to produce the normal ganglion cell firing patterns, that is, firing patterns that are the same, or substantially similar, to those produced by normal retinal ganglion cells to the same stimuli.

Transducer:

A transducer can receive an input signal and drive a neuron to fire or undergo a voltage change upon receiving this signal. In a preferred embodiment, the transducer targets a single cell and is, for example and without limitation, a light sensitive protein or an electrode targeting one cell. In other embodiments, the transducer targets a small group of cells; a small group of cells may consist of one cell, a group of cells, or approximately 100 cells. In a preferred embodiment, a set of transducers is used and each transducer targets a single cell or a small group of cells as mentioned above. We refer to this set of transducers as a high resolution transducer. More than one transducer may be targeted to a given cell or small group of cells; for example channelrhodopsin-2 and halorhodopsin may be targeted to a single cell.

The transducer may drive any retinal cells to fire or undergo voltage changes, including, but not limited to, retinal ganglion cells and retinal bipolar cells. An interface device may be used to connect the encoder and transducer.

The transducer could use any suitable mechanism, and can include, electrodes, optogenetic stimulators, thermostimulators, photo-thermal stimulators, etc. (Wells et al. 2005) In one embodiment, transducers, such as electrodes, are implanted into the patient's eye in such a way as to stimulate retinal ganglion cells or retinal bipolar cells. In another embodiment, direct photo-activation, such as a photo-absorber based system, is used for the transducer.

Other transducers are within the scope of these teachings, as well as combinations of transducers or multiplexing of transducers. The transducer may be a light-responsive element, including, but not limited to, a protein, for example a light-sensitive protein or a light-responsive chemical entity.

A light-sensitive protein that could serve as a transducer is a light-gated ion channel that is able to generate transmembrane ion transport in response to light. (Zhang et al. 2009; Lagali et al 2008). A light-sensitive protein may be responsive to visible light, ultraviolet light, or infrared light. Examples of light-sensitive proteins include, Channelrhodopsin-1, Channelrhodopsin-2, LiGluR, ChETA, SFO (step function opsins), OptoXR (light-sensitive GPCR), Volvox Channelrhodopsin-1, Volvox Channelrhodopsin-2 (ChR2), ChIEF, NpHr, eNpHR and combinations thereof. A light-sensitive protein or its active fragment may be used as a transducer. (European Patent Application No. 19891976.)

Examples of light-sensitive chemical entities that may be used as transducers include synthetic photoisomerizable azobenzene regulated K+ (SPARK), deoplarizing SPARK (D-SPARK), photoswitchable affinity labels (PALs), CNB-glutamate, MNI-glutamate, BHC-glutamate and combinations thereof.

In one embodiment, the transducer is a light-responsive element in retinal ganglion cells. The code generated by the encoder may be represented by bit streams (e.g., streams of zeros and ones, where zero=no spike, and one=spike). The bit streams are then converted to streams of light pulses (e.g., zero=no light, and one=light). Because the ganglion cells contain a light-responsive element (such as a light-sensitive protein, e.g., ChR2) that converts the light pulses into voltage changes in the membrane, and because ganglion cells are spiking neurons, the light pulses lead to spike production, that is, to action potential production. If the pulsed light is of the appropriate intensity, e.g., in the range of 0.4-32 mW/mm$^2$, the action potentials can follow the light pulses with almost 1-to-1 matching (as shown in Example 13). Thus the ganglion cell firing patterns follow the signals from the encoders very closely.

In another embodiment, the transducer is a light-responsive element in retinal bipolar cells. In this case, the ganglion cells are being driven indirectly: the bipolar cells are stimulated with light, they in turn send signals directly or indirectly (e.g., through amacrine cells) to the ganglion cells, causing them to fire. In this case, the stimulation provided to the bipolar cells may be discrete pulses or continuous waves. The light sensitive element, such as ChR2, when it receives light, causes the bipolar cells to undergo voltage changes and release neurotransmitters to their downstream neurons, and ultimately causing the ganglion cells to fire.

Background firing in some cells may interfere with the light-sensitive protein's (for example, ChR2's) ability to follow the encoder's output. In one embodiment, in order to correct the background firing in a retinal ganglion cell, both ChR2 and halorhodopsin (or their equivalents) could first be expressed in each cell. When activated by yellow light, halorhodopsin will hyperpolarize the cell, suppressing firing. When the cell is meant to fire, the yellow light is turned off and blue light is presented. The blue light activates channelrhodopsin-2 (ChR2), which depolarizes the cell, causing it to fire an action potential. Thus, the cells can be illuminated with yellow light to suppress background firing, and the light can be switched from yellow to blue to produce firing. In another embodiment, the same strategy of bi-directional control can apply to non-spiking cells as well—yellow light would hyperpolarize the cell, and blue light would cause the cells to depolarize.

In addition, as discussed above, the encoder sometimes produces a series of spikes in rapid successions (i.e., bursting), which a transducer, such as ChR2, may not follow well. To address this, Poisson variations of the code may be generated. This version of the code is as meaningful to the brain as the normal code, but are adapted to the kinetics of the transducer. For example, the encoder may be adapted such that the resulting code does not have rapid successions, which is more accommodating to the kinetics of ChR2. Alternatively, variations of ChR2 that follow spikes more tightly may be used. See section on Spike Generation above for the explicit strategy.

Vectors for Use with Light-Sensitive Elements

The gene encoding, for example, a light-sensitive protein, can be introduced into the retinal cells via viral and non-viral vectors and methods. Viral vectors include, but are not limited to, adenoviruses, adeno-associated viruses, retroviruses, lentiviruses, herpes viruses, vaccinia viruses, poxviruses, baculoviruses, and bovine papillomoviruses, and recombinant viruses, such as recombinant adeno-associated virus (AAV), recombinant adenoviruses, recombinant retroviruses, recombinant poxviruses, and other known viruses in the art. (Ausubel et al 1989; Kay et al 2001; and Walther and Stein 2000; Martin et al. 2002; van Adel et al. 2003; Han et al, 2009; U.S. Patent Publication No. 20070261127), Methods for assembly of the recombinant vectors are well-known (see, e.g., Published PCT Application WO2000015822 and other references cited herein).

An adeno-associated virus is one embodiment. Multiple different serotypes have been reported, including, AAV1, AAV2, AAV3, AAV4, AAV5 and AAV6. The AAV sequences employed in generating the vectors, and capsids, and other constructs used in the present invention may be obtained from a variety of sources. For example, the sequences may be provided by AAV type 5, AAV type 2, AAV type 1, AAV type 3, AAV type 4, AAV type 6, or other AAV serotypes or other adenoviruses, including presently identified human AAV types and AAV serotypes yet to be identified. A variety of these viral serotypes and strains are available from the American Type Culture Collection, Manassas, Va., or are available from a variety of academic or commercial sources. Alternatively, it may be desirable to synthesize sequences used in preparing the vectors and viruses of the invention with known techniques; these techniques may utilize AAV sequences which are published and available from a variety of databases. The source of the sequences utilized in preparation of the constructs of the invention, is not a limitation of the present invention. Similarly, the selection of the species and serotype of AAV that provides these sequences is within the skill of the artisan and does not limit the following invention. The AAV may be self-complementary. (Koilkonda et al 2009)

The vector of the invention may be constructed and produced using the materials and methods described herein, as well as those known to those of skill in the art. Such engineering methods used to construct any embodiment of this invention are known to those with skill in molecular biology and include genetic engineering, recombinant virus engineering and production, and synthetic biology techniques. See, e.g., Sambrook et al, and Ausubel et al., cited above; and Published PCT Application WO1996013598. Further, methods suitable for producing a rAAV cassette in an adenoviral capsid have been described in U.S. Pat. Nos. 5,856,152 and 5,871,982. Methods for delivery of genes to the cells of the eye are likewise well known to the art. See, e.g., Koilkonda et al., 2009 and U.S. Patent Publication 20100272688.

The gene may also be delivered through other non-viral methods known in the art, including, but not limited to, plasmids, cosmids and phages, nanoparticles, polymers (e.g., polyethylenimine), electroporation, liposomes, Transit-TKO transfection reagent (Mirus Bio, Madison, USA). Cai et al. 2010; Liao et al. 2007; Turchinovich et al. 2010) A detailed review of possible techniques for transforming genes into desired cells of the eye is taught by Wright. (Wright 1997) It may also be possible to use encapsulated cell technology as developed by Neurotech (Lincoln, R.I., USA).

Regulatory Sequences

The vector may include appropriate expression control sequences including, but not limited to, transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein processing and/or secretion. A large number of different expression control sequences, e.g., native, constitutive, inducible and/or tissue-specific, are well known in the art and may be utilized to drive expression of the gene, depending upon the type of expression desired. The selection of the appropriate expression sequences can be accomplished by one of ordinary skill in the art without undue experimentation.

For eukaryotic cells, expression control sequences typically include a promoter, an enhancer, such as one derived from an immunoglobulin gene, SV40, cytomegalovirus, etc., and a polyadenylation sequence which may include splice donor and acceptor sites. The polyadenylation sequence generally is inserted following the transgene sequences and before the 3' ITR sequence. In one embodiment, the bovine growth hormone polyA is used.

Another regulatory component of the vector useful in the methods of the present invention is an internal ribosome entry site (IRES). An IRES sequence, or other suitable systems may be used to produce more than one polypeptide from a single gene transcript. An IRES (or other suitable sequence) is used to produce a protein that contains more than one polypeptide chain or to express two different proteins from or within the same cell. An example of an IRES is the poliovirus internal ribosome entry sequence, which supports transgene expression in retinal cells.

The selection of the promoter to be employed in the vector may be made from among a wide number of constitutive or inducible promoters that can express the selected transgene in an ocular cell. In one embodiment, the promoter is cell-specific. The term "cell-specific" means that the particular promoter selected for the recombinant vector can direct expression of the selected transgene in a particular ocular cell type. In an embodiment, the promoter is specific for expression of the transgene in retinal ganglion cells. In an embodiment, the promoter is specific for expression of the transgene in bipolar cells.

As discussed above, each class of retinal ganglion cells or retinal bipolar cells uses its own code. In one embodiment of the invention, only one class of ganglion cells is targeted. Expression of the light-sensitive protein may be controlled by a cell-specific promoter. For example, the mGluR6 promoter may be employed to control expression in ON-bipolar cells. (Ueda et al. 1997). For example, the light-sensitive protein may be expressed in retinal ganglion cells via a ganglion cell-specific gene promoter, for example, Thy-1. (Arenkiel et al 2007; Barnstable et al 1984)

In one embodiment, the transducer will be targeted to a specific class of retinal cells using a specific two vector cre-lox system described here (for a description of cre-lox methodology in general, see Sauer (1987). For example, ChR2, may be targeted to a subset of OFF ganglion cells as follows: In one viral vector, the inverted ChR2 gene may be flanked by loxP sites oriented in opposite directions under the regulation of the calretinin promoter; calretinin is expressed in a subset of OFF retinal ganglion cells and in some amacrine cells (Huberman et al, 2008). Then a second viral vector may be introduced that expresses Cre recombinase under the regulation of the Thy-1 (promoter, a promoter expressed in retinal ganglion cells (Barnstable et al 1984). Since the Thy 1 promoter will express the Cre recombinase only in ganglion cells, the inverted ChR2 will only get flipped and expressed in these cells, and not the amacrine cells. The expression of correctly oriented ChR2 will occur only cells where both the calretinin promoter and the Thy 1 promoter are active, that is, the subset of OFF retinal ganglion cells. (Note that both the Thy 1 and calretinin promoters may be active in areas outside of the retina, but they won't cause expression of the genes in the vectors, because the vectors are only applied to the eye, specifically, the retina).

The idea can also be done in reverse (useful depending on the promoters we have): e.g., we can use Thy1 to drive CHR2 in ganglion cells. We put it in the correct orientation and with lox sequences flanking it. We then use another promoter, for example, the GABA A receptor promoter, to activate Cre recombinase in some subset of ganglion cells. The Cre will invert the ChR2 in those cells, shutting it off—so the ChR2 will only be active in cells that express Thy-1 and that do express the other promoter. It does not matter if the Cre is also activated in other classes, because the ChR2 isn't in them, so there's no ChR2 to turn off.

These same approaches apply to other classes of retinal ganglion cells. Their targeting can be achieved using alternate promoters in place of the calretinin promoter, such as the SPIG1-promoter (Yonehara et al 2008, Yonehara et al 2009), the DRD4-promoter (Huberman et al 2009), promoters for neurofilament proteins (Nirenberg and Cepko, 1993), and other promoters that drive expression in subsets of ganglion cells, such as those identified in Siegert et al. (2009). The two vector Cre-Lox system described here readily extends to targeting other classes of cells as well. Promoter analysis can be used to identify promoter functional fragments and derivatives (McGowen at al 1998; 4:2; Bookstein et al. 1990).

In one embodiment, multiple classes of retinal neurons are targeted, and different transducers, such as different ChR2 derivatives, may be expressed in different classes of cells. The different transducers, for example, the different ChR2 derivatives, could differ in their properties including excitation wavelengths. Therefore, the codes may be delivered to specific classes of cells by presenting the codes in different wavelengths. For example, if we put a blue-sensitive transducer only in OFF cells, then we can selectively drive OFF cells by delivering in blue the light pulses produced by the OFF cell code. The other cell classes will not respond to the blue light and thus will not be driven by the OFF cell code.

The architecture of the ganglion cell layer (GCL) of the primate retina also allows for targeting of specific cell types. Ganglion cell bodies lie within the GCL. Near the fovea, the GCL is at its maximal thickness, and contains several layers of cell bodies. The cell bodies of different types of cells lie in different positions within the GCL. For example, ON cell bodies lie closer to the retinal surface (closer to the vitreous) than OFF cell bodies (Perry and Silveira, 1988). Thus they can be preferentially targeted. This can be done, for example, by low-dose infection with a viral vector (e.g., an AAV carrying ChR2); low dose infection will preferentially target cells closer to the surface. This approach is not limited to the fovea, but can apply to any region of the retina where the GCL contains multiple sublayers.

In another embodiment, the light-responsive element may be expressed in bipolar cells. For example, an mGluR6 ChR2 plasmid (Ueda et al. 1997; U.S. Patent Publication 20090088399)) or other high efficiency adeno-associated virus may be used to target the light-responsive element, for example, a gene encoding channelrhodopsin-2, to bipolar cells. (Morgans C W at al 2009; Cardin JA, et al 2010; Petrs-Silva et al. 2009; Petersen-Jones et al. 2009; Mancuso et al. 2009) Bipolar cell-specific promoters may also be used, such as promoters to glutamate receptor genes expressed in ON bipolar cells (see Lagali et al. 2008) or promoters for dystrophin (Fitzgerald et al. 1994). Promoter analysis can be used to identify promoter functional fragments and derivatives (McGowen at al 1998; 4:2; Bookstein et al. 1990)

Examples of constitutive promoters which may be included in the vector of this invention include, without limitation, the CMV immediate early enhancer/chicken β-actin (CβA) promoter-exon 1-intron 1 element, the RSV LTR promoter/enhancer, the SV40 promoter, the CMV promoter, the 381 by CMV immediate early gene enhancer, the dihydrofolate reductase promoter, the phosphoglycerol kinase (PGK) promoter, and the 578 by CBA promoter-exon1-intron1. (Koilkonda et al 2009). Promoter analysis can be used to identify promoter functional fragments and derivatives (McGowen at al 1998; 4:2; Bookstein et al. 1990)

Alternatively, an inducible promoter is employed to express the transgene product, so as to control the amount and timing of the ocular cell's production. Such promoters can be useful if the gene product proves to be toxic to the cell upon excessive accumulation. Inducible promoters include those known in the art and those discussed above including, without limitation, the zinc-inducible sheep metallothionine (MT) promoter; the dexamethasone (Dex)-inducible mouse mammary tumor virus (MMTV) promoter; the T7 promoter; the ecdysone insect promoter; the tetracycline-repressible system; the tetracycline-inducible system; the RU486-inducible system; and the rapamycin-inducible system. Any type of inducible promoter that is tightly regulated may be used. Other types of inducible promoters which may be useful in this context are those which are regulated by a specific physiological state, e.g., temperature, acute phase, a particularly differentiation state of the cell, or in replicating cells only.

Selection of these and other common vector and regulatory elements are conventional and many such sequences are commercially available. See, e.g., Sambrook et al 1989 and Ausubel et al. 1989). Of course, not all vectors and expression control sequences will function equally well to express all of the transgenes of this invention. However, one of skill in the art may make a selection among these expression control sequences without departing from the scope of this invention. Suitable promoter/enhancer sequences may be selected by one of skill in the art using the guidance provided by this application. Such selection is a routine matter and is not a limitation of the molecule or construct. For instance, one may select one or more expression control sequences, operably link the sequence to a transgene of interest, and insert the expression control sequence and the transgene into a vector. The vector may be packaged into an infectious particle or virion following one of the methods for packaging the vector taught in the art.

The vector containing the desired light-sensitive element and cell-specific promoter for use in the target ocular cell as detailed above is preferably assessed for contamination by conventional methods and then formulated into a pharmaceutical composition intended for retinal injection. Such formulation involves the use of a pharmaceutically and/or physiologically acceptable vehicle or carrier, particularly one suitable for intravitreal, retinal, or subretinal injection, such as buffered saline or other buffers, e.g., HEPES, to maintain pH at appropriate physiological levels. A variety of such known carriers are provided in Published PCT Application WO2002082904, incorporated herein by reference. If the virus is to be stored long-term, it may be frozen in the presence of glycerol.

According to the method of this invention for treating an ocular disorder characterized by retinal degeneration, the pharmaceutical composition described above is administered to the subject having such a blinding disease by intravitreal, retinal, or subretinal injection. Methods for the ocular administration of vectors are well known to the art. See, e.g., Koilkonda et al., 2009 and U.S. Patent Publication 20100272688.

An effective amount of a vector carrying a nucleic acid sequence encoding the desired light-sensitive element under the control of the cell-specific promoter sequence may range between about $1 \times 10^9$ to $2 \times 10^{12}$ infectious units in a volume of between about 150 to about 800 microliters. The infectious units are measured as described in McLaughlin et al, 1988. More desirably, an effective amount is between about $1 \times 10^{10}$ to $2 \times 10^{11}$ infectious units in a volume of between about 250 to about 500 microliters. Still other dosages in these ranges may be selected by the attending physician, taking into account the physical state of the subject, preferably human, being treated, the age of the subject, the particular ocular disorder and the degree to which the disorder, if progressive, has developed.

It may also be desirable to administer subsequent dosages of the pharmaceutical compositions of this invention. For example, depending upon the duration of the transgene within the ocular target cell, one may deliver booster dosages at 6 month intervals, or yearly following the first administration.

Such booster dosages and the need therefore can be monitored by the attending physicians, using, for example, the retinal and visual function tests and the visual behavior tests as described herein. Other similar tests may be used to determine the status of the treated subject over time. Selection of the appropriate tests may be made by the attending physician. Still alternatively, the method of this invention may also involve injection of a larger volume of virus-containing solution in a single or multiple injection to allow levels of visual function close to those found in normal retinas.

The code may be converted into light pulses by means of an optical source, such as, but not limited to, an LED array, a DLP Chip, a scanning laser beam or an LCD with appropriate sources. Interfaces for light-sensitive elements are described more fully below.

In another embodiment, the transducers are electrodes. Through the electrodes, the electrical pulses produced by the encoder drive the ganglion cells, either directly or via bipolar cells, or a combination thereof, to fire according to the encoded pulses. The implanted electrode can be, but is not limited to, an electrode such as described in U.S. Pat. Nos. 6,533,798 and 7,149,586; U.S. Patent Publication Nos. 20080249588, 20090326623, and 20080221653.

Examples of vectors using AAV and light sensitive proteins that may be used in this prosthetic, are, but not limited to, sc-mGluR6-hChR2-GFP, mGluR6-hChR2-GFP, sc-smCBA-CHR2-GFP, sc-smCBA-CHR2-GFP, Flex-CBA-Chief-GFP. (Bill Hauswirth, personal communication) A more recent vector using the L7 promoter, which is active in bipolar cells, may also be used, in for example, AAV2 or AAV2-Y444F or AAV2-Y444,500,730F. (See for example Sheridan C 2011; Published PCT applications WO1998048027, WO2001094605, WO2002082904, WO2003047525, WO2003080648, WO2003093479, WO2003104413, WO2005080573, WO2007127428, WO2010011404)

Device:

A prosthetic device to implement the methods described herein comprises the following elements, which may be interconnected physically, wirelessly, optically, or by other means known in the art.

(1) Camera

The camera acquires images with high fidelity. In one embodiment, the camera is based around a charge-coupled device (CCD), such as Point Grey Firefly MV (capable of 752×480 pixels, 8 bits/pixel, at 60 frames per second) (Point Grey Research, Richmond, BC, Canada). Transmitting images from the camera to the processing device in real-time requires a high bandwidth connection. For example, a data transfer of greater than 20 MB/sec can be achieved using a USB 2.0 interface between the camera and processing device.

The camera can be replaced by any device that can capture visual images with high spatial and temporal resolution, and then transfer these images to the processing device. These devices include, but are not limited to, devices based on charge-coupled devices (CCDs); active pixel sensors (APS) such as complimentary metal-oxide-semiconductor (CMOS) sensors, thin-film transistors (TFTs), arrays of photodiodes; and the combinations thereof.

The camera can be interfaced with the processing device using any connection capable of high speed data transfer, including, but not limited to, serial interfaces, such as IEEE 1394 or USB 2.0; parallel interfaces; analog interfaces, such as NTSC or PAL; a wireless interface; the camera could be integrated onto the same board as the processing device.

(2) Processing Device

The processing device implements the encoders which performs the conversion from images to the code in real-time.

The processing device, e.g., hand-held computer, can be implemented using any device capable of receiving a stream of images and transforming them into output in real-time. This includes, but is not limited to, a combination general purpose processor (GPP)/digital signal processor (DSP); a standard personal computer, or a portable computer such as a laptop; a graphical processing unit (GPU); a field-programmable gate array (FPGA) (or a field-programmable analog array (FPAA), if the input signals are analog); an application-specific integrated circuit (ASIC) (if an update is needed, the ASIC chip would need to be replaced); an application-specific standard product (ASSP); a stand-alone DSP; a stand-alone GPP; and the combinations thereof.

In one embodiment, the processing device is a hand-held computer (Beagleboard, Texas Instruments, Dallas, Tex.), based around a dual-core processor that integrates a general purpose processor (GPP) and a digital signal processor (DSP) onto a single chip. This platform is capable of highly-parallel computation and requires much less power than a typical portable computer (~2 Watts or less, compared to 26 Watts for a standard laptop computer). This allows the transformation to be computed in real-time, on a device that is portable and can be powered on a single battery for long periods of time. For example, typical laptop batteries, with charge capacities in the range of 40-60 Watt-hours, could run the processor continuously for about 20-30 hours. In another embodiment, the processing device is small in size so that it can be attached to eye glasses worn by a patient.

For a given location in space, the transformations specified by the encoders are applied to the series of input images, producing encoded output to drive the targeted cell at the desired location in space. In one embodiment, where the targeted cells are retinal ganglion cells, the output of the encoders is a train of electronic pulses that specify the time at which the retinal ganglion cell should fire. The time of each pulse is calculated with sub-millisecond resolution. The majority of the computation takes place on the DSP, while the GPP is used to direct the image data from the camera to the processor's memory, and to synchronize the camera and DSP.

In one embodiment, where the targeted cells are retinal ganglion cells, the output of the processing device is formatted as follows: for a given time t, the output is a matrix of bits where the element at position (x,y) corresponds to the state of ganglion cell at position (x,y): it is 1 if the cell should fire a spike at time t, 0 if the cell should not fire a spike at time t. The dimensions of this matrix are sized such that they match the number of ganglion cells that can be stimulated. The output of the encoders is then stored in memory and converted to signals to drive the transducers via an output interface (see the description under the subheading "(4) Output Interfaces" below). The conversion occurs in blocks. In one embodiment, the output of the encoder is stored for 16.66 ms and then converted as a block. Blocks ranging from 5 ms to 66.66 ms may be used, where the minimum block length in time is determined by the time delay between stimulus onset and ganglion cell first spike.

(3) Transducer

The transducer receives signals from the device, via the output interface, and activates the targeted cells as specified by the encoders. The transducer is detailed above in the section "Transducer."

(4) Output Interfaces

The output interface translates the encoded output (from the processing device) into a form that can drive the transducer. Several output interfaces are possible, depending on the transducer that has been chosen. For example, if the retinal ganglion cell encoders are paired with a light-sensitive transducer (such as ChR2) that is expressed in retinal ganglion cells, the output interface may be a digital light processing (DLP) device. This DLP device would output pulses of light that correspond to the encoded ganglion cell output it receives from the encoder device. The pulses of light would then drive the transducer in the ganglion cells, causing the ganglion cells to fire as the encoder specifies. In this example, the output interface functions as follows: the output of the encoders is sent from the processing unit to the output interface (DLP). The output interface then converts the binary data, which represents action potential times, into light pulses, using a digital micromirror device (DMD) that is paired with a high intensity light emitting diode (LED). The DMD is a grid of mirrors whose position can be switched with high temporal and spatial resolution. When the encoders dictate that the ganglion cell at position (x,y) should fire an action potential, the mirror at position (x,y) on the device is switched to the "on" position for a brief period (e.g., millisecond-timescale), and then switched back to the "off" position. This reflects light from the LED onto the retina for a brief period, causing a light pulse at position (x,y). This light pulse drives the retinal ganglion cell at position (x,y) to fire.

In one embodiment, the device is paired with the light-sensitive transducer ChR2, expressed in retinal ganglion cells, and the output interface is a digital light processing (DLP) device as described above (TI DLP Pico Projector Development Kit v2.0, Texas Instruments, Dallas, Tex.). The standard light source on the DLP device may be replaced with a high intensity LED, intense enough to activate ChR2 (Cree XP-E Blue LED, Cree, Durham N.C.). As mentioned above, the DLP contains a digital micromirror device (DMD) (DLP1700A, Texas Instruments, Dallas, Tex.), which consists of a grid of mirrors, each of which can be switched to reflect the light from the LED onto the retina when the retinal ganglion cell at that location should fire. Data is sent from the encoding device to the output interface over a High Definition Multimedia Interface (HDMI, 22 MB/sec). The position of each mirror on the DMD is controlled with high temporal resolution—when an encoder dictates that a ganglion cell should fire an action potential, the mirror at the corresponding location is switched to the "on" position for a brief time period (1.4 ms). The mirror switching states causes the device to output a pulse of light to the corresponding location, which drives the targeted retinal ganglion cell to fire an action potential. The mirror switching time may be shorter or longer, for example from 0.1 ms to 10 ms, depending on the amount of light required to activate the cell. In this embodiment, the array of mirrors on the DMD is 480 by 320 mirrors, and is thus capable of targeting over 150,000 locations (e.g., cells) independently. The DLP could also have more mirrors, e.g. 1024 by 768 mirrors, as in the case of the DLP5500A (Texas Instruments, Dallas, Tex.), and thus could stimulate many more locations independently. Data transfer between the encoding device and the interface follows standard specifications, as laid out in Texas Instruments Application Report DLPA021—January 2010—"Using the DLP Pico 2.0 Kit for Structured Light Applications".

The DLP is one example of a potential output interface. The output interface could also be implemented using any device capable of activating the transducer it is paired with. For light-activated transducers, this includes, but is not limited to, Digital micromirror devices; LED arrays; Spatial light modulators; Fiber optics; Lasers; Xenon lamps; Scanning mirrors; Liquid-crystal displays (LCDs), and the combinations thereof. (Golan L, et al 2009; Grossman N et al., 2010)

For transducers based on electrodes, the output interface could consist of any device capable of driving current into the electrodes, which are known in the art.

(5) One or more or any part thereof of the techniques described herein, including the encoder (which may include preprocessing, spatiotemporal transformation, spike generation, and burst elimination steps) and optimization of parameters for the encoder, can be implemented in computer hardware or software, or a combination of both. The methods can be implemented in computer programs using standard programming techniques following the method and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The analysis, preprocessing, and other methods described herein can also be implemented as a computer-readable storage medium, configured with a computer program, where the storage medium so configured causes a computer to operate in a specific and predefined manner to perform the functions described herein. In some embodiments, the computer readable media is tangible and substantially non-transitory in nature, e.g., such that the recorded information is recorded in a form other than solely as a propagating signal.

In some embodiments, a program product may include a signal bearing medium. The signal bearing medium may include one or more instructions that, when executed by, for example, a processor, may provide the functionality described above. In some implementations, signal bearing medium may encompass a computer-readable medium, such as, but not limited to, a hard disk drive, a Compact Disc (CD), a Digital Video Disk (DVD), a digital tape, memory, etc. In some implementations, the signal bearing medium may encompass a recordable medium, such as, but not limited to, memory, read/write (R/W) CDs, R/W DVDs, etc. In some implementations, signal bearing medium may encompass a communications medium such as, but not limited to, a digital and/or an analog communication medium (e.g., a fiber optic cable, a waveguide, a wired communications link, a wireless communication link, etc.). Thus, for example, the program product may be conveyed by an RF signal bearing medium, where the signal bearing medium is conveyed by a wireless communications medium (e.g., a wireless communications medium conforming to the IEEE 802.11 standard).

It is to be understood that any of the signals and signal processing techniques may be optical or digital or analog in nature, or combinations thereof.

As mentioned above, the output of the encoders is stored in blocks for conversion to signals to drive the transducers (via the output interface). For example, in one embodiment, where the output interface produces light pulses using a DLP, the output of the encoders is translated into signals to control the states of the mirrors in the DLP (either reflect toward the retina or reflect away from the retina). The conversions are performed in blocks. In one embodiment, the output of the encoders is stored for 16.66 ms and converted as a block. Blocks ranging from 5 ms to 66.66 ms may be used, where the minimum block length in time is chosen to correspond to the minimum time delay between stimulus onset and ganglion cell first response (in normal WT retinas). An additional advantage of the block storage is that it allows for the burst elimination step described in the section entitled, "Spike Generation Step" under the section entitled, "Encoders" to be performed.

Methods to Measure Performance of the Encoder and the Prosthetic

The following describes the procedure for measuring the performance of the encoder and the prosthetic. Performance can be measured in at least three different ways: by performance on a forced choice visual discrimination task, or accuracy on a Bayesian stimulus reconstruction test, or performance on an error pattern test. The term "test stimulus" that will be used herein, refers to a stimulus or a stimuli, which is presented to an animal for evaluation of performance of the encoders or encoders+transducers (i.e., the retinal prosthetic). The term "stimulus reconstructed" that will be used herein, refers to a reconstruction of the stimulus using methods described herein. The term "activated retina" refers to a retina treated with encoders+transducers; this includes transducers targeted to ganglion cells or bipolar cells.

It is important that the task used to measure prosthetic performance falls into a range of difficulty that allows meaningful information to be obtained, as the task used in Example 8 shows. Briefly, the task must be difficult enough (i.e. must use a stimulus set rich enough) that the normal retinal responses provide information about the stimuli, but do not perform perfectly on the task. For example, in the task shown in the example, the fraction correct using the responses from the normal retina, was 80%, satisfying this criterion. If the task used is too hard, such that the normal retina's performance is near chance, then matching is of limited use to a performance analysis. Conversely, if the task chosen is too easy (e.g., requiring just gross discriminations, such as black versus white, and where the fraction correct for the responses from the normal retina is near 100%), then prosthetic methods that are far from approximating the retina's natural code and provide nothing close to normal vision could appear to do well. Thus, it is critical to use an appropriately challenging test, as was used in the accompanying examples. The use of a challenging test also allows one to determine if the prosthesis is performing better than the retina (i.e., entering into the domain of "bionic vision").

To evaluate performance on a forced choice visual discrimination task, a known test in the art, a confusion matrix is used (Hand DJ. 1981). A confusion matrix shows the probability that a response to a presented stimulus will be decoded as that stimulus. The vertical axis of the matrix gives the presented stimulus (i), and the horizontal axis gives the decoded stimulus (j). The matrix element at position (i,j) gives the probability that stimulus i is decoded as stimulus j. If j=i, the stimulus is decoded correctly, otherwise, the stimulus is decoded incorrectly. Put simply, elements on the diagonal indicate correct decoding; elements off the diagonal indicate confusion.

In this task, an array of stimuli is presented, specifically, stimuli containing natural scenes (see below for requirement for stimuli for this task), and the extent to which the stimuli can be distinguished from each other, based on the responses of the ganglion cells and/or encoders, is measured. For the data generated in FIG. 8, which is used to set the criterion for performance on the discrimination task described here, the responses of the ganglion cells were recorded with a multielectrode array as in Pandarinath et al, 2010, and the stimuli were presented on a computer monitor.

A training set is obtained in order to build response distributions (the "training set"), and another set is obtained to be decoded to calculate the confusion matrix (the "test set").

To decode the responses in the test set, one determines which of the stimuli $s_j$ was the most likely to produce it. That is, one determines the stimulus $s_j$ for which $p(r|s_j)$ was maximal. Bayes theorem is used, which states that $p(s_j|r)=p(r|s_j)p(s_j)/p(r)$, where $p(s_j|r)$ is the probability that the stimulus $s_j$ was present, given a particular response r; $p(r|s_j)$ is the probability of obtaining a particular response r given the stimulus $s_j$; and $p(s_j)$ is the probability that the stimulus $s_j$ was present. $p(s_j)$ is set equal for all stimuli in this experiment and so, by Bayes Theorem, $p(s|r_j)$ is maximized when $p(r|s_j)$ is maximized. When $p(s_j)$ is uniform, as it is here, this method of finding the most likely stimulus given a response is referred to as maximum likelihood decoding (Kass et al. 2005; Pandarinath et al. 2010; Jacobs et al. 2009). For each presentation of stimulus $s_i$ that resulted in a response r that was decoded as the stimulus $s_j$, the entry at position (i,j) in the confusion matrix is incremented.

To build the response distributions needed for the decoding calculations used to make the confusion matrices (i.e., to specify $p(r|s_j)$ for any response r), the procedure is as follows. The response r was taken to be the spike train spanning 1.33 sec after stimulus onset and binned with 66.7 ms bins, as in the examples in this document where confusion matrices were generated. The spike generation process is assumed to be an inhomogeneous Poisson process, and the probability $p(r|s_j)$ for the entire 1.33 s response is calculated as the product of the probabilities for each 66.7 ms bin. The probability assigned to each bin is determined by Poisson statistics, based on the average training set response in this bin to the stimulus $s_j$. Specifically, if the number of spikes of the response r in this bin is n, and the average number of spikes in the training set responses in this bin is h, then the probability assigned to this bin is $(h^n/n!)\exp(-h)$. The product of these probabilities, one for each bin, specifies the response distributions for the decoding calculations used to make the confusion matrices.

Once the confusion matrices are calculated, overall performance in the forced choice visual discrimination task is quantified by "fraction correct", which is the fraction of times over the whole task that the decoded responses correctly identified the stimuli. The fraction correct is the mean of the diagonal of the confusion matrix.

Given this procedure, 4 sets of analyses are performed. For each one, the responses from the WT retina are used for the training set and a different set of responses is used for the test set, as outlined below:

(1) The first set should consist of responses from the WT retina. This is done to obtain the fraction correct produced by normal ganglion cell responses.

(2) The second set should consist of the responses from the encoders (the responses from the encoders, as indicated throughout this document, are streams of electrical pulses, in this case, spanning 1.33 sec after stimulus presentation, and binned with 66.7 ms, as are the WT ganglion cell responses). Responses from this test set yield a measure of how well the encoders perform, given the response distributions of the normal WT retina. The basis for this is that the brain is built to interpret the responses of the normal WT retina (i.e., the naturally encoded responses.) When responses from the encoder are used as a test set, one obtains a measure of how well the brain would do with our proxy of the normal retinal responses (our proxy of the retina's code).

(3) The third set should consist of responses from a retina of a blind animal driven by the encoders+transducers (ChR2), where the responses are of the same duration and bin size as above. This set provides a measure of how well the encoder performs after its output has been passed through the transducer in real tissue.

(4) Finally, the last set consists of the responses from a retina of a blind animal driven by just the transducer (ChR2), with responses of the same duration and bin size as above. This gives us a measure of how well the standard optogenetic method performs. This is essentially a control experiment to show that the discrimination task provides an adequate test, as explained in the paragraph above concerning appropriate difficulty of the test.

As shown in Example 8, the encoder's performance in the forced choice visual discrimination task was 98.75% of the normal retina's performance, the complete system's performance, that is, the performance of the current embodiment of the encoder+transducer, was 80% of the normal retina's performance, and the performance of the standard method (just transducer alone) was less than 10% of the normal retina's performance (8.75%). Thus, when tested in vitro or in an animal model, the performance of the prosthesis in the forced choice visual discrimination task, as measured by "fraction correct", will be at least about 35%, 50%, 60%, 70%, 80%, 90%, 95%, 99%, or 100% of the performance of the normal retina, or better than the normal retina, measured as described above. Note that 35% is about 4 times better than the performance of the optogenetic approach in Example 8. Likewise, the performance of the encoder by itself, because it can be used in conjunction with other transducers or for other purposes, such as but not limited to robot vision, will be at least about 35%, 50%, 60%, 70%, 80%, 90%, 95%, 99%, or 100% of the performance of the normal retina, or better than the normal retina, measured as described above.

The performance of the encoder may also be measured using stimulus reconstruction. Stimulus reconstruction uses a standard maximum likelihood approach to determine the most likely stimulus presented given a set of spike trains (reviewed in Paninski, Pillow, and Lewi, 2007). While the brain does not reconstruct stimuli, reconstructions serve as a convenient way to compare methods and give an approximation of the level of visual restoration possible with each approach.

Figure 9:
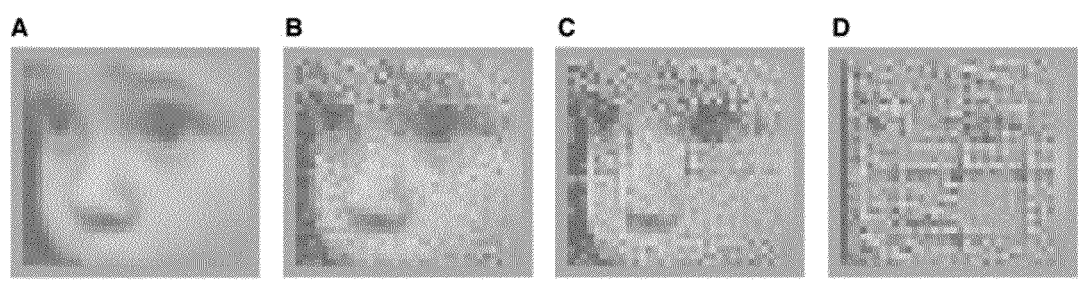
FIG. 9 shows that an image reconstructed from the responses of the retinal prosthesis closely matches the original image while an image reconstructed from the responses of the standard optogenetic method does not. While the brain does not necessarily reconstruct images, reconstructions serve as a convenient way to compare methods and give an approximation of the level of visual restoration possible with each approach. A. Original image. B. Image reconstructed from the responses of the encoders. C. Image reconstructed from the responses of the encoders+transducers (ChR2). D. Image reconstructed from the responses of the standard optogenetic approach (just ChR2, as in above figures). Note that panel B is the critical panel, as it shows the output of the encoders, which could be teamed up with different kinds of transducers. The reconstructions were carried out on our processing cluster in blocks of 10×10 or 7×7 checks. As mentioned in the text, we used maximum likelihood, that is, for each block, we found the array of gray values that maximized the probability of the observed responses (for high dimensional searches, following Paninski et al. 2007).

The stimulus should be a uniform gray screen for 1 second, followed by a given image for 1 second, preferably a human face. Each pixel of the stimulus must span a reasonable region of visual space, so that features of the image, in this case a face can be discerned. This criterion is satisfied by a choice of 35 by 35 pixels per face, as shown in FIG. 9. This is consistent with the fact that facial recognition makes use of spatial frequencies at least as high as 8 cycles per face, which requires at least 32 pixels in each dimension for adequate sampling (Rolls et al, 1985). In the example shown in FIG. 9, which uses mouse, each pixel corresponded to 2.6 degrees by 2.6 degrees of visual space. This in turn corresponds to approximately 12-20 ganglion cells on the mouse retina.

Reconstructing the stimulus consists of a search over the space of all possible stimuli to find the most likely stimulus given the measured population response r. To find the most likely stimulus given r, Bayes' theorem, $p(s|r)=p(r|s)*p(s)/p(r)$ used. Because the a priori stimulus probability $p(s)$ is assumed to be constant for all s, maximizing $p(s|r)$ is equivalent to maximizing $p(r|s)$.

To determine $p(r|s)$, it is assumed that the cells' responses are conditionally independent that is, it is assumed that $p(r|s)$ is the product of the probabilities $p(r_j|s)$, where $p(r_j|s)$ is the probability that the jth cell's response is $r_j$, given the stimulus s. The rationale for this assumption is that it has been shown that deviations from conditional independence are small, and contribute only a small amount to the information carried (Nirenberg et al, 2001; Jacobs et al, 2009) and to the fidelity of stimulus decoding.

To calculate $p(r_m|s)$ for a given cell m, the response $r_m$ is taken to be the spike train of the mth cell spanning 1 sec after stimulus onset and binned with 0.67 ms bins. Since the spike generation process is assumed to be an inhomogeneous Poisson process, the probability $p(r_m|s)$ for the entire 1 sec response is calculated as the product of the probabilities assigned to each bin. The probability assigned to each bin is determined by Poisson statistics based on the cell's expected firing rate in this bin to the stimulus s. The cell's expected firing rate is calculated from Eq. 1 (see section "The Encoders," under "Spatiotemporal Transformation Step"), as the quantity $\lambda_m(t;X)$, where X in eq. 1 is taken to be the stimulus s, and t is the time of the bin. Finally, the probability of the response for the population of cells, p(r|s), is calculated by multiplying the probabilities of the responses of the individual cells $p(r_j|s)$.

To find the most likely stimulus $s_j$ for the population response, r, standard gradient ascent techniques are used. The goal is to find the stimulus $s_j$ that maximizes the probability distribution p(r|s). Since the stimulus space is high-dimensional, the gradient ascent method is used as it provides an efficient way to search through this high-dimensional space. The procedure is as follows. The search starts at a random point in stimulus space, $s_k$. The probability distribution $p(r|s_k)$ for this stimulus is evaluated, and the slope of this probability distribution with respect to each dimension of the stimulus is calculated. A new stimulus $s_{k+1}$, is then created by changing the stimulus $s_k$ in the direction of increasing probability (as determined from the slope of the probability distribution). This process is continued iteratively until the probability of the stimulus starts to increase by only a marginal amount, i.e., until the peak of p(r|s) is reached. Note that because the probability distribution is not strictly log-concave, there exists the possibility of getting stuck in local maxima. To verify that this is not occurring, reconstructions using multiple random starting points must be performed to confirm that they converge to the same peak.

To compare the performance of the prosthetic methods, reconstructions must be performed from 3 sets of responses: 1) responses from the encoders, 2) responses from a blind retina, where the ganglion cells are driven by the encoders+transducers (ChR2), and 3) responses from a blind retina, where the ganglion cells were driven by just the transducers (i.e., just ChR2). The reconstructions should be carried out on processing clusters in blocks of 10×10 or 7×7 pixels, so as to make comparisons to the results in the Examples (FIG. 9 specifically).

To obtain a large enough dataset for the complete reconstruction, it may be necessary to move the image systematically across the region of retina one is recording from, so that responses to all parts of the image can be obtained with a single or small number of retinas. Approximately 12,000 ganglion cell responses were recorded for each image in FIG. 9. The performance should be the same or substantially similar to that shown in FIG. 9B. Not only is it possible to tell that the image is a baby's face, but one can also tell that it is this particular baby's face, a particularly challenging task.

To quantify the differences in the performance of the methods, each method's reconstruction must be compared with the original image. This is done by calculating the standard Pearson correlation coefficient between the reconstructed image's values at each pixel, and that of the real image. With this measure, a correlation coefficient of 1 indicates that all of the original image's information was perfectly retained, while a correlation coefficient of 0 indicates that the resemblance of the reconstruction to the real image was no greater than chance.

As shown in FIG. 9, the results were as follows: for the encoders alone, the correlation coefficient was 0.897; for the encoders plus transducers, the correlation coefficient was 0.762, and for the transducers alone (corresponding to the current art), the correlation coefficient was 0.159. Thus, just as we found for the discrimination task, the performance of the encoders+transducers was several-fold better than the performance of the current art.

Thus, when tested in vitro or in an animal model, the performance of the prosthesis, as measured by reconstruction accuracy may be as follows: The Pearson's correlation coefficient between the reconstruction from the responses of the encoders+transducers (the retinal prosthetic) and the original image will be at least about 0.35, 0.50, 0.60, 0.70, 0.80, 0.90, 0.95, or 1.0. Likewise, the Pearson's correlation coefficient between the reconstruction from the encoder's responses and the original image, will be at least about 0.35, 0.50, 0.60, 0.70, 0.80, 0.90, 0.95, or 1.0, or will perform better than the normal retina, measured as described above. Note that 0.35 is >2 times better than the performance of the optogenetic method in Example 8.

An additional test that can be performed on the confusion matrix data is a test that focuses on the pattern of errors, the "Error Pattern Test," which is measured using a standard measure in the art, the mean squared error (MSE). To test the effectiveness of the encoders and the encoders+transducers (i.e., the prosthetic method), the error pattern is evaluated for sets (2), (3), and (4) above, since this quantity is calculated with reference to the set (1). The extent to which the error pattern for each set ((2), (3), or (4)) matches that of the WT (i.e., the normal) (set (1)) is quantified by the mean-squared error (MSE), which is defined as the average of the square of the difference between the elements of the confusion matrix determined for one of the test sets ((2), (3), or (4)), and the WT (set (1)). The rationale for this test is that the pattern of decoding errors indicate which stimuli are likely to be confused by the brain when it receives the retinal output, i.e., which stimuli cannot be distinguished from each other. As can be seen in Example 8, the normal (WT) retina has a range of performance—there are some stimuli that can be readily distinguished by the responses of the real cells, and some that cannot. For example, as shown in the top right confusion matrix of FIG. 8 in Example 8, the responses of the population of WT ganglion cells are clearly able to distinguish 10 of the 15 stimuli presented (indicated by the 10 bright squares along the diagonal of the matrix); in contrast, the responses of the population of WT ganglion cells show confusion for the remaining 5 stimuli (as indicated by the presence of off-diagonal squares). The Error Pattern Test provides a way to quantify the extent to which the responses of the encoders, the encoders+transducers, and the transducers alone, distinguish or confuse the same stimuli. It measures the extent to which the confusion matrices for sets (2), (3), and (4) match that of set (1); specifically, it calculates the average of the square of the difference between the elements of the test confusion matrices (sets (2), (3), and (4)) and the WT (set (1)). To develop a retinal prosthetic that provides normal or near-normal vision, it is necessary that the neural signals being sent to the brain (i.e., the ganglion cell firing patterns) provide the same information that normal cells provide, that is, that stimuli that are normally distinguished are distinguished, and stimuli that are normally perceived as similar remain that way (are perceived as such when the prosthetic is used).

When the data from Example 8 was used to measure the error pattern, the results were the following: the encoder's performance yielded an MSE of 0.005; that is, the match to the error pattern of the normal retina was very close. The complete system's performance (encoders+transducers) yielded an MSE of 0.013, also very close. The transducer alone yielded an MSE of 0.083, a much higher value, indicating that the match to the normal error pattern was poor. Thus, when tested in vitro or in an animal model, the match to the error pattern of the real retina, as measured by MSE, may be at most about 0.04, 0.03, 0.02, 0.01, or 0.005. Note that 0.04 indicates a match that is at least twice as good (since 0.04 is less than half of 0.083) as the optogenetic approach in Example 8, and the encoder+transducer yields a match of 0.013, substantially better than that.

In order to test a prosthetic using the methods described herein, mammalian retinas with transducers applied to the same retinal cell classes are obtained, as are wild type retinas of the same species. The tests described above are then executed. For all the analyses above, the results should be consistent across retinas of the same type, for example at least about five retinas.

Measures of Clinical Utility

Visual Acuity.

The World Health Organization (WHO) defines low vision as best corrected distant visual acuity in the better eye less than 20/60 but 20/400 or better, or widest diameter of the visual field subtending an angle of less than 20 degrees but greater than 10 degrees, and blindness as best corrected distant visual acuity in the better eye of less than 20/400 or less or widest diameter of the visual field subtending an angle of less than 10 degrees. In the United States, legal blindness is defined as best corrected distant visual acuity of 20/200 or less in the better eye or widest diameter of visual field subtending less than 20 degrees. Most North American states require best corrected visual acuity with both eyes of 20/40 for an unrestricted driving license. (Riordan-Eva 2010)

Since the early 1980's the standard measure of visual acuity for clinical trials has been the Early Treatment of Diabetic Retinopathy Study (ETDRS) chart, which has five letters on each row and spacing between letters and rows equal to the letter size, with a geometric progression of letter sizes. (Kniestedt and Stamper, 2003; (Ferris F L et al 1982; ETDRS report number 7). An electronic equivalent test has been developed and validated and is now widely used, known as the electronic visual acuity test ("EVA") (Beck R W et al 2003; Cotter S A, et al 2003).

Protocols for testing visual acuity are known in the art. A standard protocol using ETDRS chart is as follows.

A. Visual Acuity Chart: Modified Bailey-Lovie

The ETDRS visual acuity charts 1 and 2 are used for standardized measurement of visual acuity. Acuity testing of all subjects, regardless of visual acuity, begins at four meters. Two ETDRS Visual Acuity Charts are used for the measurement of visual acuity, each with a different letter sequence. The right eye will always be tested with Chart 1 and the left eye with Chart 2.

B. Illumination of Visual Acuity Charts and Room

Each clinic must have/use an ETDRS light box for the ETDRS visual acuity charts during any study acuity testing if the EVA is non-functional. The light box should be hung on the wall or placed on a stand (that can be purchased from the Lighthouse for the Blind in New York) at a height such that the top of the 3rd row of letters (0.8 Log MAR) is 49+2 inches (124.5+5.1 cm) from the floor. Room lighting should be approximately 50 foot-candles and should be uniform between the subject and the light box. The distance from the center of the exam chair to the Visual Acuity Chart should be 4.0 meters.

C. Best-Corrected Visual Acuity Measurements

The right eye is tested first and then the left eye. The subject is seated such that the distance from the center of the exam chair to the ETDRS Visual Acuity Chart is 4.0 meters. This testing distance is always used first even if the subject could not be refracted at four meters. In addition to the occluder in the trial frame, the left eye is occluded with an eye patch or pad placed beneath the trial frames. With the lens correction obtained by subjective refraction in the trial frame, the subject is asked to read ETDRS Visual Acuity Chart 1 from the top with the right eye. It is emphasized to the subject that each answer will be scored so adequate time should be allowed for each letter in order to achieve the best identification. The subject is instructed that all of the figures to be read are letters and that there are no numbers.

The examiner records each letter identified correctly by the subject as he/she reads the chart by circling the corresponding letter on the ETDRS score sheet (or study form). Letters read incorrectly, or for which no guesses are made, are not marked on this form. Each letter read correctly is scored as one point. The score for each line (including zero if no letters were read correctly on that line) and the total score for the eye are recorded on the form, as soon as the four meter testing has been completed.

If the number of letters read correctly at four meters is less than twenty, the test should be repeated at one meter and both the four-meter and one-meter totals should be recorded on the ETDRS score sheet (or study form). Both eyes should be tested at four meters before the subject is moved up to the one-meter test distance. It is strongly advised that the total number of letters correctly read at four meters be calculated as soon as the four meter testing has been concluded in order to identify subjects who require 1 meter testing. Prior to actual testing at one-meter, +0.75 D sphere should be added to the correction already in the trial frame to compensate for the new distance. The subject must sit for testing at the one-meter distance.

The same procedure for obtaining visual acuity for the right eye is used for the left eye, except that ETDRS Visual Acuity Chart 2 is used. Chart 1 should never be exposed to the left eye and chart 2 should never be exposed to the right eye, even when switching charts and occlusion.

Poor Vision Testing (Testing for Light Perception)

If the subject cannot identify any letters on visual acuity testing of an eye (i.e., letter score=0), the eye is tested for light perception with the indirect ophthalmoscope as the light source. The testing procedure can be performed according to the investigator's usual routine. The following procedure is indicated:

Room lighting should remain at the level of normal visual acuity testing. The trial frame should be removed, and the subject should close the opposite eye and occlude it by making a tight seal with the palm around the orbit and the bridge of the nose. The indirect ophthalmoscope light should be in focus at three feet, and the rheostat set at six volts. From a distance of three feet the beam should be directed in and out of the eye at least four times; the subject should be asked to respond when he/she sees the light. If the examiner is convinced that the subject perceives the light, vision should be recorded as light perception, otherwise as no light perception.

Calculating the Visual Acuity Score

After each measurement of visual acuity, the visual acuity score for the visit is calculated. The visual acuity score is defined by the number of letters read correctly, as follows:

If twenty or more letters are read correctly at the four-meter test distance, the visual acuity score is equal to the number of letters (N) read correctly at four meters+30. If one or more but less than twenty letters are read correctly at four-meter distance, the visual acuity score is equal to the number of letters read correctly at four meters plus the number of letters read correctly at one meter in the first six lines.

If no letters are read correctly at either the four-meter distance or the one-meter distance, the visual acuity score is 0, and testing for light perception should be performed as described below.

Visual acuity using the ETDRS chart is scored as follows, separately for each eye, with testing at 4 meters:

| Line | Acuity | Letters correct |
| --- | --- | --- |
| 1 (top) | 20/200 | |
| 2 | 20/160 | |
| 3 | 20/125 | |
| 4 | 20/100 | |
| 5 | 20/80 | |
| 6 | 20/63 | |
| 7 | 20/50 | |
| 8 | 20/40 | |
| 9 | 20/32 | |
| 10 | 20/25 | |
| 11 | 20/20 | |
| 12 | 20/16 | |
| 13 | 20/12.5 | |
| 14 | 20/10 | |
| | total letters | |

If the total number correct is 20 or more, the score is the total number correct plus 30. If the total number correct is less than 20 than the patient is tested on same chart at 1 meter and the score is recorded.

| Line | Acuity | Letters correct |
| --- | --- | --- |
| 1 (top) | 20/800 | |
| 2 | 20/640 | |
| 3 | 20/500 | |
| 4 | 20/400 | |
| 5 | 20/320 | |
| 6 | 20/250 | |
| | total correct | |

The visual acuity letter score is then equal to the total number of letters read correctly at 4.0 meters, plus the total number of letters read correctly at 1.0 meter in the first six lines.

The measures of visual acuity, (e.g. "20/20") may also be expressed as percentages of normal visual acuity if 20/20 is taken as normal vision, as per the following table:

| VISUAL ACUITY | PERCENTAGE OF EFFICIENCY |
| --- | --- |
| 20/20 | 100% |
| 20/25 | 96% |
| 20/30 | 91% |
| 20/35 | 87% |
| 20/40 | 84% |
| 20/45 | 80% |
| 20/50 | 76% |
| 20/60 | 70% |
| 20/70 | 64% |
| 20/80 | 58% |
| 20/90 | 53% |
| 20/100 | 49% |
| 20/110 | 45% |
| 20/120 | 41% |
| 20/140 | 34% |
| 20/160 | 29% |
| 20/200 | 20% |
| 20/240 | 13% |
| 20/320 | 7% |
| 20/400 | 5% |
| 20/480 | 2% |
| 20/800 | 1% |
| <20/800 | 0% |

Effectiveness of treatment may therefore be expressed as increased in the number of letters read, which is easily translated to the number of lines gained in the EVA test or on the ETDRS chart, or effectiveness can be expressed as achieving a given percentage of normal vision.

For example, treatment with the device will increase visual acuity at least by 15 letters, on the ETDRS chart or EVA test. 15 letters represents 3 lines on they ETDRS chart. If a patient presents with low vision of 20/100, treatment with the method will improve the patient's vision to 20/50 vision, which is 76% of normal vision, or near-normal vision.

Treatment with the device will increase visual acuity at least by 18 letters, at least by 21 letters, at least by 24 letters, at least by 27 letters, at least by 30 letters, at least by 33 letters on the ETDRS chart or EVA test, depending on where the patient starts and efficacy of the particular course of treatment.

Based on in vitro results described above and in the examples with regard to the performance on a forced choice visual discrimination task, accuracy on a Bayesian stimulus reconstruction test, and performance on an error pattern test, and on the in vivo results described in the examples, treatment with the inventive method will improve vision to 34%, 41%, 45%, 49%, 53%, 58%, 64%, 70%, 76%, 80%, 84%, 87%, 91%, 96%, and 100% of normal visual acuity.

Objective electrophysiological tests in humans may consist of any of the following:

One test is the flash visual evoked response (VEP), where an improvement consists of a change from an absent response to a present response. The appearance of a response is an objective indicator that visual signals reach the brain (Chiappa 1997). This test provides a coarse measure of visual function; it indicates that signals have reached the brain. It does not provide information about resolution.

Based on in vitro results described above and in the examples with regard to the performance on a forced choice visual discrimination task, accuracy on a Bayesian stimulus reconstruction test, and performance on an error pattern test, and on the in vivo results described in the examples, treatment with the device will provide a positive result on the flash visual evoked response.

A second test, one that addresses pattern signals, is the pattern VEP, either elicited by transient or steady-state stimuli, where an improvement consists of (a) a change from an absent response to a present response or, (b) a decrease by a factor of two or more in the smallest check size that leads to a detectable response, or, (c) an increase by a factor of two or more in the spatial frequency that leads to a detectable response. (a) is an objective indicator that visual signals have reached the brain, as in the flash VEP test, above. (b) and (c) are objective indicators that visual resolution (acuity) has improved by a factor of two, and thus indicates an improvement that is relevant to visual function and perception. Although the VEP is a standard clinical test, our use of it is different from the clinical routine, in which latency is the primary measurement (Chiappa 1997); our goal is to use it to measure acuity rather than detect conduction delay. By measuring the VEP as a function of check size or grating spatial frequency, visual acuity can be determined (Bach, M et al 2008).

Based on in vitro results described above and in the examples with regard to the performance on a forced choice visual discrimination task, accuracy on a Bayesian stimulus reconstruction test, and performance on an error pattern test, and on the in vivo results described in the examples, treatment with the device will lead to test results from the pattern VEP test as follows: (a) a change from an absent response to a present response or, (b) a decrease by a factor of two or more in the smallest check size that leads to a detectable response, and (c) an increase by a factor of two or more in the spatial frequency that leads to a detectable response.

Sweep VEP, where an improvement consists of (a) an increase by a factor of two or more in the spatial frequency that leads to a detectable response, or (b) a decrease by a factor of two or more in the minimum contrast that leads to a detectable response. (a) is similar to acuity measured by the pattern VEP, above; (b) is an objective measure of contrast sensitivity (gray-level discrimination), which is also relevant to visual function. The sweep-VEP is established as a reliable objective means to assess both acuity (Norcia and Tyler 1985) and contrast sensitivity (Norcia AM et al 1989).

Based on in vitro results described above and in the examples with regard to the performance on a forced choice visual discrimination task, accuracy on a Bayesian stimulus reconstruction test, and performance on an error pattern test, and on the in vivo results described in the examples, treatment with the device will lead to test results from the Sweep VEP test as follows: (a) an increase by a factor of two or more in the spatial frequency that leads to a detectable response, and (b) a decrease by a factor of two or more in the minimum contrast that leads to a detectable response.

For the above tests, the "factor of two" criterion for acuity is chosen because this is approximately a three-line improvement on a standard Snellen or ETDRS eyechart (e.g., from 20/400 to 20/200), a change that is generally recognized as both statistically and functionally significant. Similarly, a "factor of two" criterion is chosen for contrast sensitivity because this corresponds to a two-step improvement on the standard Pelli-Robson contrast-sensitivity eyechart (Pelli DG et al 1988), which is also generally recognized as both statistically and functionally significant.

Other methods to measure clinical efficacy are well known in the art. (Maguire et al 2008) Objective measures include, but not limited to, evaluation of the pupillary light reflex (PLR), full-field electroretinography (ERG) (including bilateral full-field ERG), and nystagmus testing. International Society for Clinical Electrophysiology of Vision standard guideline may be followed for the analyses. Pupil responses may be recorded simultaneously in both eyes. (Kawasaki et al 1995) Nystagmus may be characterized qualitatively and quantitatively by analysis of motion paths in videos taken at baseline and at various desired time points post-treatment. Interpupillary distances may be measured directly from video frames. Subjective measures include, but not limited to, standard tests of visual acuity (VA), kinetic visual field, and mobility testing to assess the ability of the subjects to navigate an obstacle course. For mobility testing, different mazes may be used each time the test is performed and number of obstacles avoided or hit, number of landmarks identified and time spent in the maze can then be assessed. (Simonelli et al 2010)

The examples are offered to illustrate, but not to limit, the claimed invention.

EXAMPLE 1

Method of Building the Encoders

Constructing the Encoders Using an Linear-Nonlinear-Poisson (LNP) Cascade

The parameters for the encoders were constructed from the responses to two sets of stimuli: binary spatio-temporal white noise (WN) and a grayscale natural scene movie (NS) recorded in New York City's Central Park. Both stimuli were presented at a frame rate of 15 Hz, and had the same mean luminance (0.24 µW/cm² on the retina) and contrast (root-mean-squared (RMS) contrast was 0.087 µW/cm²). For the preprocessing step, we chose a=0, and b=255/0.48 µW/cm², so that the visual stimuli are mapped into the numerical range 0-255 (as described above in section entitled, "Encoders").

To determine the spatiotemporal transformation, we used a linear-nonlinear model as described above in the same section (see also, Victor and Shapley 1979; Paninski et al. 2007; Pillow et al. 2008; Nirenberg et al. 2010). Parameters for the model were determined by maximizing the likelihood that the model would produce the experimentally-observed spike trains elicited by the stimuli, as in Nirenberg et al, 2010; similar methods are in Paninski et al. 2007; Pillow et al. 2008, as maximum likelihood optimizations are well known in the art.

For the data in the following examples, neurons were modeled independently. For each neuron, m, the firing rate $\lambda_m$ was determined as in Eq. 1. Each neuron's linear filter was assumed to be a product of a spatial function (on a 10×10 array of pixels, centered on the receptive field) and a temporal function (18 time bins, 67 ms each, total duration 1.2 sec). Dimensionality was reduced by assuming the temporal function to be a sum of 10 impulses and basis functions (raised cosines in log time), as in Nirenberg et al., 2010, following Pillow et al. 2008.

The nonlinearities were parameterized as cubic spline functions with 7 knots. Knots were spaced to cover the range of values given by the linear filter output of the encoders.

As mentioned above, parameters were fit using a standard optimization procedure, as in Nirenberg et al, 2010, following Pillow et al, 2008, Paniniski, 2007. The quantity maximized is the log likelihood of the observed spike trains under the model, as in Eq 2. Because each neuron is independent, the optimization of each neuron's parameters could be carried out independently. To maximize the log likelihood, we used the same procedure as described in the text following Eq. 2 above, which we briefly reiterate here: We began by assuming that the nonlinearity N was exponential, since in this case, the log likelihood Z has no local maxima (Paninski, et al. 2007). After optimizing the linear filters and an exponential nonlinearity (by coordinate ascent), the nonlinearity was replaced by a spline. Final encoder parameters were then determined by alternating stages of maximizing the log likelihood with respect to (i) the spline parameters and (ii) the filter parameters, until a maximum was reached, as described in (Nirenberg et al. 2010), which also discusses the justification of this approach.

Models that take into account history dependence and correlations were also built. Correlations between neurons were modeled using coupling kernels, following the method of (Pillow et al. 2008).

For the spike generation step, for each cell m, we created an inhomogeneous Poisson process with instantaneous firing rate $\lambda_m$. We consider time intervals (bins) of length $\Delta t=0.67$ ms.

Figure 5:
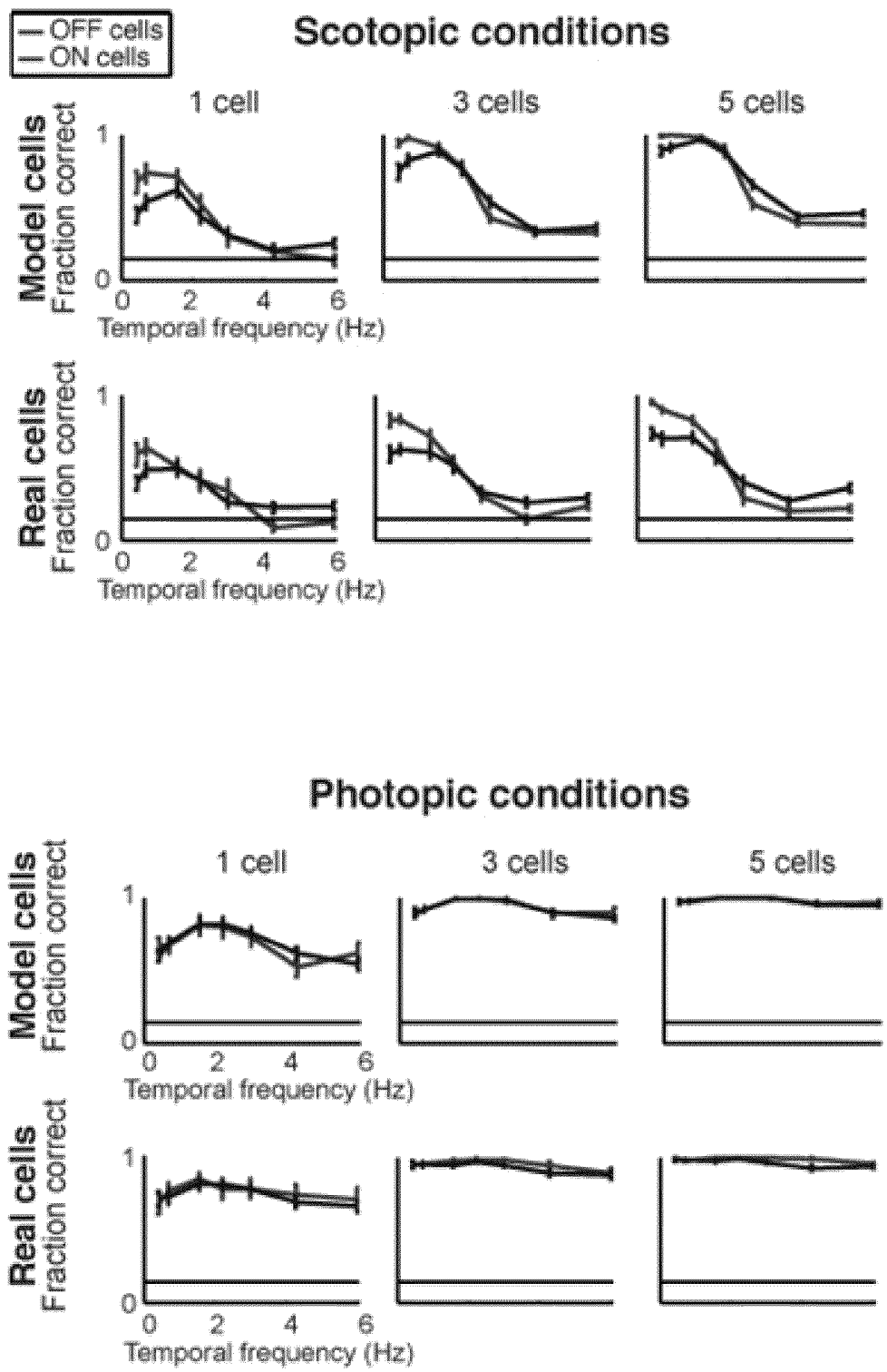
FIG. 5 shows that the encoders (the model cells) make the same predictions as the real cells. Top left, the model indicates that ON cells are better able to distinguish among low temporal frequencies than OFF cells under scotopic conditions, whereas OFF cells are better able to distinguish among high temporal frequencies than ON cells. Bottom left, the real cells indicate the same. Top, looking across scotopic and photopic conditions, the model indicates that these differences in the behavior only occur under scotopic conditions: the two cell classes perform approximately equally well under photopic conditions. Bottom, looking across scotopic and photopic conditions, the real cells indicate the same. Top, looking across the two conditions again, the model shows that ON and OFF cells perform well only for a narrow range of frequencies under scotopic conditions, but over a wide range under photopic conditions. Bottom, looking across the two conditions, again, this prediction held for the real cells as well. Predictions were made with increasing numbers of cells until there was indication of performance saturation. Error bars are SEM.
Figure 6:
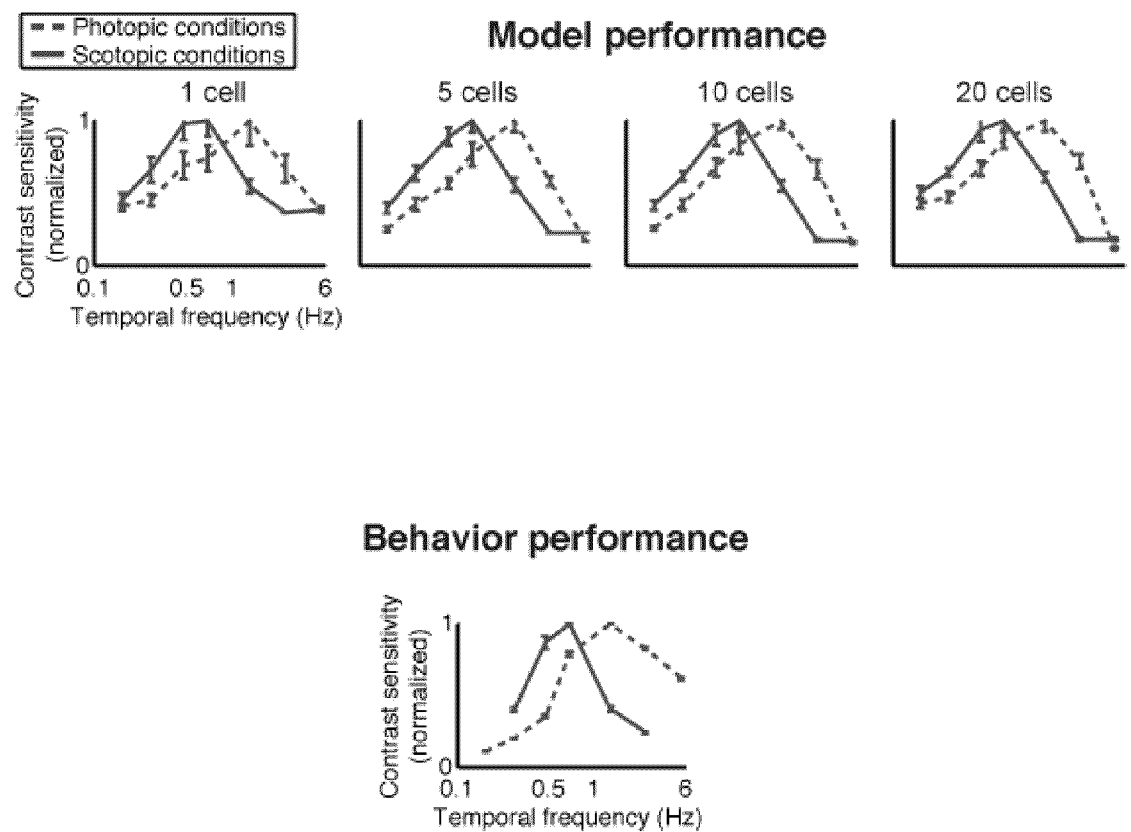
FIG. 6 shows that the encoders (the model cells) predict the shift in optomotor performance. Left, the model predicts a shift toward higher temporal frequencies as the animal moves from scotopic to photopic conditions. Right, the animals' behavioral performance shifted to higher temporal frequencies, as predicted (n=5 animals). The prediction was robust from 1 cell to saturation (20 cells).
Figure 7:
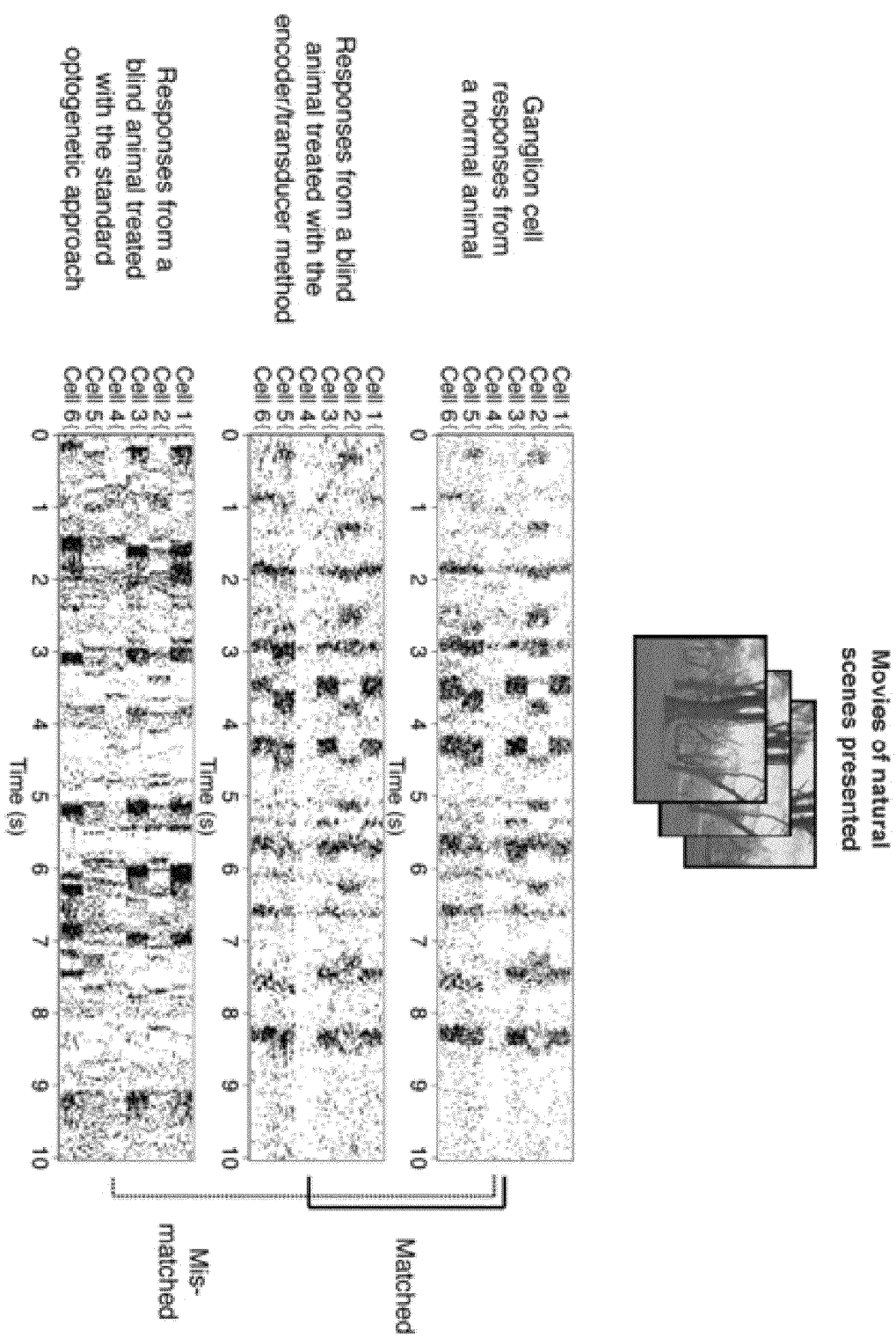
FIG. 7 shows that ganglion cell responses produced by the retina prosthesis closely match those produced by normal retina, whereas ganglion cell responses produced by the standard optogenetic approach (i.e., using ChR2 as the transducer) do not match those produced by normal retina. Movies of natural scenes were presented to three groups of mouse retinas: retinas from normal mice, retinas from blind mice that were treated with the retina prosthesis (i.e. the blind retinas were expressing ChR2 in the ganglion cells and were stimulated with movies that had been processed by the encoders), and retinas from blind mice treated with the standard optogenetic approach (i.e. the blind retinas were expressing ChR2 in the ganglion cells but were stimulated with movies that had not been processed by the encoders). Then spike trains were recorded from the ganglion cells of each group.
Figure 8:
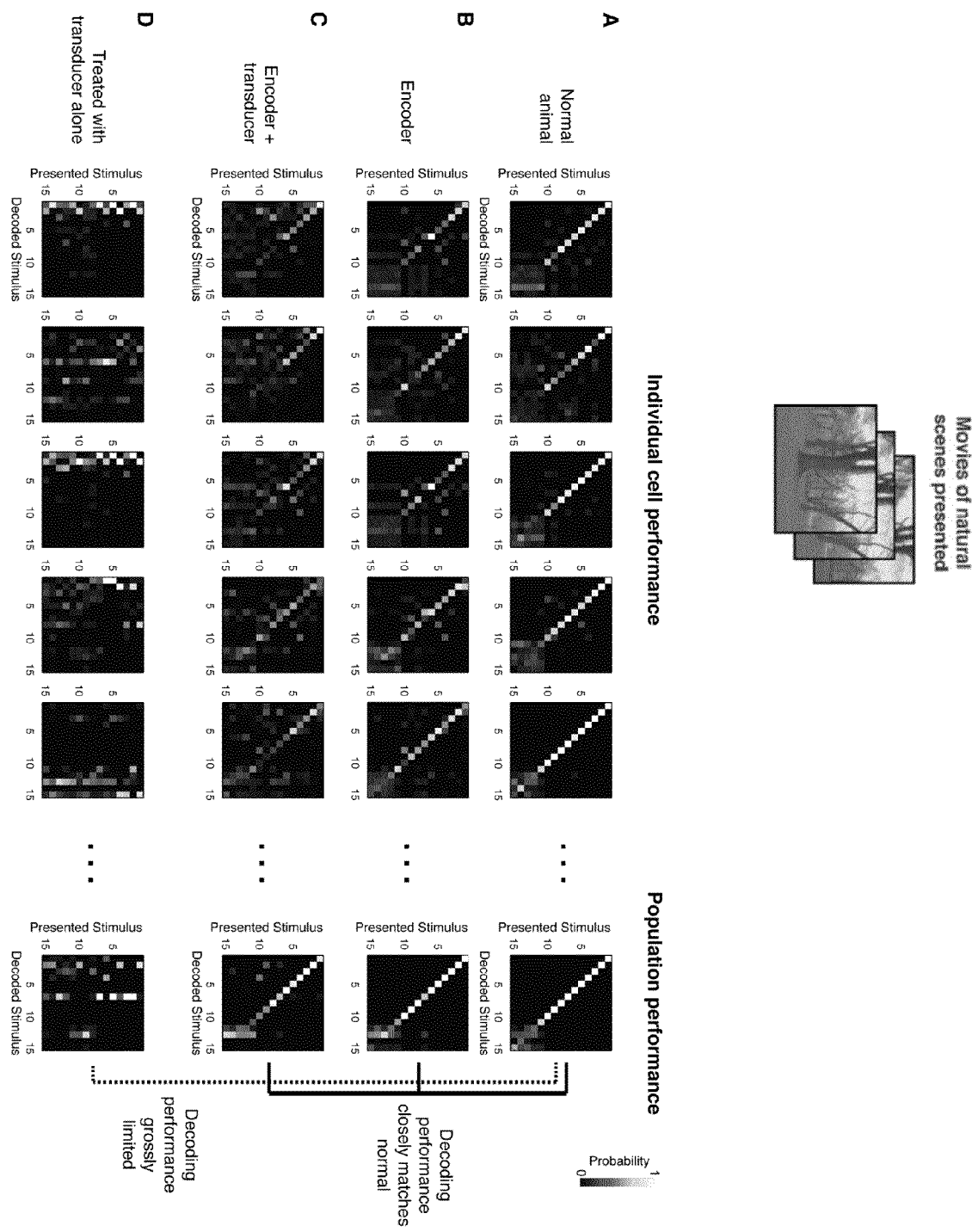
FIG. 8 shows that the performance of the retina prosthesis on a visual discrimination task closely matches the performance of the normal retina, whereas the performance of the standard optogenetic method does not. A. Confusion matrices generated when the testing set was obtained from the normal WT retina. On the left are the matrices for individual ganglion cells, on the right, for a population of cells (20 cells). Fraction correct for the population was 80%. B. Confusion matrices generated when the testing set was obtained from the encoders (note that these encoders were built from the input/output relations of the WT retina used in panel A). Fraction correct was 79%. C. Confusion matrices generated when the testing set was generated from a blind retina, where the ganglion cells were driven with the encoder+transducer. (ChR2). Fraction correct was 64%. D. Confusion matrices generated when the testing set was generated from a blind retina, where the ganglion cells were driven with the standard optogenetic method (i.e., ChR2 alone with no encoders). Fraction correct was 7%.

Note that FIGS. 3-6, 13 and 14 compare the performance of encoders and real cells. FIGS. 7-9 also compare the performance of the encoders, when combined with the transducers. For these experiments, the output of the encoders is passed through an interface that produces light pulses to drive the ChR2 in the ganglion cells. Two methods were used to take the output from the encoders and produce light pulses to drive ChR2. In the first method, the output of the encoders was used to control an LCD panel (Panasonic PT-L104, Panasonic, Secaucus, N.J.). The LCD panel was placed in front of a set of 7 high-intensity blue LEDs (Cree XP-E Blue, Cree, Durham N.C.). Squares on the LCD panel conveyed the output of the encoders for the ganglion cell in the given location. For each frame, the squares were set to the highest intensity (255) if the encoders dictated that the ganglion cell should fire a spike within that frame, or the lowest intensity (0) if the ganglion cell should not fire a spike within that frame. If the LCD panel's intensity was high (255) at a location, the light from the blue LEDs was passed through; if not, the light was blocked. The output of the LCD panel was focused onto the retina. The intensity of the light at the 255 position at the retina was 0.5 mW/mm$^2$. Each frame lasted 16.7 ms. A second method was used where precise spike timing was required. For this method, an LED (Cree XP-E Blue, Cree, Durham N.C.) drove the ganglion cells directly. The output state of the LED was controlled by a computer-generated 5V TTL pulse, which was sent through a control/amplification circuit as described by Campagnola et al., 2008. The LED turned on when the TTL pulse was high (5V), and off when the pulse was low (0V). The output of an encoder was used to drive the TTL pulse through a computer's parallel port using custom software. When the encoder specified that a spike should occur, the TTL pulse was driven high (5V) for 1 ms, and then was turned off again. The intensity of the LED pulse at the retina was 1 mW/mm$^2$ during the on state.

The responses of the transducer alone to visual stimuli (FIGS. 8C, 9D) were recorded using two methods. For the natural movie (FIG. 8C), the ganglion cells were driven using the LED, again controlled by TTL pulses. The output of the LED was set to match the intensity of the natural movie at a ganglion cell's receptive field location, using pulse code modulation. TTL pulses were 1 ms wide. More pulses within a frame represented brighter intensities, while fewer pulses represented dimmer intensities, with linear scaling between intensity and pulse rate. The pulse rate of the LED was updated every 66.7 ms to match the intensity of the natural movie at that frame. The highest intensity of the movie was mapped to the peak firing rate of the encoder for the given ganglion cell—this was typically between 8 and 12 pulses per 66.7 ms frame. For the baby face responses (FIG. 9D), the ganglion cells were driven using the LCD panel. The brightness of the LCD panel (0-255) was set to match the intensity of the baby face movie (0-255) at a given ganglion cell's receptive field location. The intensity of the LED was 1 mW/mm$^2$ at the retina, and the intensity of the LCD at maximum brightness was 0.5 mW/mm$^2$, as described in the previous section.

EXAMPLE 2

Determining the Parameters for the Spatiotemporal Transformation

We describe a procedure to determine the parameters for the spatiotemporal transformations. Parameters discussed are as in the section "Encoders" above.

In this example, first, the experiment is performed, and ganglion cell responses to WN and NS stimuli are collected (see "Example 1—Method of Building the Encoders" for an example of stimuli). Next, the reverse correlation between the ganglion cell action potential times and the stimulus intensity is calculated, to determine a starting set of values for the linear filter $L_m$. Next, the linear filter is assumed to be separable, a product of a spatial function and a temporal function. The spatial function is parameterized as a 10 by 10 grid of weights, and the temporal function is parameterized as the sum of 10 weighted temporal basis functions. At this stage, the nonlinearity $N_m$ is assumed to be an exponential function to ensure there are no local maxima. Next, the likelihood for this set of parameters is calculated for the given stimulus and recorded ganglion cell's responses. The next step is to find the optimal parameters for the spatial function, temporal function, and exponential nonlinearity, by maximizing the likelihood of these parameters using gradient ascent (as is well described, see: Paninski et al., 2007, Pillow et al., 2008, Nirenberg et al., 2010). After these parameters are optimized, the exponential nonlinearity is replaced by a 7-knot cubic spline, which more accurately describes the cell's responses. Next, the parameters of the spline are optimized to maximize the likelihood. Subsequently, the parameters of the spatial and temporal functions are optimized to maximize the likelihood given the new spline parameters. These two steps (optimizing the spline parameters while holding the spatial and temporal functions constant, then optimizing the spatial and temporal functions while holding the spline parameters constant) are repeated until the change in likelihood from the two steps is less than an arbitrarily chosen small number.

EXAMPLE 3

Comparison of Amount of Information Carried by Virtual Retinal Cell and Real Retinal Cell To build the data set, we recorded the responses of several hundred mouse retinal ganglion cells (515 cells) to a broad range of stimuli, including natural and artificial stimuli, which for this experiment was checkerboard, natural scenes, and drifting gratings. For each cell, we constructed its encoder (also referred to as its virtual retinal cell, or model cell). This was achieved as follows. We presented WN (white noise) and NS (natural or naturalistic stimuli) stimuli to retinas and recorded the responses of the ganglion cells and parameterized the stimulus/response relationship for each cell, as described above. We then tested the encoders using additional natural scene and drifting grating responses. Thus, all tests were performed using novel stimuli.

Figure 3:
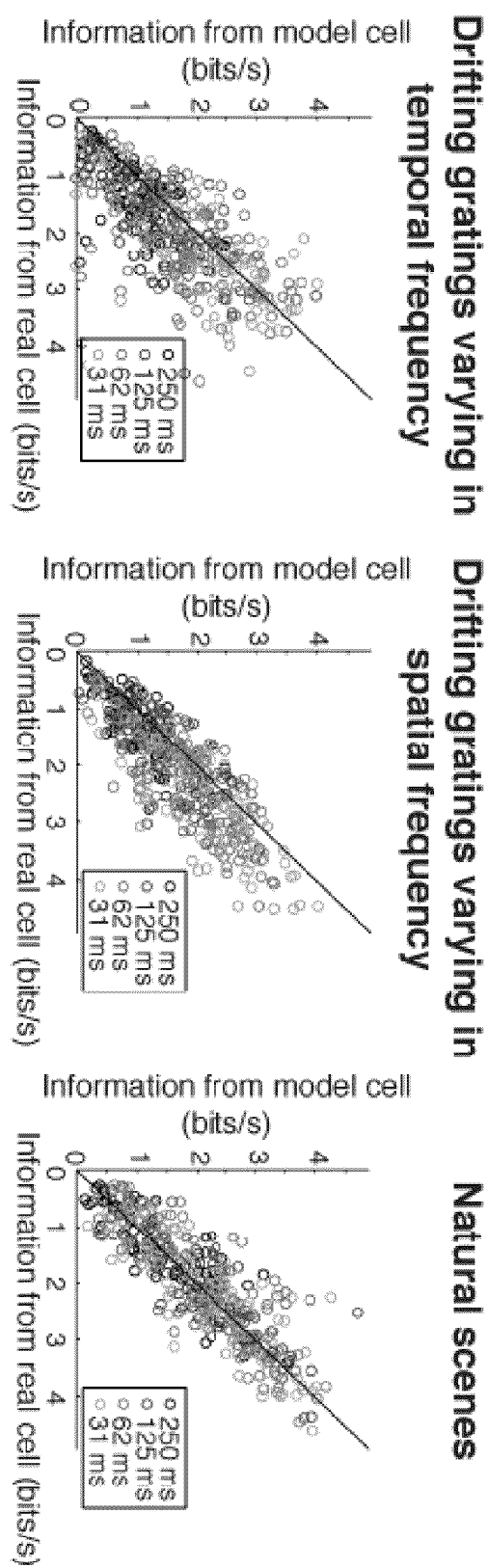
FIG. 3 shows that the amount of information carried by the encoders (the model cells) closely matches that carried by their real cell counterparts. For this analysis, we used three stimulus sets—drifting gratings that varied in temporal frequency, drifting gratings that varied in spatial frequency, and natural scenes. For each cell, we calculated the mutual information between its model cell's responses and the stimuli and plotted it against the mutual information between the real cell's responses and the stimuli (n=106, 118, and 103, for the three sets of stimuli respectively; stimulus entropy for each was 5 bits; bin sizes ranged from 250 to 31 ms).

FIG. 3 shows the results of the information analysis. We recorded from several hundred ganglion cells and modeled their responses. We then presented a large array of stimuli to both the model cells and the real cells—stimuli that were not used to build the encoders. We calculated the amount of information each virtual cell carried about the stimuli and compared it to the amount of information carried by its real cell counterpart. As shown in the figure, the virtual cells carried nearly all the information carried by the real cells. Each stimulus set was presented to at least 100 real cells so that we had substantial data for each analysis. We then assessed the robustness of the results by carrying out the calculations multiple times. As expected, the information carried by the real cells increased with the increase in temporal resolution, and, as shown in the figure, the information carried by the virtual cells followed suit.

EXAMPLE 4

Figures 1, 4:
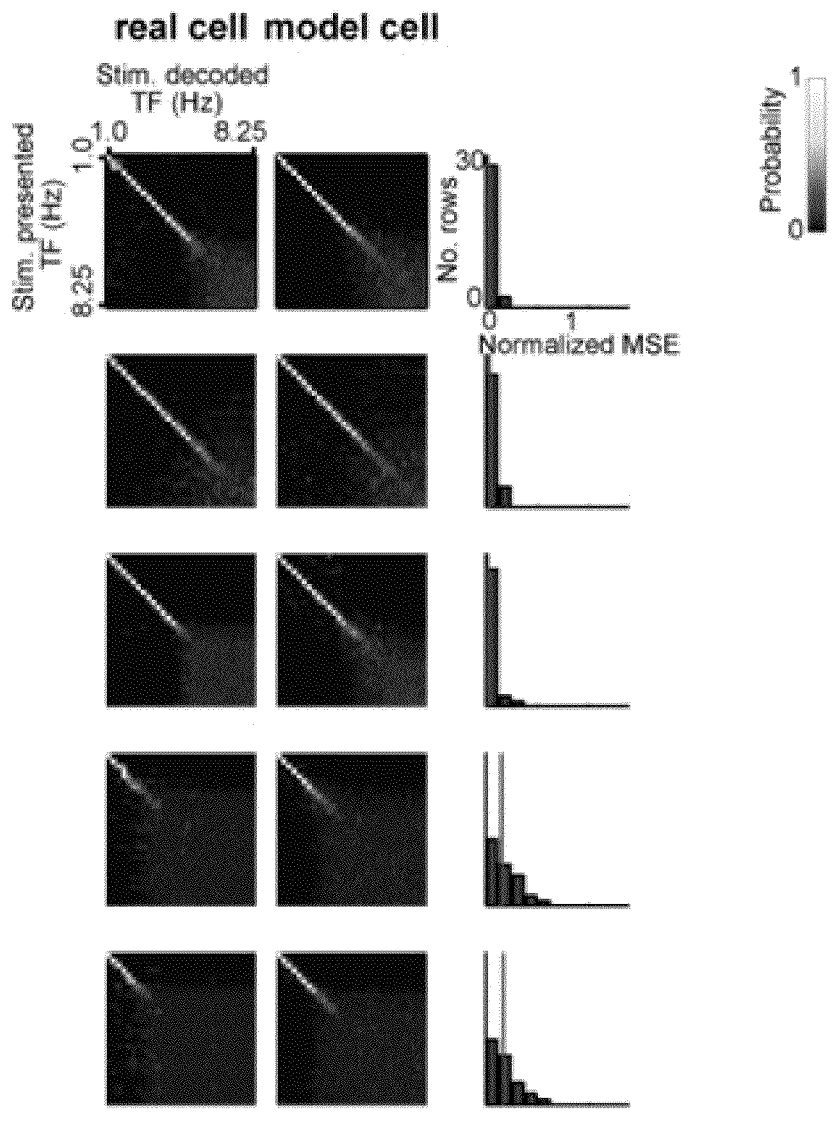
FIG. 4 (FIGS. 4-1, 4-2, and 4-3) shows that the posterior stimulus distributions of the encoders (the model cells) closely match those of their real cell counterparts. A. For each cell, we plotted a pair of matrices. The matrix on the left gives the posterior for the model cell's responses (averaged over all responses); the matrix on the right gives the same for the real cell's responses. The histogram next to the pair gives a measure of the distance between them. Briefly, for each row, we computed the mean squared error (MSE) between the model's posterior and the real cell's posterior and then normalized it by dividing it by the MSE between the real cell's posterior and a randomly shuffled posterior. A value of 0 indicates that the two rows are identical. A value of 1 indicates that they are as different as two randomly shuffled rows. (Because of data limitation, occasional cells showed values higher than 1.) The vertical light grey line indicates the median value of the histogram. B. Histogram of the median values for all cells in the data set, and histogram of K-L divergences for all cells in the data set (n=106, 118 and 103 cells for the stimuli, respectively).
Figures 2, 4:
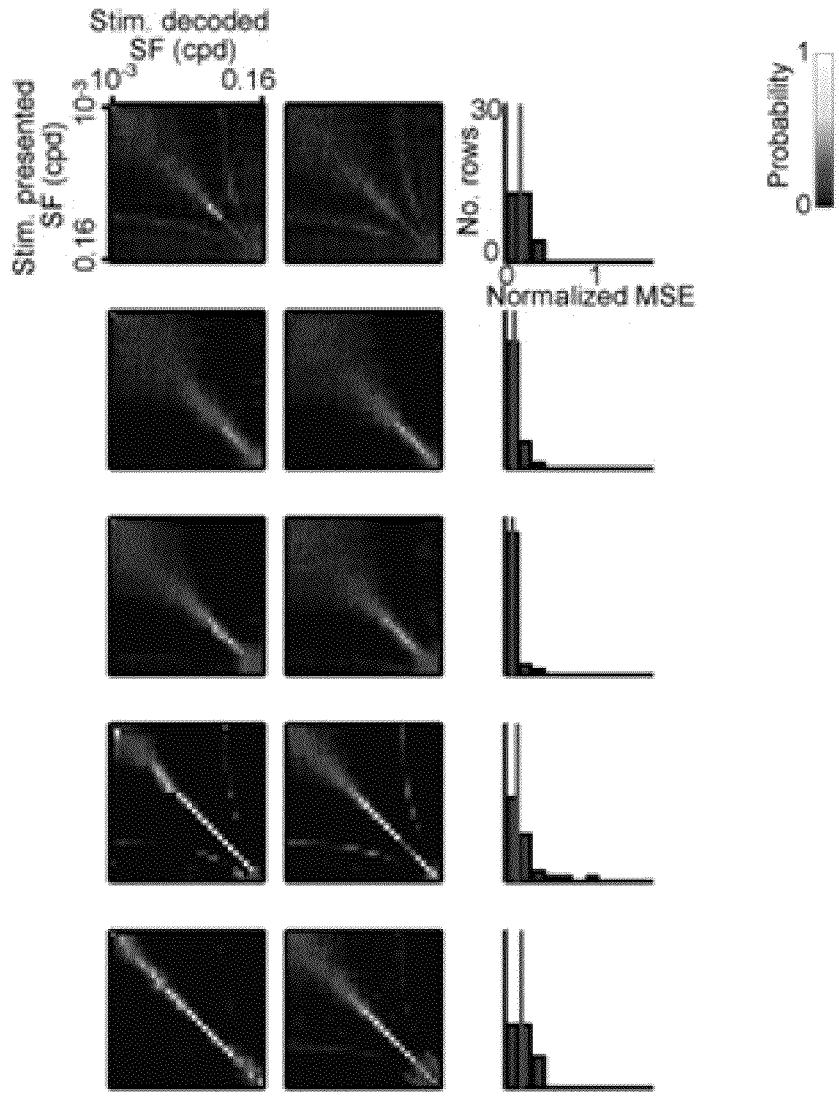
Figure 4:
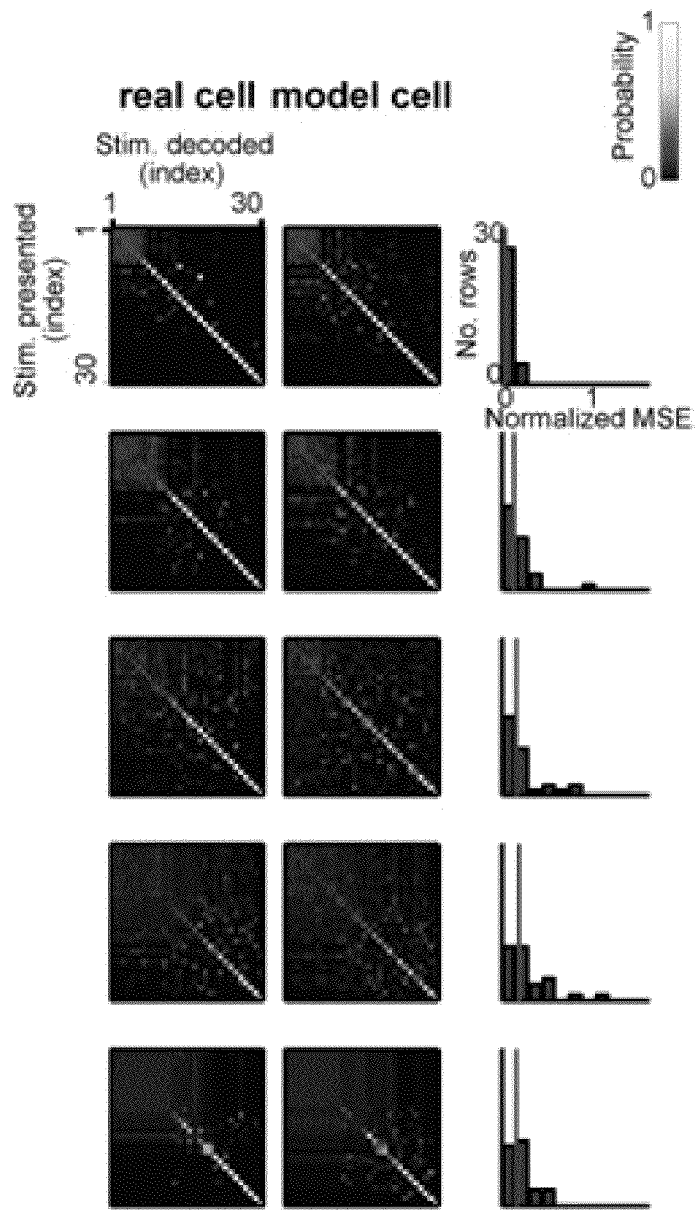
Figure 3:
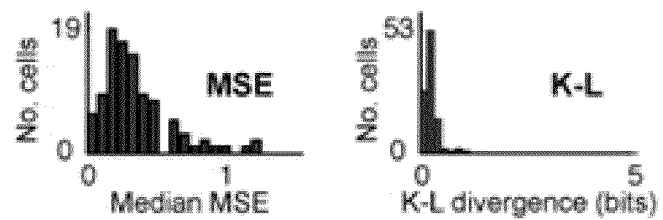

Comparison of Quality of Information Carried by Virtual Retinal Cell and Real Retinal Cell FIG. 4 shows that the quality of the information carried by the virtual cells and the real cells is also the same. For each cell in FIG. 4, we compared the posterior stimulus distributions generated by the virtual cell's responses with the posterior stimulus distributions generated by the real cell's responses. FIG. 4A shows several examples, and FIG. 4B shows histograms of the results for all the cells in the dataset.

To understand what the matrices show, we go through one in detail—the one in the top left corner of panel of panel A of FIG. 4-1. The vertical axis gives the presented stimuli, and the horizontal axis gives the "decoded" stimuli (that is, the posterior distribution of stimuli). In the top row, there is a single bright square, and it is located at the left-most position. What this means is that when the presented stimulus is the grating with the lowest temporal frequency, the decoded stimulus will be correct—that is, the posterior stimulus distribution is sharply peaked (as indicated by the single bright square), and the peak is at the correct position (the position that corresponds to the lowest temporal frequency). In contrast, in the bottom row of the matrix, there is no single bright spot, just a stretch of red squares on the right region of the row. What this means is that when the presented stimulus is the highest temporal frequency grating, the decoding will likely fall short—the posterior is broad and providing only limited information about what the stimulus is. It's indicating that the stimulus is likely a high frequency grating, but it's not indicating which high frequency in particular.

The significance of this figure is two-fold. It shows, first, there are many different kinds of posteriors among the real cells (e.g. there are many types of ganglion cells in terms of their visual responses and sensitivities to stimuli); and, second, that the virtual cells accurately reproduce them, e.g., some cells provide information about low frequencies, others provide information about high frequencies, or show complex patterns, etc. But in nearly all cases, with several hundred cells examined, the behavior of the real cell is captured by the encoder: The posterior produced by each virtual cell closely matches that produced by the real cell. This provides strong evidence that the virtual cells can serve as proxies for the real cells.

EXAMPLE 5

Retinal Ganglion Cell Response Prediction by the Encoders

We used our encoders to make a set of predictions about the behavior of the ganglion cell classes, and then tested the predictions. The predictions in this case focused on differences in the way ON and OFF cells pull out motion information, specifically, slow motion.

This was achieved as follows. First, we constructed an encoder for the cell. We presented WN and NS stimuli to wt (wild type) retinas and recorded the responses of the ganglion cells and parameterized the stimulus/response relationship as described above. The ganglion cell population included both ON and OFF cells. We separately generated parameters for ON and OFF cells and used the parameters to generate ON and OFF encoders. To make the predictions, we set up a visual discrimination task. We presented the different versions of the encoder with drifting gratings that varied in temporal frequency and obtained responses. We then decoded the responses (using Bayesian (i.e. maximum likelihood) as described herein). On each trial of the task, we asked: given the responses, what was the most likely frequency of the grating. Then, for all trials we tallied the fraction of times the correct answer was obtained. To make specific predictions about ON and OFF cells, we performed the task with populations made up exclusively of ON cells or exclusively of OFF cells. We also ran the task with encoders in which the parameters were determined using both scotopic (night light) and photopic (daylight) light levels, since ganglion cells are known to behave differently under these conditions (Purpura et al 1990; Troy et al 2005; Troy et al 1999).

Several results quickly emerged. The first one was that ON cells were better able to distinguish among low temporal frequencies (slow motion) than OFF cells, under scotopic conditions. The second was that OFF cells were better able to distinguish among high temporal frequencies than ON cells, also under scotopic conditions. The third was that these differences existed only under scotopic conditions: the two cell classes performed approximately equally well under photopic conditions. Finally, the last one was that ON and OFF cells performed well only for a narrow range of frequencies under scotopic conditions, but over a wide range under photopic conditions.

We then tested the predictions. We started with electrophysiological measurements. We presented the same stimuli to the retina on a multi-electrode array and recorded ganglion cell responses. We then decoded them as we decoded the virtual cell responses, i.e., using maximum likelihood. As shown in FIG. 5, the real cells make the same predictions as the virtual cells, thus indicating, in a bottom line test, that the virtual cells can serve as proxies for the real cells.

EXAMPLE 6

Animal Behavior Prediction by the Encoder

Finally, we moved to predictions about behavior. For this, we used an optomotor task because it is a) simple, b) readily quantifiable, and c) allows us to selectively probe a single cell class by itself, the ON cells (only ON cells project to the accessory optic system (AOS), which drives this behavior) (Dann and Buhl 1987; Giolli et al 2005). In this task, the animal (a wt mouse) is presented with a drifting grating, and it either tracks it or fails to track it. So to make predictions about behavior, we asked the encoders the same question as we asked the animal: is the grating present or absent? We used an approach parallel to the one used for testing predictions in the electrophysiological experiments—that is, we decoded the responses using maximum likelihood. The only difference is that for the comparison with behavior, we decoded the encoders' responses into just two alternatives (grating present versus grating absent), since this corresponds to the alternatives of the behavioral task. Finally, for both the animal and the encoders, we presented stimuli that represented photopic (daylight) or scotopic (night light) conditions and measured contrast sensitivity, which is defined as the contrast at which 75 percent of the stimuli were correctly decoded, as is standard for 2-alternative forced choice psychophysics. As shown in FIG. 6, the encoders correctly predict the shift in optomotor performance.

EXAMPLE 7

Retinal Ganglion Cell Firing Patterns Generated by the Encoders

We presented movies of natural scenes and recorded ganglion cell responses from retinas taken from three groups of animals: a) normal animals, (briefly: retinas were extracted from wild type (WT) mice; the retinas were then presented with movies of natural scenes, and the firing patterns of the ganglion cells were recorded) (FIG. 7 top), b) blind animals that were treated with the retinal prosthetic (briefly: retinas were extracted from doubly transgenic mice bred in our lab from commercially available sources, which have retinal degeneration and which also express channelrhodopsin-2 in retinal ganglion cells; the retinas were presented with the encoded natural scene movies and the firing patterns of the ganglion cells were recorded) (FIG. 7 middle), and c) blind animals treated with the approaches of current optogenetic prostheses (briefly: retinas were extracted from the same doubly transgenic mice as above; the retinas were then presented with natural scene movies (no encoding) and ganglion cell firing patterns were recorded) (FIG. 7 bottom).

In the normal retinas, the movies are converted into patterns of action potentials (also referred to as spike trains) by the retinal circuitry. The spike trains from the normal retinas are shown in FIG. 7, top. In the retinas from the blind animals treated with the encoder/transducer method, the movies are converted into spike trains by the encoder/transducer (FIG. 7, middle). As shown in the figure, the spike trains produced by this method closely match those produced by normal ganglion cells. This happens because the encoders reproduce ganglion cell spike trains very reliably, and because ChR2 has fast enough kinetics to follow the output of the encoders. Thus, we were able to mimic normal retinal input/output relations. For comparison, see FIG. 7, bottom; this shows the output of the standard optogenetic method (which is just the transducer, i.e., just ChR2 as in Lagali et al 2008; Tomita et al 2010; Bi A et al. 2006; Zhang et al. 2009; Thyagarajan et al. 2010. In this case, the stimuli (the natural scene movies) are activating the ChR2 directly. While this approach makes the ganglion cells fire, the firing patterns it produces are not the normal firing patterns.

EXAMPLE 8

Performance of the Encoders and of the Retinal Prosthetic

Figure 10:
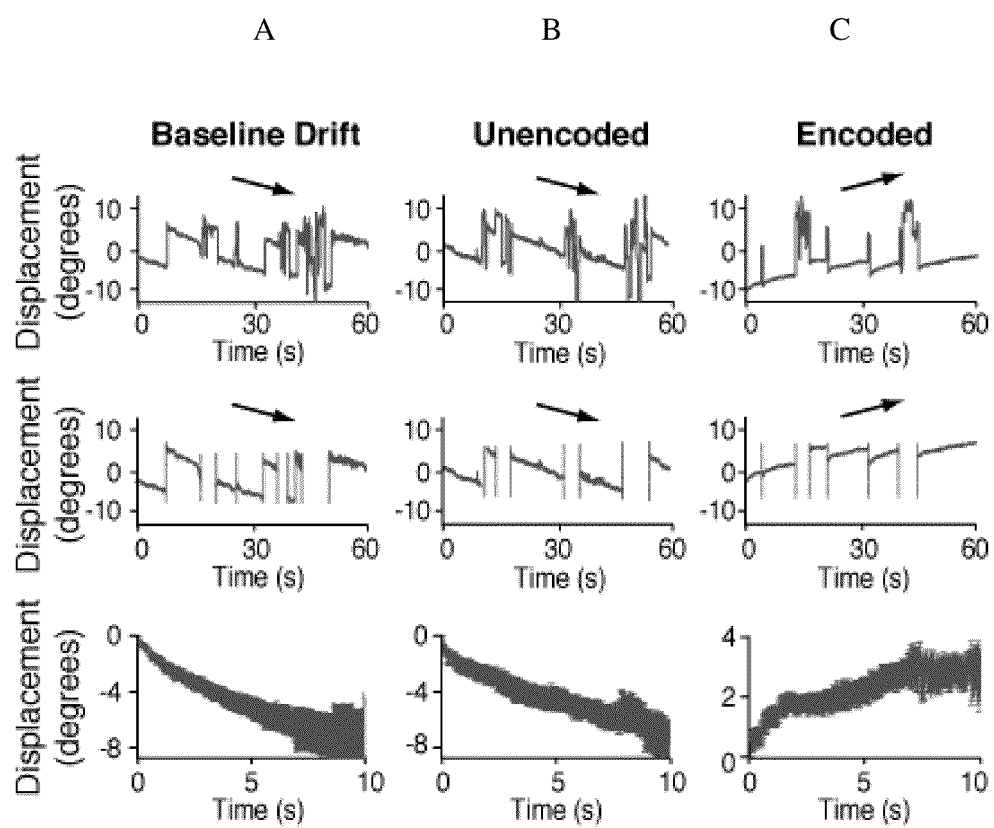
FIG. 10 shows that tracking occurs with the retina prosthesis. A. Baseline drift (no stimulus present). As mentioned in the text, blind animals show a drift in eye position, similar to the drift observed with blind humans. B Response to drifting grating presented using the standard optogenetic method (i.e., presented on the screen as it is). C. Response to drifting grating presented using the retina prosthesis (i.e., presented on the screen in its encoded form). When the image has been converted into the code used by the ganglion cells, the animal can track it. Top row, raw eye position trace, a representative example. Middle row, smooth component (saccades and movement artifacts removed, see raw trace above). Bottom row, average trajectory across all trials (n=15, 14, and 15 trials, respectively).

We assessed the performance of the encoder and prosthetic in three ways: using a discrimination task method (FIG. 8), image reconstruction (FIG. 9), and performance on a behavioral task (optomotor) (FIG. 10). The measures and results are presented below.

Performance on a Visual Discrimination Task

We started with the discrimination task. Briefly, we presented an array of stimuli and measured the extent to which they could be distinguished from each other, based on the responses of the ganglion cells (or encoders). For ganglion cell recordings, stimuli were presented on a computer monitor, and ganglion cell responses were recorded with a multielectrode array as in Pandarinath et al, 2010.

To decode the responses in the test set, we determined which of the stimuli $s_j$ was the most likely to produce it. That is, we determined the stimulus $s_j$ for which $p(r|s_j)$ was maximal. This was done via Bayes theorem, which states that $p(s_j|r)=p(r|s_j)p(s_j)/p(r)$, where $p(s_j|r)$ is the probability that the stimulus $s_j$ was present, given a particular response r; $p(r|s_j)$ is the probability of obtaining a particular response r given the stimulus $s_j$; and $p(s_j)$ is the probability that the stimulus $s_j$ was present. Because $p(s_j)$ was set equal for all stimuli in this experiment, Bayes Theorem means that $p(s|r_j)$ is maximized when $p(r|s_j)$ is maximized. (When $p(s_j)$ is uniform, as it was in this case, this method of finding the most likely stimulus given a response is referred to as maximum likelihood decoding (Kass et al. 2005; Pandarinath et al. 2010; Jacobs et al. 2009). For each presentation of stimulus $s_i$ that resulted in a response r that was decoded as the stimulus $s_j$, the entry at position (i,j) in the confusion matrix was incremented.

To build the response distributions needed for the decoding calculations used to make the confusion matrices (i.e., to specify $p(r|s_j)$ for any response r), we proceeded as follows. The response r was taken to be the spike train spanning 1.33 sec after stimulus onset and binned with 66.7 ms bins. Since the spike generation process is assumed to be an inhomogeneous Poisson process, the probability $p(r|s_j)$ for the entire 1.33 s response was calculated as the product of the probabilities for each 66.7 ms bin. The probability assigned to each bin was determined by Poisson statistics, based on the average training set response in this bin to the stimulus $s_j$. Specifically, if the number of spikes of the response r in this bin is n, and the average number of spikes in the training set responses in this bin is h, then the probability assigned to this bin is $(h^n/n!)\exp(-h)$. The product of these probabilities, one for each bin, specifies the response distributions for the decoding calculations used to make the confusion matrices. Results similar to those shown in FIG. 8 were obtained with a range of bin sizes (50 to 100 ms) and random assignments to training and test sets.

Once the confusion matrices were calculated, overall performance was quantified by "fraction correct", which is the fraction of times over the whole task that the decoded responses correctly identified the stimuli. The fraction correct is the mean of the diagonal of the confusion matrix. Given this procedure, we performed 4 sets of analyses. For each one, we used the responses from the WT retina for the training set and a different set of responses for the test set. We generated 4 test sets.

(1) The first set consisted of responses from the WT retina. This is done to obtain the fraction correct produced by normal ganglion cell responses.

(2) The second set consisted of the responses from the encoders (the responses from the encoders are, as indicated throughout this document, streams of electrical pulses, in this case, spanning 1.33 sec after stimulus presentation, and binned with 66.7 ms, as are the WT ganglion cell responses). When we use the responses from the encoders as the test set, we obtain a measure of how well the encoders perform, given the response distributions of the normal WT retina. In other words, we start with the assumption that the brain is built to interpret the responses of the normal WT retina (i.e., the naturally encoded responses.) When we use the responses from the encoders as our test set, we obtain a measure of how well the brain would do with our proxy of the normal retinal responses (our proxy of the retina's code).

(3) The third set consisted of the responses from a blind animal driven by the encoders and transducers (ChR2 in the ganglion cells), with the responses of the same duration and bin size as above. This set gives us a measure of how well the encoders perform after their output has been passed through the transducer in real tissue. (While the transducer follows the encoder very closely, it is not perfect, and this provides a measure of how well the complete system (the encoders+transducers) performs.

(4) Finally, the last set consists of the responses from a blind animal driven by just the transducers (ChR2 in the ganglion cells), with responses of the same duration and bin size as above. This gives us a measure of how well the standard optogenetic method performs.

The results are shown in FIG. 8. FIG. 8A shows the confusion matrixes generated when the test set was obtained from the normal WT retina. On the left are the matrices for individual ganglion cells, on the right, for a population of cells (20 cells). As shown, the individual cells each carry a fair amount of information; together as a population, they can discriminate nearly all stimuli in the set. The fraction correct was 80%. FIG. 8B shows the confusion matrixes generated when the test set was obtained from the encoders (note that these encoders were built from the input/output relations of the WT retina used in FIG. 8A). The fraction correct was extremely close to that produced by the WT retina 79%. FIG. 8C shows the results for the complete system (the encoders+transducers). The individual cells do not carry quite as much information, but together as a population, they perform very well. The fraction correct was 64%. Finally, FIG. 8D shows the results with the standard optogenetic method. The individual cells here carry little information, and even as a population, they are still quite limited. The fraction correct was 7%, close to chance. Thus, the incorporation of the encoders, that is, the incorporation of our proxy of the retina's neural code, even for a small population of 20 cells, has a very large effect and can dramatically boosted prosthetic performance.

Finally, to summarize these data, we compared the percent performances of the encoders alone (FIG. 8B), the encoders+ transducers (FIG. 8C), and the standard optogenetic method (FIG. 8D) to that of the normal retina (FIG. 8A). Results are as follows: the encoders' performance was 98.75% of the normal retina's performance, the complete system's performance, that is, the performance of the current embodiment of the encoders+transducers, was 80% of the normal retina's performance, and the performance of the standard method (just transducer alone) was less than 10% of the normal retina's performance (8.75%).

Reconstructing Stimuli from the Ganglion Cell (or Encoder) Responses

Next, we performed stimulus reconstructions. Stimulus reconstruction uses a standard maximum likelihood approach to determine the most likely stimulus presented given a set of spike trains (reviewed in Paninski, Pillow, and Lewi, 2007). While the brain does not reconstruct stimuli, reconstructions serve as a convenient way to compare prosthetic methods and to give an approximation of the level of visual restoration possible with each approach.

The stimulus consisted of a uniform gray screen for 1 second, followed by a given image for 1 second, preferably a human face. Note that each pixel of the stimulus must span a reasonable region of visual space, so that features of the image, in this case a face, can be discerned. This criterion was satisfied by the choice of 35 by 35 pixels per face, as shown in FIG. 9. This is consistent with the fact that facial recognition makes use of spatial frequencies at least as high as 8 cycles per face, which requires at least 32 pixels in each dimension for adequate sampling (Rolls et al., 1985). In the example shown in FIG. 9, which uses mouse, each pixel corresponded to 2.6 degrees by 2.6 degrees of visual space. This in turn corresponds to approximately 12-20 ganglion cells on the mouse retina.

Reconstructing the stimulus consists of a search over the space of all possible stimuli to find the most likely stimulus given the measured population response r. To find the most likely stimulus given r, we used Bayes' theorem, $p(s|r) = p(r|s)*p(s)/p(r)$. Because the a priori stimulus probability $p(s)$ is assumed to be constant for all s, maximizing $p(s|r)$ is equivalent to maximizing $p(r|s)$.

To determine $p(r|s)$, it is assumed that the cells' responses are conditionally independent that is, it is assumed that $p(r|s)$ is the product of the probabilities $p(r_j|s)$, where $p(r_j|s)$ is the probability that the jth cell's response is $r_j$, given the stimulus s. The rationale for this assumption is that it has been shown that deviations from conditional independence are small, and contribute only a small amount to the information carried (Nirenberg et al, 2001; Jacobs et al, 2009) and to the fidelity of stimulus decoding.

To calculate $p(r_m|s)$ for a given cell m, the response $r_m$ was taken to be the spike train of the mth cell spanning 1 sec after stimulus onset and binned with 0.67 ms bins. Since the spike generation process is assumed to be an inhomogeneous Poisson process, the probability $p(r_m|s)$ for the entire 1 sec response was calculated as the product of the probabilities assigned to each bin. The probability assigned to each bin was determined by Poisson statistics based on the cell's expected firing rate in this bin to the stimulus s. The cell's expected firing rate is calculated from Eq. 1 (see section "The Encoders," under "Spatiotemporal Transformation Step"), as the quantity $\lambda_m(t;X)$, where X in Eq. 1 is taken to be the stimulus s, and t is the time of the bin. Finally, the probability of the response for the population of cells, $p(r|s)$, is calculated by multiplying the probabilities of the responses of the individual cells $p(r_j|s)$.

To find the most likely stimulus $s_j$ for the population response, r, we used standard gradient ascent techniques. Since we wished to find the stimulus $s_j$ that maximizes the probability distribution $p(r|s)$, and the stimulus space is high-dimensional, the gradient ascent method provides an efficient way to search through this high-dimensional space. Briefly, we began by starting at a random point in stimulus space, $s_k$. We evaluated the probability distribution $p(r|s_k)$ for this stimulus, and also calculated the slope of this probability distribution with respect to each dimension of the stimulus. We then created a new stimulus $s_{k+1}$, by changing the stimulus $s_k$ in the direction of increasing probability (as determined from the slope of the probability distribution). This process continued iteratively until the probability of the stimulus increased only a marginal amount, i.e., until we reached the peak of $p(r|s)$. Note that because the probability distribution is not strictly log-concave, there exists the possibility of getting stuck in local maxima. To verify that this was not occurring, we performed the reconstructions using multiple random starting points and confirmed that they converged to the same peak.

To compare the performance of the prosthetic methods, we performed reconstructions using 3 sets of responses: 1) the responses of the encoders, 2) the responses from a blind retina, where the ganglion cells were driven by the encoders+ transducers (ChR2), and 3) responses from a blind animal, where the ganglion cells were driven by just the transducers (i.e., just ChR2). The reconstructions were carried out on our processing cluster in blocks of 10×10 or 7×7 pixels.

The results are shown in FIG. 9. To obtain a large enough dataset for the complete reconstruction, we moved the image systematically across the region of retina we were recording from, so that responses to all parts of the image could be obtained with a single or small number of retinas. Approximately 12,000 ganglion cell responses were recorded for each image. FIG. 9A shows the original image. FIG. 9B shows the image produced by the responses of just the encoder. Not only is it possible to tell that the image is a baby's face, but one can also tell that it is this particular baby's face, a particularly challenging task. FIG. 9C shows the image produced by the responses from the encoders/transducers. While not quite as good, it's still close. Finally, FIG. 9D shows the image produced by the responses from the standard method (i.e., just ChR2). This image is much more limited. The results of this figure, again, indicate that incorporation of the retina's code has substantial impact on the quality of the performance.

To quantify the differences in the performance of the methods, we compared each method's reconstruction with the original image. To do this, we calculated the standard Pearson correlation coefficient between the reconstructed image's values at each pixel, and that of the real image. Thus, a correlation coefficient of 1 indicates that all of the original image's information was perfectly retained, while a correlation coefficient of 0 indicates that the resemblance of the reconstruction to the real image was no greater than chance.

Results were as follows: for the encoders alone, the correlation coefficient was 0.897; for the encoders+transducers, the correlation coefficient was 0.762, and for the transducers alone (corresponding to the current art), the correlation coefficient was 0.159. Thus, just as we found for the discrimination task, the performance of the encoders+transducers was several-fold better than the performance of the current art.

Performance on an Optomotor Task.

Lastly, we performed a set of behavior experiments using an optomotor task. The results are shown in FIG. 10. Briefly, animals were presented with a drifting sine wave grating on a monitor and the animals' eye position was recorded with ISCAN PCI Pupil/Corneal Reflection Tracking Systems (IS-CAN Corp., Woburn, Mass.). We later analyzed the recording and correlated the motion with the motion of the stimulus. The left panel, FIG. 10A, shows the baseline drift (no stimulus). Blind animals show drift in eye position, similar to that observed with blind humans. FIG. 10B (the central column) shows the results for doubly transgenic mice bred in our lab from commercially available sources, which have retinal degeneration and which also express channelrhodopsin-2 in retinal ganglion cells. These mice were shown the raw stimulus. This models the standard optogenetic method. FIG. 10C (right column) shows the results for a model our prosthetic. Doubly transgenic mice bred in our lab from commercially available sources, which have retinal degeneration and which also express channelrhodopsin-2 in retinal ganglion cells, were shown the output of our encoders instead of the raw stimulus. As shown in the figure, tracking was not produced by the mice modeling the standard optogenetic method, but was produced by the mice modeling our prosthetic. When the image has been converted into the code used by the ganglion cells, the animal becomes able to track it.

EXAMPLE 9

Conversion from Images to Light Pulses

Figure 12:
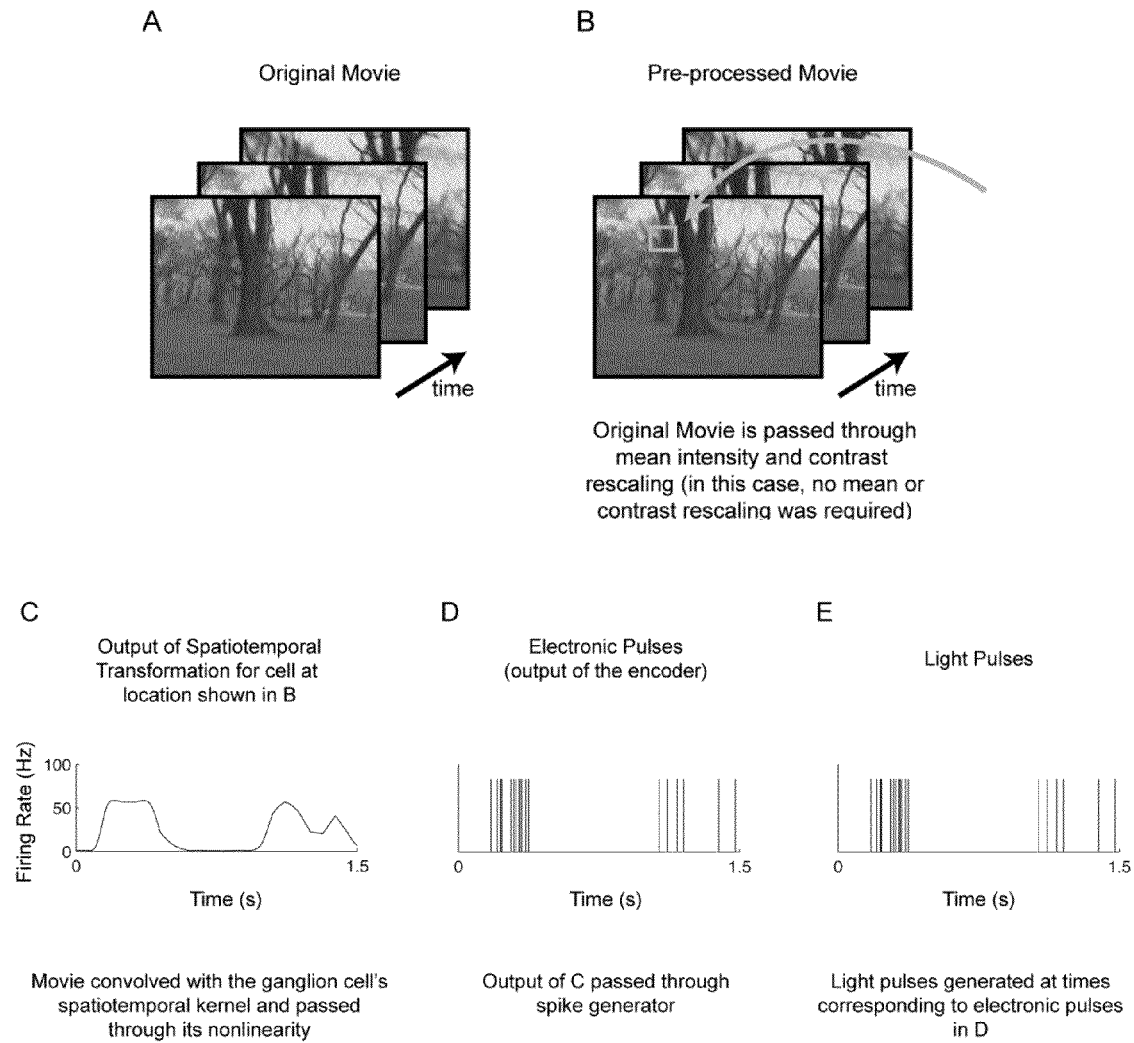
FIG. 12 illustrates the conversion from image to light pulses for an example encoder. A shows an example movie. B shows the pre-processed movie and indicates the position of the example encoder that produces the output in C-E. C shows the output of the spatiotemporal transformation step. D shows the output of the spike generation step. E shows the light pulses that correspond to the output produced by the spike generation step.

The schematic in FIG. 12 illustrates the conversion from image to light pulses for an example encoder. FIG. 12A shows an example movie, a scene from Central Park. FIG. 12B shows the pre-processed movie. The mean intensity and contrast are scaled to match the operating range of the spatiotemporal transformation. In this example movie, no mean or contrast rescaling was required. FIG. 12B also indicates the position of the example encoder that produces the output in FIGS. 12C-E. FIG. 12C shows the output of the spatiotemporal transformation step. The pre-processed movie is convolved with the example cell's spatiotemporal kernel and passed through its nonlinearity to produce a firing rate. FIG. 12D shows the output of the spike generation step. The firing rate produced by the spatiotemporal transformation is passed through the spike generator, which produces a series of electronic pulses. FIG. 12E shows the light pulses that correspond to the output produced by the spike generation step.

EXAMPLE 10

Examples of Parameter Sets for Mouse and Monkey Retinal Ganglion Cell Encoders

In this example we provide sets of parameters for two sample encoders: a mouse encoder and a monkey encoder. The parameter sets consist of spatial parameters, temporal parameters, and nonlinearity (spline) parameters. In addition, we provide the basis functions that are used to construct the temporal function (detailed in the section "Encoders" under the heading "Spatiotemporal Transformation Step").

Example Set of Encoder Parameters for a Mouse Ganglion Cell

Spatial parameters—each number is a weight at a location in space on the 10×10 grid. Each location on the grid is spaced by 2.6 degrees of visual angle. The sample weights below have been scaled by $10^3$ for readability.

$$Row_1 = \begin{bmatrix} 0.33002 & 0.04921 & 0.35215 & -0.50472 & -0.31662 \\ 0.48097 & 1.59118 & 0.25387 & -0.29734 & -0.65491 \end{bmatrix}$$

$$Row_2 = \begin{bmatrix} 0.72320 & -0.79947 & 1.11129 & -0.42650 & -0.10557 \\ -0.83933 & 1.09369 & -0.06499 & -0.22048 & 0.93292 \end{bmatrix}$$

$$Row_3 = \begin{bmatrix} 0.06408 & 0.11642 & 0.04056 & -1.00307 & 0.76165 \\ 0.40809 & -0.92745 & 0.80737 & 0.92201 & -0.12520 \end{bmatrix}$$

$$Row_4 = \begin{bmatrix} 0.48629 & 0.70789 & 0.15863 & 0.28964 & -0.12602 \\ -0.31769 & 0.29873 & -0.05653 & -0.13206 & 0.65947 \end{bmatrix}$$

$$Row_5 = \begin{bmatrix} 1.38570 & -0.92340 & -0.37912 & 1.43493 & -0.56229 \\ 0.33423 & 0.17084 & -0.21360 & 1.19797 & 2.19499 \end{bmatrix}$$

$$Row_6 = \begin{bmatrix} 0.06191 & -0.92478 & 0.56671 & 0.30621 & -0.52551 \\ 0.75282 & -1.19834 & 0.99852 & 1.59545 & 2.82842 \end{bmatrix}$$

$$Row_7 = \begin{bmatrix} -0.20276 & -1.03567 & 0.74796 & -0.59916 & 0.48170 \\ 0.31746 & 1.22590 & 1.52443 & 2.79257 & 1.82781 \end{bmatrix}$$

$$Row_8 = \begin{bmatrix} 0.31473 & 0.46495 & 0.51243 & 0.19654 & 0.91553 \\ 0.05541 & -0.80165 & 2.12634 & 1.46123 & 1.49243 \end{bmatrix}$$

$$Row_9 = \begin{bmatrix} -0.12374 & -1.08114 & 0.69296 & 0.03668 & -0.16194 \\ -0.02616 & 0.22097 & 0.79908 & -0.05111 & 0.54044 \end{bmatrix}$$

$$Row_{10} = \begin{bmatrix} 0.06479 & -0.00645 & -0.83147 & 0.10406 & 0.60743 \\ -0.87956 & 1.53526 & 0.02914 & 0.23768 & -0.13274 \end{bmatrix}$$

Temporal parameters—There are 10 temporal parameters. Each number is a weight for the 10 temporal basis functions (given next).

$$\begin{bmatrix} 11.84496 & -5.03720 & -42.79105 & -173.22514 & -172.80439 \\ 4.02598 & 186.79332 & 6.04702 & 50.69707 & -67.50911 \end{bmatrix}$$

Temporal basis functions—There are 10 temporal basis functions $\{F_1, F_2, \ldots F_{10}\}$. Each function has 18 values, where each value defines the basis function for a given timestep. The timesteps are spaced by 66.7 ms. The first value represents the function at a lag of 66.7 ms, and the last value represents the function at a lag of 1.2 s.

$$F_1 = [\,1\;\;0\;\;0\;\;0\;\;0\;\;0\;\;0\;\;0\;\;0\;\;0\;\;0\;\;0\;\;0\;\;0\;\;0\;\;0\;\;0\;\;0\,]$$

$$F_2 = [\,0\;\;1\;\;0\;\;0\;\;0\;\;0\;\;0\;\;0\;\;0\;\;0\;\;0\;\;0\;\;0\;\;0\;\;0\;\;0\;\;0\;\;0\,]$$

$$F_3 = [\,0\;\;0\;\;1\;\;0\;\;0\;\;0\;\;0\;\;0\;\;0\;\;0\;\;0\;\;0\;\;0\;\;0\;\;0\;\;0\;\;0\;\;0\,]$$

$$F_4 = [\,0\;\;0\;\;0\;\;1\;\;0\;\;0\;\;0\;\;0\;\;0\;\;0\;\;0\;\;0\;\;0\;\;0\;\;0\;\;0\;\;0\;\;0\,]$$

$$F_5 = [\,0\;\;0\;\;0\;\;0\;\;1\;\;0\;\;0\;\;0\;\;0\;\;0\;\;0\;\;0\;\;0\;\;0\;\;0\;\;0\;\;0\;\;0\,]$$

$$F_6 = \begin{bmatrix} 0 & 0 & 0 & 0 & 0 & 0.8958 & 0.4425 & 0.0418 \\ 0 & 0 & 0 & 0 & 0 & 0 & 0 & 0 & 0 \end{bmatrix}$$

$$F_7 = \begin{bmatrix} 0 & 0 & 0 & 0 & 0 & 0.3685 & 0.7370 & 0.5240 \\ 0.2130 & 0.0325 & 0 & 0 & 0 & 0 & 0 & 0 & 0 \end{bmatrix}$$

$$F_8 = \begin{bmatrix} 0 & 0 & 0 & 0 & 0 & 0 & 0.3038 & 0.5724 & 0.5724 \\ 0.4236 & 0.2469 & 0.1069 & 0.0250 & 0 & 0 & 0 & 0 & 0 \end{bmatrix}$$

$$F_9 = \begin{bmatrix} 0 & 0 & 0 & 0 & 0 & 0 & 0.0000 & 0.1420 & 0.3493 \\ 0.4696 & 0.4874 & 0.4336 & 0.3439 & 0.2457 \\ 0.1563 & 0.0852 & 0.0358 & 0.0081 \end{bmatrix}$$

$$F_{10} = \begin{bmatrix} 0 & 0 & 0 & 0 & 0 & 0 & 0 & 0.0195 \\ 0.1233 & 0.2465 & 0.3441 & 0.4012 & 0.4187 \\ 0.4043 & 0.3678 & 0.3181 & 0.2626 \end{bmatrix}$$

Note that the above numbers are not model parameters, i.e. they are not fitted to the data, but are chosen a priori. $F_1$ through $F_5$ are impulses, and $F_6$ through $F_{10}$ are raised cosines in logarithmic time, whose values are given here for the reader's convenience.

Spline parameters—the nonlinearity is a standard cubic spline, i.e. a piecewise cubic polynomial. As is standard, the spline is defined in terms of its constituent polynomials $\{P_1, P_2, \ldots P_6\}$ and knots $\{b_1, b_2, \ldots b_7\}$. Each $P_n$ is used to compute the nonlinearity between the pair of knots $b_n$ and $b_{n+1}$. Since here, the number of polynomials $p_{tot}=6$, there are $p_{tot}+1=7$ knots. Each polynomial $P$, is defined by 4 coefficients $[A_n, B_n, C_n, D_n]$. For a given point x, where $b_n \leq x \leq b_{n+1}$, the value of the nonlinearity y is found by:

$$y=((A_n(x-b_n)+B_n)(x-b_n)+C_n)(x-b_n)+D_n$$

For values of x that are less than $b_1$, the above formula is used with n=1. For values of x that are greater than $b_7$, the above formula is used with n=7.

$$\text{Knots: } \begin{bmatrix} -4.2105 & -2.6916 & -1.1727 \\ 0.3461 & 1.8650 & 3.3839 & 4.9027 \end{bmatrix}$$

$$P_1 = [0.2853 \quad -0.1110 \quad -2.9797 \quad 4.8119]$$
$$P_2 = [-0.2420 \quad 1.1890 \quad -1.3423 \quad 1.0298]$$
$$P_3 = [-0.2063 \quad 0.0863 \quad 0.5947 \quad 0.8860]$$
$$P_4 = [3.3258 \quad -0.8538 \quad -0.5712 \quad 1.2653]$$
$$P_5 = [-6.3887 \quad 14.3006 \quad 19.8527 \quad 10.0815]$$
$$P_6 = [3.2260 \quad -14.8100 \quad 19.0790 \quad 50.8402]$$

Example Set of Encoder Parameters for a Monkey Ganglion Cell

Spatial parameters—each number is a weight at a location in space on the 10×10 grid. Each location on the grid is spaced by 0.3 degrees of visual angle. The sample weights below have been scaled by $10^3$ for readability.

$$Row_1 = \begin{bmatrix} 0.55195 & -0.84156 & 0.84613 & -0.57117 & -0.19474 \\ -0.11197 & -1.00783 & -0.03454 & 1.28868 & -0.22166 \end{bmatrix}$$

$$Row_2 = \begin{bmatrix} -1.04227 & 0.23179 & 0.25551 & -0.45285 & -0.41161 \\ -0.15036 & 0.83755 & -1.57133 & -0.88564 & 2.05603 \end{bmatrix}$$

$$Row_3 = \begin{bmatrix} 0.60746 & 0.53720 & 0.60018 & -2.29069 & -1.81365 \\ -0.50460 & -1.29800 & -1.45387 & 1.58825 & -1.17287 \end{bmatrix}$$

$$Row_4 = \begin{bmatrix} -0.22411 & -0.77299 & -1.00706 & -1.94835 & -2.92171 \\ -2.98774 & -1.23428 & -0.54277 & 0.68372 & -0.70579 \end{bmatrix}$$

$$Row_5 = \begin{bmatrix} 0.06135 & 0.22591 & -3.75132 & -3.01549 & -2.58498 \\ -2.18981 & 0.13431 & -0.82007 & -1.10427 & -0.10170 \end{bmatrix}$$

$$Row_6 = \begin{bmatrix} 0.99720 & -0.02322 & 0.43823 & -0.52735 & -2.14156 \\ -2.89650 & -0.57703 & -0.87173 & 0.83669 & 1.35836 \end{bmatrix}$$

$$Row_7 = \begin{bmatrix} 0.13385 & 0.76995 & -0.80099 & -0.11574 & -1.70100 \\ -0.51437 & 0.29501 & -2.02754 & -0.22178 & -1.26073 \end{bmatrix}$$

$$Row_8 = \begin{bmatrix} -0.69551 & 1.30671 & -0.91948 & 0.15329 & 0.30121 \\ 0.20764 & -1.69209 & -0.09721 & -0.09431 & 0.36469 \end{bmatrix}$$

$$Row_9 = \begin{bmatrix} 0.26733 & -0.01433 & 0.57732 & 0.13921 & -0.18279 \\ 0.36743 & -0.59386 & 0.71287 & -1.03279 & 0.09482 \end{bmatrix}$$

$$Row_{10} = \begin{bmatrix} 1.17775 & -0.90456 & -1.58663 & -1.14128 & 0.00673 \\ 0.20418 & 0.98834 & -0.78054 & 0.43434 & 0.52536 \end{bmatrix}$$

Temporal parameters—There are 10 temporal parameters. Each number is a weight for the 10 temporal basis functions (given next).

$$\begin{bmatrix} 25.67952 & -43.25612 & 15.94787 & -84.80078 & -88.11922 \\ -4.70471 & -45.63036 & 73.07752 & 34.14097 & -0.95146 \end{bmatrix}$$

Temporal basis functions—There are 10 temporal basis functions $\{F_1, F_2, \ldots F_{10}\}$. Each function has 30 values, where each value defines the basis function for a given timestep. The timesteps are spaced by 16.7 ms. The first value represents the function at a lag of 16.7 ms, and the last value represents the function at a lag of 0.5 s.

$$F_1 = \begin{bmatrix} 1 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 \end{bmatrix}$$

$$F_2 = \begin{bmatrix} 0 & 1 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 \end{bmatrix}$$

$$F_3 = \begin{bmatrix} 0 & 0 & 1 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 \end{bmatrix}$$

$$F_4 = \begin{bmatrix} 0 & 0 & 0 & 1 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 \end{bmatrix}$$

$$F_5 = \begin{bmatrix} 0 & 0 & 0 & 0 & 1 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 \end{bmatrix}$$

$$F_6 = \begin{bmatrix} 0 & 0 & 0 & 0 & 0 & 0.8625 & 0.4952 & 0.1045 & 0 & 0 & 0 & 0 \\ 0 & 0 & 0 & 0 & 0 & 0 & 0 & 0 & 0 & 0 & 0 & 0 & 0 & 0 \\ 0 & 0 & 0 & 0 & 0 & 0 & 0 & 0 & 0 & 0 & 0 & 0 & 0 & 0 \end{bmatrix}$$

$$F_7 = \begin{bmatrix} 0 & 0 & 0 & 0 & 0 & 0.3396 & 0.6754 & 0.5612 & 0.3153 \\ 0.1180 & 0.0172 & 0 & 0 & 0 & 0 & 0 & 0 & 0 & 0 \\ 0 & 0 & 0 & 0 & 0 & 0 & 0 & 0 \end{bmatrix}$$

$$F_8 = \begin{bmatrix} 0 & 0 & 0 & 0 & 0 & 0.2309 & 0.4765 & 0.5415 & 0.4765 \\ 0.3562 & 0.2309 & 0.1266 & 0.0535 & 0.0125 & 0 & 0 \\ 0 & 0 & 0 & 0 & 0 & 0 & 0 & 0 & 0 \end{bmatrix}$$

-continued $$F_9 = \begin{bmatrix} 0 & 0 & 0 & 0 & 0 & 0 & 0 & 0.0753 & 0.2323 & 0.3583 \\ 0.4226 & 0.4312 & 0.4002 & 0.3461 & 0.3461 & 0.2819 & 0.2819 & & & \\ & & 0.2168 & 0.1567 & 0.1052 & 0.0639 & 0.0333 & & & \\ & & 0.0131 & 0.0024 & 0 & 0 & 0 & 0 & 0 & 0 \end{bmatrix}$$

$$F_{10} = \begin{bmatrix} 0 & 0 & 0 & 0 & 0 & 0 & 0 & 0.0004 & 0.0420 & 0.1189 \\ 0.1990 & 0.2656 & 0.3124 & 0.3386 & 0.3466 & 0.3398 & & & & \\ & & 0.3219 & 0.2962 & 0.2656 & 0.2326 & & & & \\ & & 0.1990 & 0.1662 & 0.1354 & 0.1071 & & & & \\ & 0.0820 & 0.0603 & 0.0420 & 0.0272 & 0.0158 & & & & \end{bmatrix}$$

Spline parameters—the nonlinearity is a standard cubic spline, i.e. a piecewise cubic polynomial. As is standard, the spline is defined in terms of its constituent polynomials $\{P_1, P_2, \ldots P_6\}$ and knots $\{b_1, b_2, \ldots b_7\}$. Each P, is used to compute the nonlinearity between the pair of knots $b_n$ and $b_{n+1}$. Since here, the number of polynomials $p_{tot}=6$, there are $p_{tot}+1=7$ knots. Each polynomial $P_n$ is defined by 4 coefficients $[A_n, B_n, C_n, D_n]$. For a given point x, where $b_n \leq x \leq b_{n+1}$, the value of the nonlinearity is found by:

$$y = ((A_n(x - b_n) + B_n)(x - b_n) + C_n)(x - b_n) + D_n$$

$$\text{Knots: } \begin{bmatrix} -7.9291 & -5.9389 & -3.9486 \\ -1.9584 & 0.0318 & 2.0221 & 4.0123 \end{bmatrix}$$

$$P_1 = [-1.0067 \quad 3.4136 \quad 4.5376 \quad -25.8942]$$

$$P_2 = [-0.2910 \quad -2.5970 \quad 6.1628 \quad -11.2780]$$

$$P_3 = [2.4072 \quad -4.3345 \quad -7.6326 \quad -11.5935]$$

$$P_4 = [-2.7537 \quad 10.0384 \quad 3.7195 \quad -24.9763]$$

$$P_5 = [1.6687 \quad -6.4032 \quad 10.9543 \quad 0.4804]$$

$$P_6 = [-1.0485 \quad 3.5605 \quad 5.2966 \quad 10.0743]$$

EXAMPLE 11

Monkey Retinal Ganglion Cell Firing Patterns Generated By the Encoders

Figure 13:
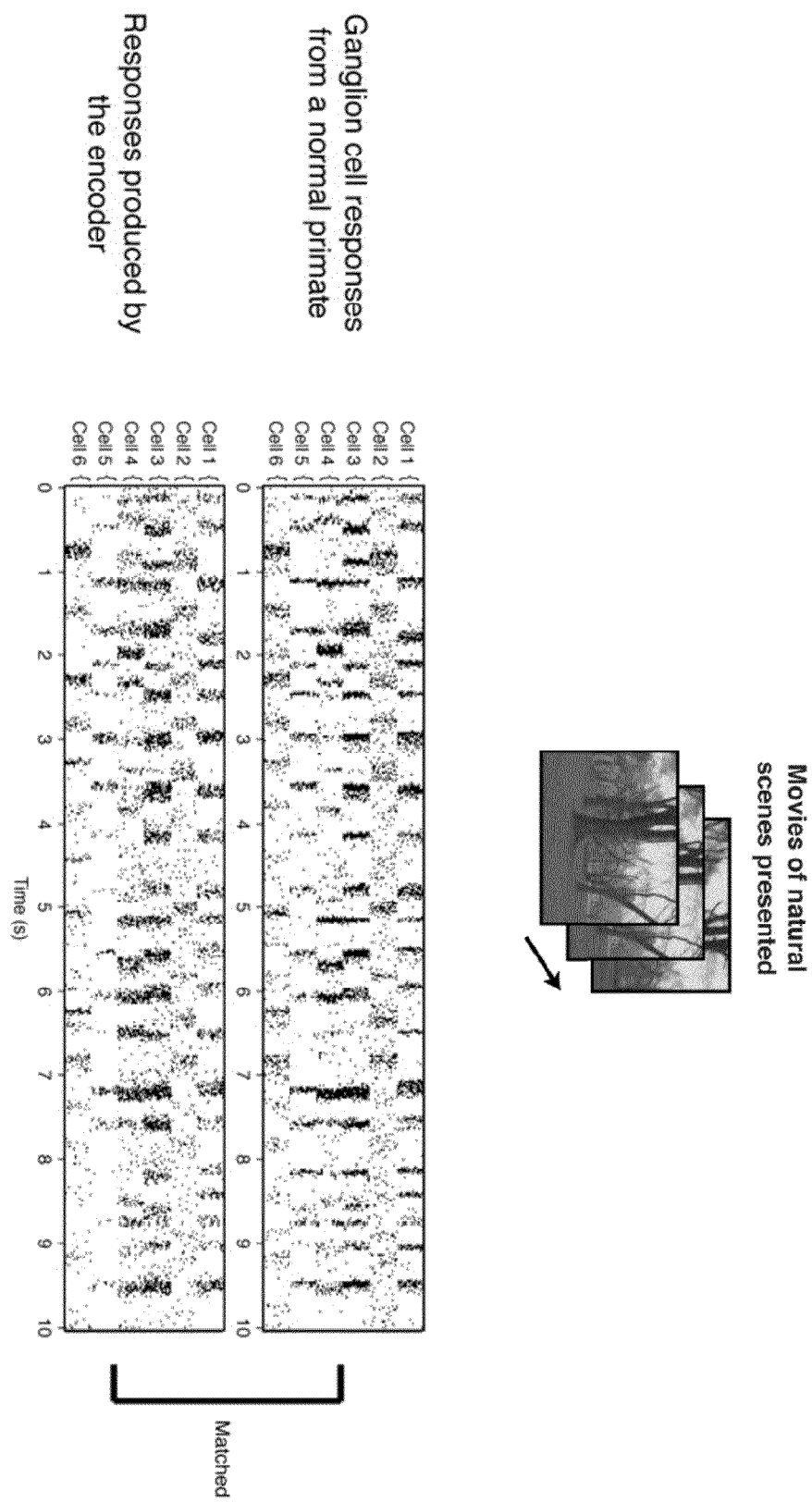
FIG. 13 shows that the responses produced by encoders generated from monkey retina to natural movies closely match those produced by normal monkey retina. Movies of natural scenes were presented to the normal monkey retina and the virtual retina. The top row shows spike trains from normal monkey ganglion cells; the bottom from their corresponding model cells (i.e., their encoders).

We presented movies of natural scenes and recorded ganglion cell responses of retinas taken from macaque monkeys (briefly: retinas were extracted from monkeys; the retinas were presented with movies of natural scenes, and ganglion cell responses were recorded) (FIG. 13 top). In addition, we presented the movies to encoders generated for these monkey ganglion cells (following the procedures outlined in the section "Encoders"). (FIG. 13 middle).

In the normal retinas, the movies are converted into patterns of action potentials, also referred to as spike trains, by the retinal circuitry. The spike trains from the normal retinas are shown in FIG. 13, top. The responses produced by the encoders closely match these responses (FIG. 13, middle). Thus, we were able to mimic normal retinal input/output relations.

EXAMPLE 12

Performance of the Monkey Encoders on a Visual Discrimination Task

Figure 14:
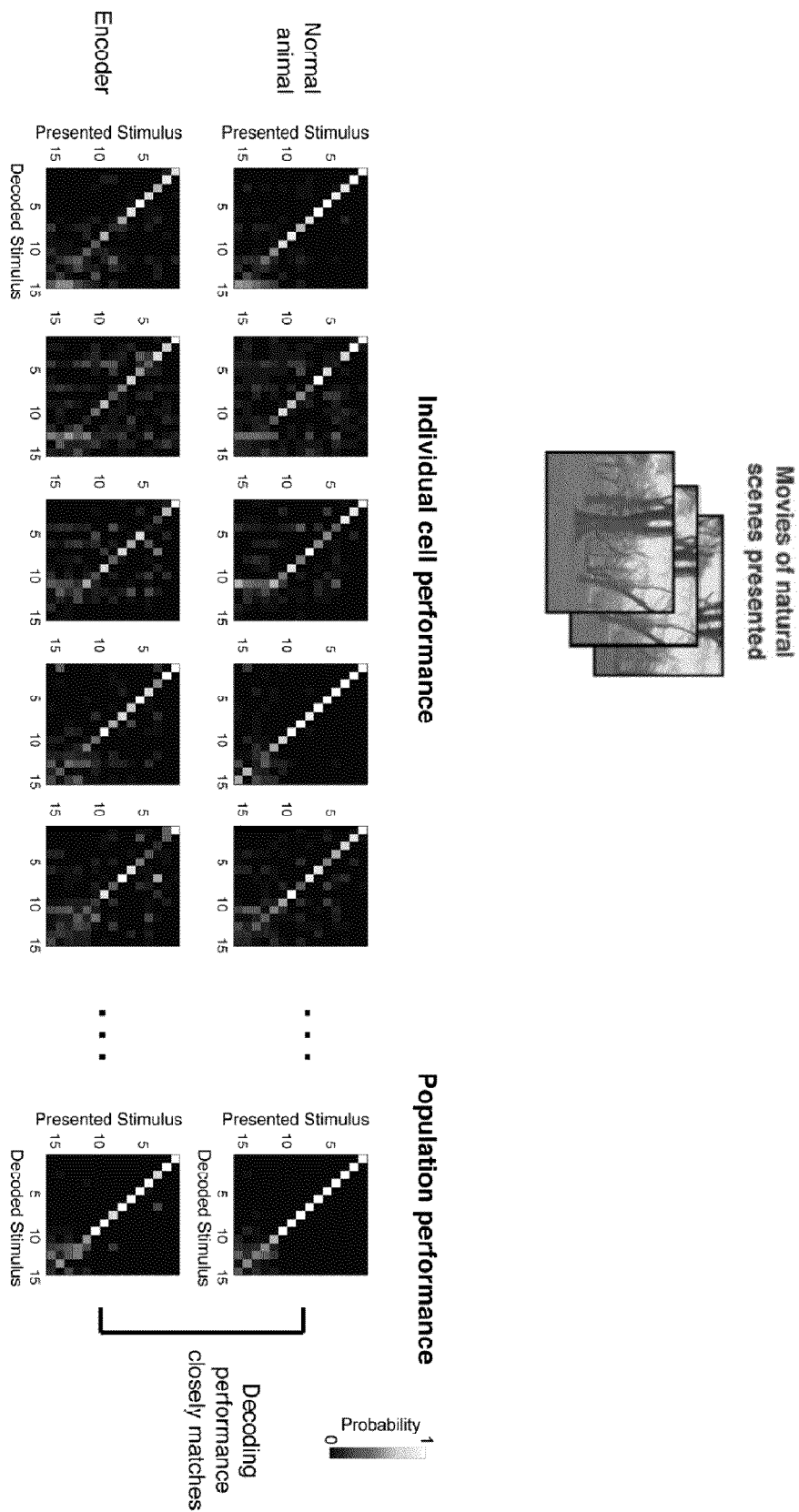
FIG. 14 shows that the performance of the monkey encoders on a visual discrimination task (same task as in FIG. 8) closely matches the performance of normal monkey ganglion cells. A. Confusion matrices generated when the testing set was obtained from the normal monkey retina. On the left are the matrices for individual ganglion cells, on the right, for a population of cells (10 cells). Fraction correct for the population was 83%. B. Confusion matrices generated when the testing set was obtained from the encoders that were generated from monkey ganglion cells. Fraction correct was 77%. All analysis was performed as Example 8, FIG. 8. Fraction correct using encoder responses was thus 92.8% of fraction correct using normal monkey ganglion cell responses.

We assessed the performance of a set of monkey encoders using a discrimination task method (FIG. 14). This task fol-lowed the method outlined in Example 8 (see section "Performance in a discrimination task").

Using the procedure outlined in Example 8, we performed 2 sets of analyses. For each one, we used the responses from the monkey retina for the training set. For the test sets, we used two sets of responses:

(1) The first set consisted of responses from the monkey retina. This is done to obtain the fraction correct produced by normal ganglion cell responses.

(2) The second set consisted of the responses from the encoders (the responses from the encoders are, as indicated throughout this document, streams of electrical pulses, in this case, spanning 1.33 sec after stimulus presentation, and binned with 66.7 ms, as are the monkey ganglion cell responses).

When we use the responses from the encoders as the test set, we obtain a measure of how well the encoders perform, given the response distributions of the monkey retina. In other words, we start with the assumption that the brain is built to interpret the responses of the monkey retina (i.e., the naturally encoded responses.) When we use the responses from the encoders as our test set, we obtain a measure of how well the brain would do with our proxy of the normal retinal responses (our proxy of the retina's code). The results are shown in FIG. 14. FIG. 14A shows the confusion matrixes generated when the test set was obtained from the monkey retina. On the left are the matrices for individual ganglion cells, on the right, for a population of cells (10 cells). As shown, the individual cells each carry a fair amount of information; together as a population, they can discriminate nearly all stimuli in the set. The fraction correct was 83%. FIG. 14B shows the confusion matrixes generated when the test set was obtained from the encoders (encoders built from the input/output relations of the monkey retina e.g., as shown in FIG. 14A). The fraction correct produced by the responses of the encoders, 77%, was extremely close to the fraction correct produced by the responses of the normal monkey ganglion cells, 83%. That is, it was 77/83=92.7% that of the fraction correct produced by the normal monkey ganglion cells. Thus, the encoders' output, that is, our proxy of the monkey retina's neural code, nearly matches the performance of the monkey retina.

EXAMPLE 13

Fidelity of Transducers' Output to Encoders' Output

Figure 15:
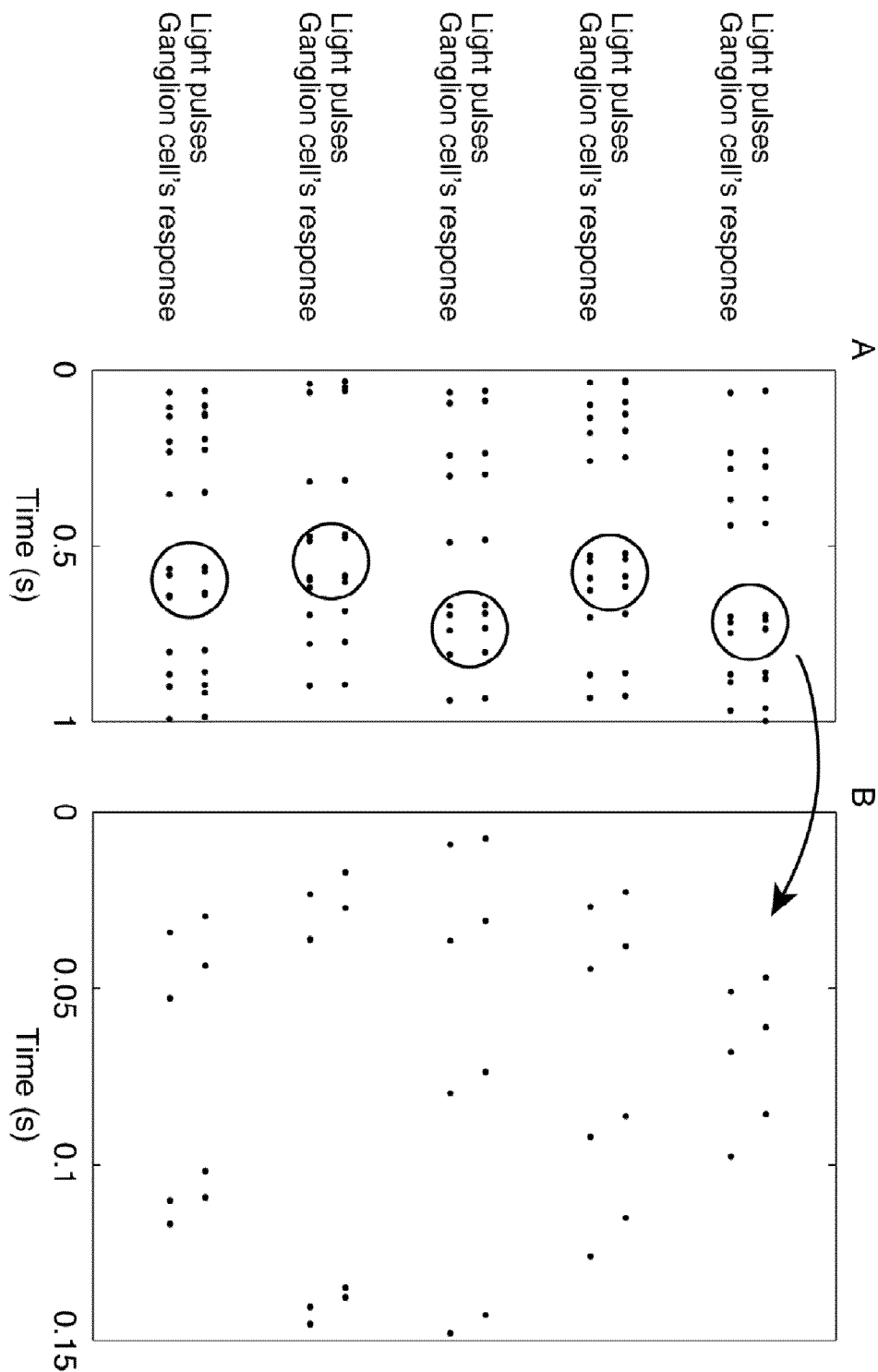
FIG. 15 shows that ganglion cell responses produced by the encoders+transducers follow the encoded output with high fidelity. The encoder's output was converted into a stream of light pulses, which were presented to a retina extracted from a doubly transgenic mouse that is blind and that expresses ChR2 in the ganglion cells. A. Light pulses and the corresponding ganglion cell output. For each pair of rows, the top row shows the times of the light pulses, while the bottom row shows the times of the action potentials produced by the ChR2-expressing ganglion cell. Each dot represents the occurrence of a light pulse or ganglion cell action potential. B. Expansion of the circled regions from (A), showing one-to-one correspondence between light pulses and action potentials. The action potentials followed the light pulses, and therefore, the encoder, with high fidelity.
Figure 16A:
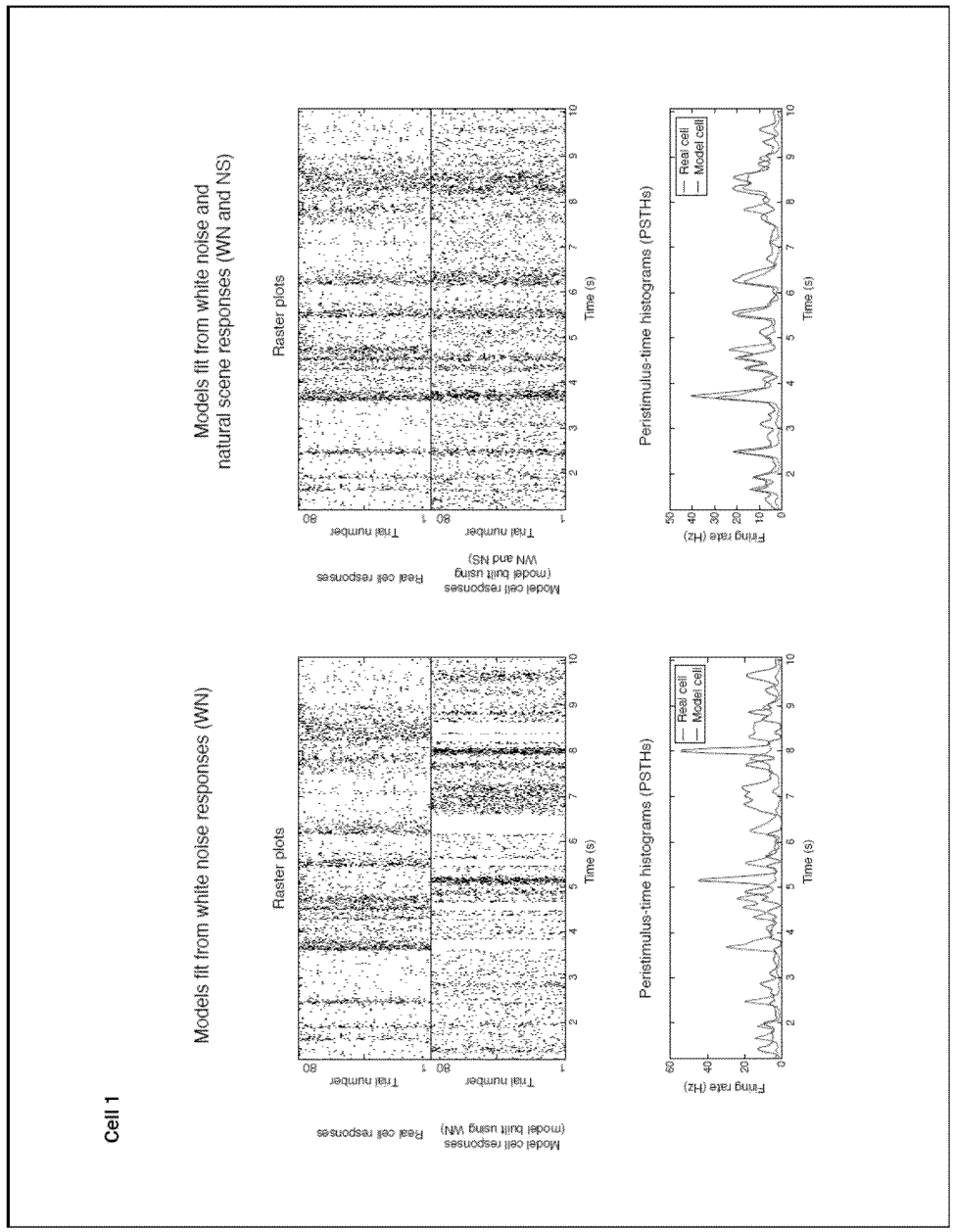
FIGS. 16A-16F illustrate the performance of a retinal encoder models when tested with movies of natural scenes, including landscapes, people walking, etc. In each figure, the performance of a conventional linear-nonlinear (LN) model is shown on the left, and the performance of the linear-nonlinear (LN) model of the type described in this application is shown on the right. Performance is shown via raster plots and peri-stimulus time histograms (PSTHs).
Figure 16B:
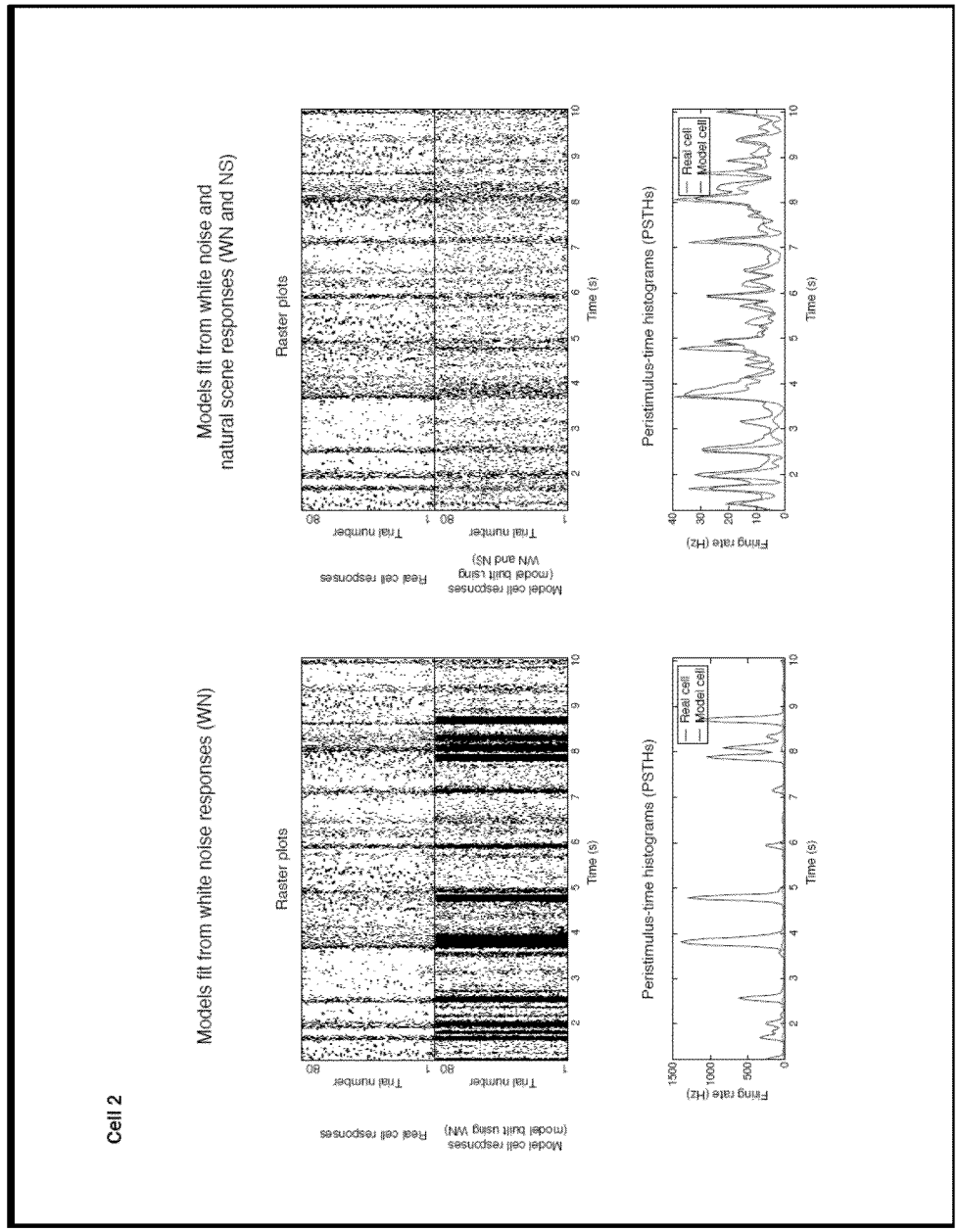
Figure 16C:
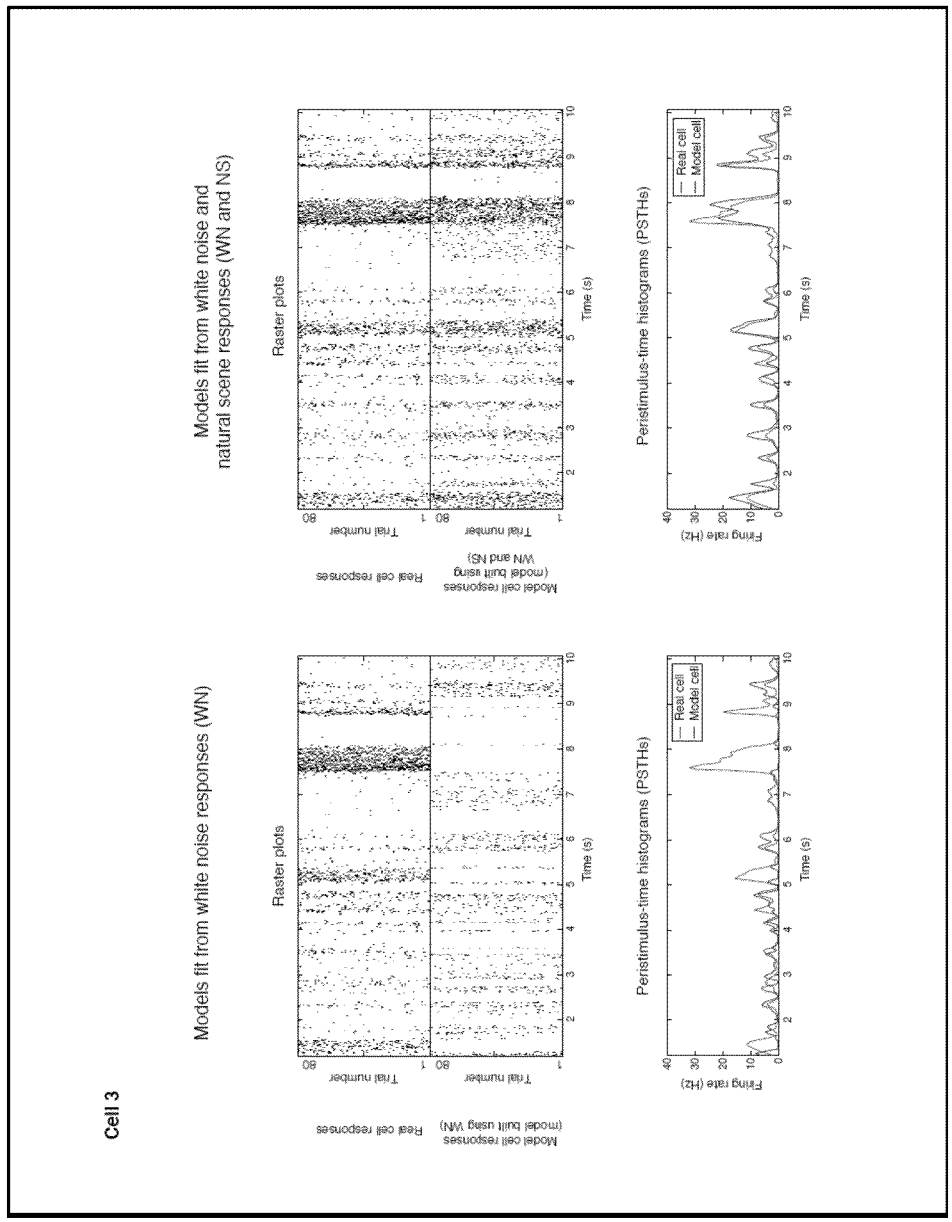
Figure 16D:
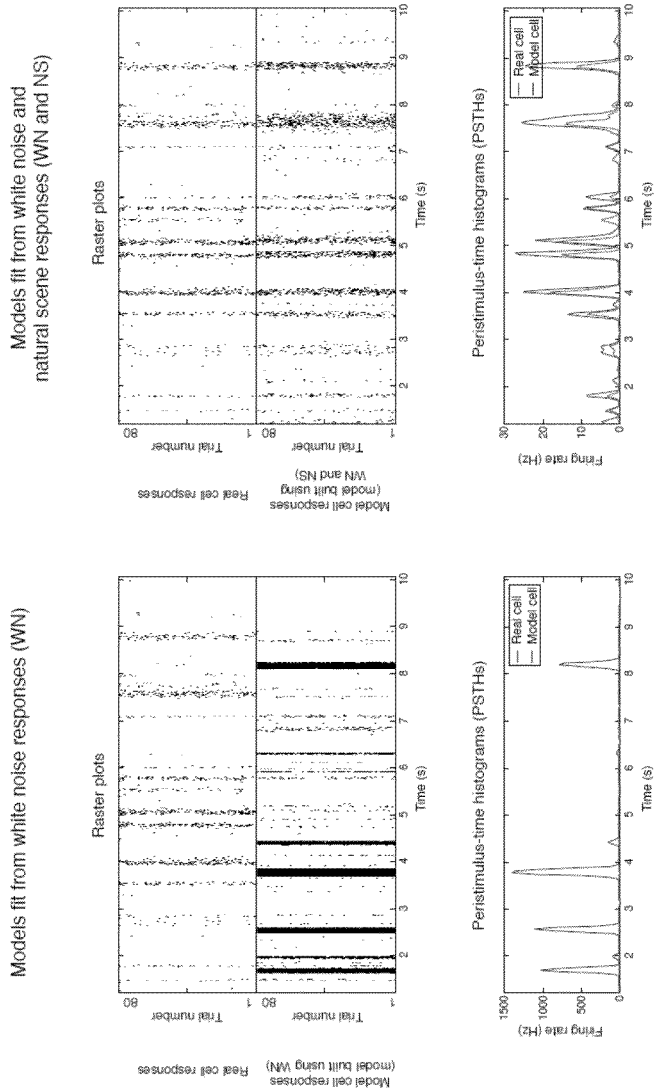
Figure 16E:
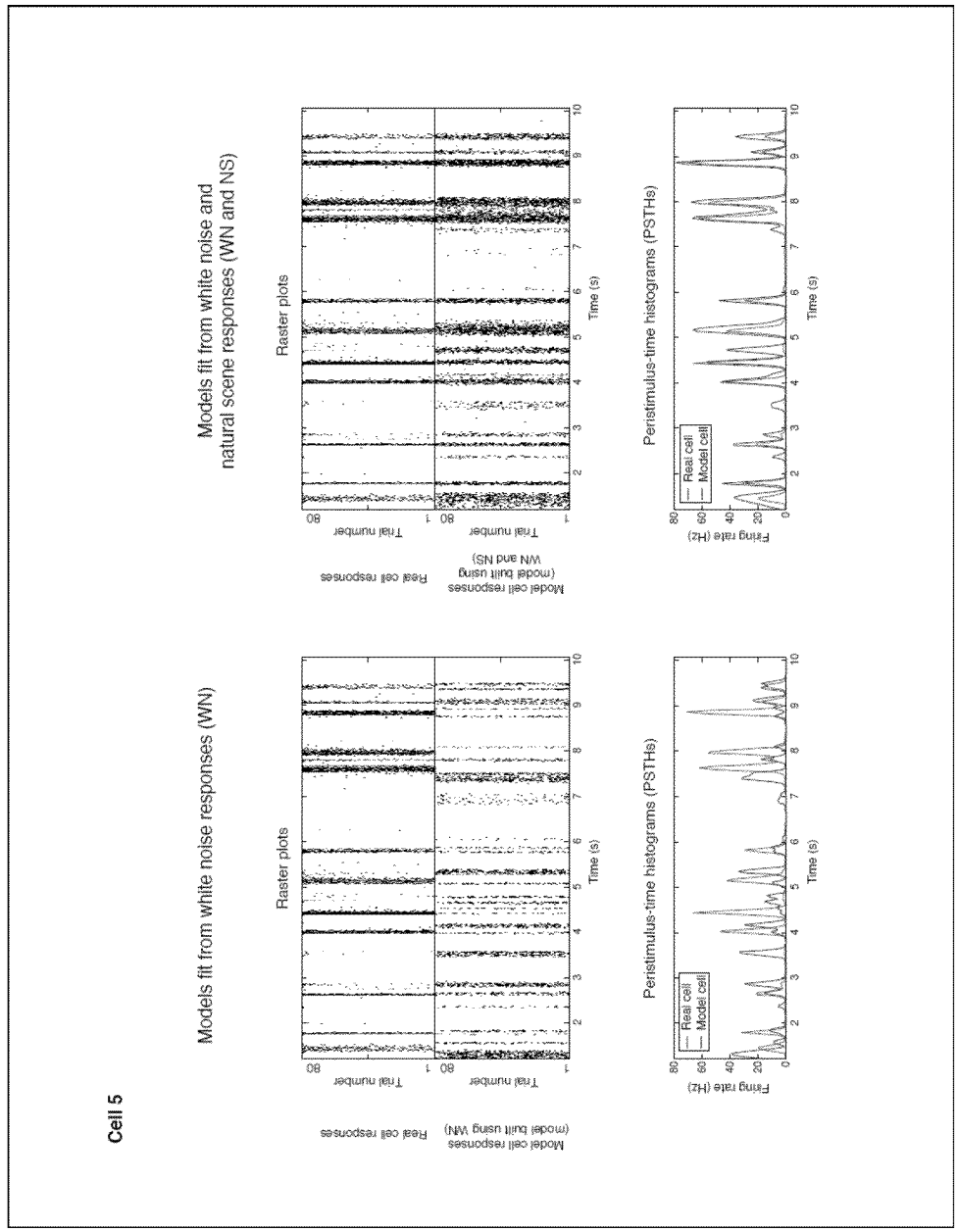
Figure 16F:
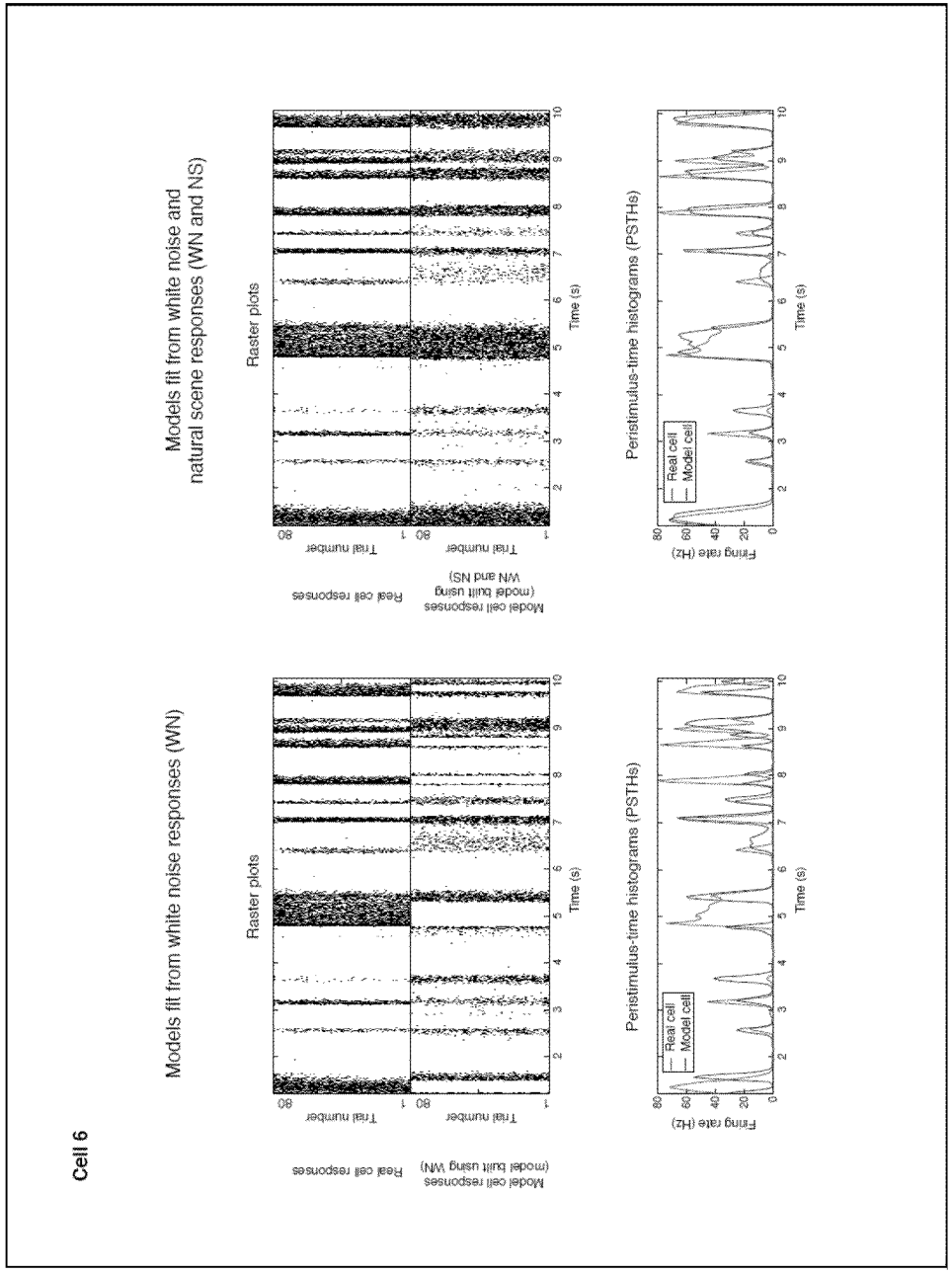

FIG. 15 shows that ganglion cell responses produced by the encoders+transducers follow the encoded output with high fidelity. An encoder was created as described above. A stimulus, an image of a baby's face, is input into a processing device running the encoder, and a code is generated. The code is put through an interface to drive an LED that is positioned above the retina, taken from a doubly transgenic mouse that is blind and that expresses ChR2. Electrodes record the retinal response. FIG. 15A shows the light pulses and the corresponding ganglion cell output. For each pair of rows, the top row shows the times of the light pulses, while the bottom row shows the times of the action potentials produced by the ChR2-expressing ganglion cell. FIG. 15B then shows an expansion of the circled regions from FIG. 15A, demonstrating one-to-one correspondence between light pulses and action potentials. As the figure shows, the action potentials can follow the light pulses, and therefore, the encoder, with high fidelity.

EXAMPLE 14

Treatment with Prosthetic

A male 53-year-old patient presents with macular degeneration. He is given the EVA test and scores a 48—his vision is 20/200 and he is diagnosed with low vision. His vision has been steadily worsening and he is concerned about becoming completely blind. The physician discusses treatment using the retinal prosthetic with the patient and it is decided to treat the patient with the retinal prosthetic of the invention.

A kit with the gene therapy drug as described above and the device having a camera, processor, and interface are used.

To reduce the risk of an ocular immune response to the treatment, the patient is administered a short course of glucocorticoids and an office visit is scheduled for the end of the course. During the office visit, gene therapy with a rAAV vector carrying a channelrhodopsin-2 cDNA, with promoter sequences targeting retinal ganglion cells is administered to the patient via intravitreal injection under local anesthetic.

The patient recovers and is sent home. There are weekly follow-up visits to ensure the eye heals properly and to monitor for dissemination of the viral vector. The eye heals normally and no dissemination is found.

On the fourth week, the patient is fitted for the first time with the hardware component of the treatment, which comprises a pair of glasses that include a processor and battery. Each lens of the glasses is a camera that records images; the inward-facing surface of each lens is a light array.

An initial visual acuity test is taken with and without the glasses device. The patient's vision without the glasses remains 20/200 with the therapeutic device it has already improved to 20/80 as measured with EVA. Each week the patient returns and is tested again and spends time practicing use of the complete device; by the sixth week vision with the glasses visual acuity has increased to 20/50. The patient has near-normal vision.

EXAMPLE 15

Treatment with the Prosthetic

A female, 60 year old patient presents with macular degeneration. She is given the EVA test and scores 3 letters—her vision is 20/800 and she is determined to be legally blind. The physician discusses treatment using the retinal prosthetic with the patient and it is decided to treat the patient with the retinal prosthetic of the invention.

A kit with the gene therapy drug and the device having a camera, processor, and interface are used.

To reduce the risk of an ocular immune response to the treatment, the patient is administered a short course of glucocorticoids and an office visit is scheduled for the end of the course. During the visit, gene therapy is administered to the patient via intravitreal injection under local anesthetic.

The patient recovers and is sent home. There are weekly follow-up visits to ensure the eye heals properly and to monitor for dissemination of the viral vectors. The eye heals normally and no dissemination is found.

On the fourth week, the patient is fitted for the first time with the hardware component of the treatment, which comprises a pair of glasses that include a processor and battery. Each lens of the glasses is a camera that records images; the inward-facing surface of each lens is a light array.

An initial visual acuity test is taken with and without the glasses device. The patient's vision without the glasses remains 20/800; with the therapeutic device it has already improved to 20/100 as measured by standard visual acuity tests. Each week the patient returns and is tested again and spends time practicing use of the complete device; by the sixth week vision with the glasses visual acuity has increased to 20/40.

EXAMPLE 15

Encoder Performance

FIGS. 16A-F illustrates the performance of retinal encoder models for various cells (cells 1-6, respectively) when tested with movies of natural scenes, including landscapes, people walking, etc. In each figure, the performance of a conventional linear-nonlinear (LN) model is shown on the left, and the performance of the linear-nonlinear (LN) model of the type described in this application is shown on the right. Performance is shown via raster plots and peri-stimulus time histograms (PSTHs). The conventional (LN) model was developed based only on the experimental response of retinal cells to a white noise stimulus. In contrast, the linear-nonlinear (LN) models of the type described in this application are developed based on recorded cell responses to both white noise and natural scene stimuli.

For the examples shown, the input test stimulus for both types of models is a movie of natural scenes, taken in Central Park in New York City. As shown, the standard LN model is not highly effective on natural scene stimuli: that is, this model, which is built using white noise stimuli, does not produce spike patterns that closely match those of the real cell. In contrast, the LN model described in this application, which is built using white noise and natural scene stimuli, is highly effective. The spike patterns it produces closely match those of the real cell. (Note that the natural scene movie used to test the models is different from that used to train the models, as is required for validating any model. Note also that in each figure, the same real cell is used as the basis for both types of models. Finally, note that performance of the encoder models of the type described herein has been demonstrated with a host of other stimuli, including movies, of faces, people walking, children playing, landscapes, trees, small animals, etc., as shown in the Prosthetic Application, and in Nirenberg, et al. Retinal prosthetic strategy with the capacity to restore normal vision, PNAS 2012 and the accompanying Supplementary Information section available at www.pnas.org/lookup/suppl/doi:10.1073/pnas.1207035109/-/DCSupplemental).

The same conclusions about performance can be drawn from the PSTHs. The light gray trace shows the average firing rate of the real cell; the dark grey trace shows the average firing rate of the model cell. The standard LN model misses many features of the firing rate; each of the different FIGS. 16A-16F, show examples of the different features missed by the standard model. The model described in this application, though, captures the features of the firing rates reliably and does so for an array of different cells (many other examples are shown in the herein).

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention and attached reference list. The citation and discussion of such references is provided merely to clarify the description of the present invention and is not an admission that any reference is prior art to the invention described herein. All references cited and discussed in this specification are incorporated herein by reference in their entirety.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

A computer employed to implement at least a portion of the functionality described herein may include a memory, one or more processing units (also referred to herein simply as "processors"), one or more communication interfaces, one or more display units, and one or more user input devices. The memory may include any computer-readable media, and may store computer instructions (also referred to herein as "processor-executable instructions") for implementing the various functionalities described herein. The processing unit(s) may be used to execute the instructions. The communication interface(s) may be coupled to a wired or wireless network, bus, or other communication means and may therefore allow the computer to transmit communications to and/or receive communications from other devices. The display unit(s) may be provided, for example, to allow a user to view various information in connection with execution of the instructions. The user input device(s) may be provided, for example, to allow the user to make manual adjustments, make selections, enter data or various other information, and/or interact in any of a variety of manners with the processor during execution of the instructions.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

As used herein, natural scene is to be understood to refer to an image of a natural environment, e.g., as described in Geisler WS Visual perception and the statistical of properties of natural scenes. Annu Rev. Psychol. 59:167-92 (2008). In some embodiments, natural scenes may be replaced with any suitable complex image, e.g., an image characterized by a spatial and/or temporal frequency power spectrum that generally conforms to a inverse frequency squared law. In some embodiments, e.g., where a short video clip is used, the spectrum of the complex image may deviate somewhat from the inverse square law. For example, in some embodiments, the complex image may have a spatial or temporal a power spectrum of the form $1/f^x$, where f is the frequency and x is in the range of, e.g., 1-3, or any subrange thereof (e.g. 1.5-2.5, 1.75-2.25, 1.9-2.1, etc.)

A white noise image refers to a noise image having a spatial frequency power spectrum that is essentially flat.

As used herein the term "light" and related terms (e.g. "optical", "visual") are to be understood to include electromagnetic radiation both within and outside of the visible spectrum, including, for example, ultraviolet and infrared radiation.

The indefinite articles "a" and "an," as used herein in the specification and in the claims, unless clearly indicated to the contrary, should be understood to mean "at least one."

The phrase "or," as used herein in the specification and in the claims, should be understood to mean "either or both" of the elements so conjoined, i.e., elements that are conjunctively present in some cases and disjunctively present in other cases. Multiple elements listed with "or" should be construed in the same fashion, i.e., "one or more" of the elements so conjoined. Other elements may optionally be present other than the elements specifically identified by the "or" clause, whether related or unrelated to those elements specifically identified. Thus, as a non-limiting example, a reference to "A or B", when used in conjunction with open-ended language such as "including" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "or" as defined above. For example, when separating items in a list, "or" or "or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

In the claims, as well as in the specification above, all transitional phrases such as "including," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

All definitions, as defined and used herein, should be understood to control over dictionary definitions, definitions in documents incorporated by reference, and/or ordinary meanings of the defined terms.

Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

REFERENCES

Ahuja A, Dorn J, Caspi A, McMahon M, Dagnelie G, Dacruz L, Stanga P, Humayun M, Greenberg R (2010) Blind subjects implanted with the Argus II retinal prosthesis are able to improve performance in a spatial-motor task. Br J Ophthalmol.

Arenkiel et al., In vivo light-induced activation of neural circuitry in transgenic mice expressing channelrhodopsin-2. *Neuron* (2007) 54(2): 205-18.

Ausubel et al., Current Protocols in Molecular Biology, John Wiley & Sons, New York, 1989

Bach, M et al (2008) Visual evoked potential-based acuity assessment in normal vision, artificially degraded vision, and in patients. Br J Ophthalmol 92:396-403

Barnstable et al., Thy-1 antigen: a ganglion cell specific marker in rodent retina. *Neuroscience* (1984) 11(4): 847-55.

Bi A, Cui J, Ma Y-P, Olshevskaya E, Pu M, Dizhoor A M, Pan Z-H (2006) Ectopic expression of a microbial-type rhodopsin restores visual responses in mice with photoreceptor degeneration. Neuron 50:23-33.

Bomash I, Roudi Y, Nirenberg S. (2010) A virtual retina that works on a broad array of stimuli including natural scenes: A tool to simplify the problem of population coding. *Society for Neuroscience*. Program No. 891.5.

Bookstein R et al (1990) Promoter deletion and loss of retinoblastoma gene expression in human prostate carcinoma. Proc. Nati. Acad. Sci. USA 87 (19):7762-7766

Busskamp V, et al (2010) Genetic reactivation of cone photoreceptors restores visual responses in retinitis pigmentosa. Science 329:413-417.

Cai et al. (2010) Gene delivery to mitotic and postmitotic photoreceptors via compacted DNA nanoparticles results in improved phenotype in a mouse model of retinitis pigmentosa. *FASEB J.* 24: 1178-1191.

Campagnola L, Wang H, Zylka M J. (2008) Fiber-coupled light-emitting diode for localized photostimulation of neurons expressing channelrhodopsin-2. Journal of Neuroscience Methods. 169:27-33.

Cardin J A, et al (2010) Targeted optogenetic stimulation and recording of neurons in vivo using cell-type-specific expression of Channelrhodopsin-2. Nat Protoc 5(2): 247-54.

Chader G J, Weiland J, Humayun M S (2009) Artificial vision: needs, functioning, and testing of a retinal electronic prosthesis. Prog Brain Res 175:317-332.

Chiappa, K. (1997) Evoked Responses in Clinical Medicine, Third Edition, Lippincott-Raven Chichilnisky E J. (2001) A simple white noise analysis of neuronal light responses. Network 12(2): 199-213

Chopdar A, Chakravarthy U, Verma D (2003) Age related macular degeneration. BMJ 326:485-488.

Cover T and Thomas J. (2006) Elements of Information Theory, 2nd Edition. Hoboken, N.J.: Wiley Dann J F, Buhl E H. (1987) Retinal ganglion cells projecting to the accessory optic system in the rat. J Comp Neurol 262(1): 141-58.

Dedek K, et al (2008) Ganglion cell adaptability: does the coupling of horizontal cells play a role?PLoS One. 3(3): e1714.

Douglas R M et al (2005) Independent visual threshold measurements in the two eyes of freely moving rats and mice using a virtual-reality optokinetic system. Vis Neurosci. 22(5):677-84.

Duda R O, Hart P E (2001) Pattern Classification (2nd Edition) Wiley, NY,

Enroth-Cugell et al., (1966) The contrast sensitivity of retinal ganglion cells of the cat. J Physiol 187(3): 517-52.

European Patent Application No. 19891976

Famulare M, Fairhall A. (2010) Feature selection in simple neurons: how coding depends on spiking dynamics. Neural Comput 22(3): 581-98

Field et al., (2007) Information processing in the primate retina: circuitry and coding. Annu Rev Neurosci 30: 1-30.

Fitzgerald et al. (1994) Retinal signal transmission in Duchenne muscular dystrophy. J Clin Invest 93: 2425-30.

Foley J M, Legge GE (1981) Contrast detection and near-threshold discrimination in human vision. Vision Res. 21(7):1041-53.

Fried S, Werblin F, McMahon M J (2006) US Pat. 2006/0129207 Mimicking neural coding in retinal ganglion cells with short pulse electrical stimulation. In: (US, ed).

Friedman DS, O'Colmain B J, Muñoz B, Tomany S C, McCarty C, de Jong P T V M, Nemesure B, Mitchell P, Kempen J, Eye Diseases Prevalence Research Group (2004) Prevalence of age-related macular degeneration in the United States. Arch Ophthalmol 122:564-572.

Gerding H, Benner F P, Taneri S (2007) Experimental implantation of epiretinal retina implants (EPI-RET) with an IOL-type receiver unit. J Neural Eng 4:S38-49.

Giolli R A, Blanks R H I, Lui F. (2005) The accessory optic system: basic organization with an update on connectivity, neurochemistry, and function. Prog Brain Res 151: 407-40.

Golan L, Reutsky I, Farah N & Shoham S. (2009) Design and characteristics of holographic neural photo-stimulation systems, Journal of Neural Engineering 6 066004, (2009)

Graham-Rowe D (2009) A Brighter Future for Retinal Implants. In: Technology Review, http://www.technology-review.com/biomedicine/23539/. Boston, Mass.: MIT.

Grinstead C M and Snell J L (1997) Introduction to Probability. American Mathematical Society; 2nd Revised edition Grossman N, Poher V, Grubb M S, Kennedy G T, Nikolic K, McGovern B, Palmini R B, Gong Z, Drakakis E M, Neil, M A A, Dawson M D, Burrone J, Degenaar P. (2010) Multi-site optical excitation using ChR2 and micro-LED array. J. Neural Eng, 7(1):1-13.

Han et al, (2009), Millisecond-Timescale Optical Control of Neural Dynamics in the Nonhuman Primate Brain, Neuron 62, 191-198.

Hand DJ. (1981) Discrimination and classification. Wiley Series in Probability and Mathematical Statistics.

Huberman A D, Manu M, Koch S M, Susman M W, Lutz A B, Ullian E M, Baccus S A, Barres B A (2008) Architecture and activity-mediated refinement of axonal projections from a mosaic of genetically identified retinal ganglion cells. Neuron. 2008 Aug. 14; 59(3):425-38.

Huberman A D, Wei W, Elstrott J, Stafford B K, Feller M B, Barres B A (2009) Genetic Identification of an On-Off Direction-Selective Retinal Ganglion Cell Subtype Reveals a Layer-Specific Subcortical Map of Posterior Motion. Neuron. 62(3):327-334.

Izhikevich EM (2007) Dynamical systems in neuroscience: the geometry of excitability and bursting. Cambridge, Mass.: MIT Press Izhikevich EM (2010) Hybrid spiking models. Review. Phil. Trans. R. Soc. A (2010) 368, 5061-5070

Jacobs A L et al (2009), Ruling out and ruling in neural codes. Proc Natl Acad Sci USA. 106(14):5936-41.

Jeffreys, Harold (1961). The Theory of Probability. The Oxford University Press.

Kass R E, Ventura V, Brown E N. (2005) Statistical issues in the analysis of neuronal data. J Neurophysiol 94(1): 8-25.

Kawasaki et al., Variability of the relative afferent pupillary defect. Am J Ophthalmol (1995). 120: 622-633.

Kay M A, Glorioso J C, Naldini L. (2001) Viral vectors for gene therapy: the art of turning infectious agents into vehicles of therapeutics. Nat Med. 7(1):33-40. Review.

Kelly S, Shire D, Chen J, Doyle P, Gingerich M, Drohan W, Theogarajan L, Cogan S, Wyatt J, Rizzo J I (2009) Realization of a 15-channel, hermetically-encased wireless subretinal prosthesis for the blind. In, pp 200-203.

Kibbel S, Harscher A, Wrobel W-G, Zrenner E, Rothermel A (2009) Design and Performance of an improved active subretinal chip. In: World Congress on Medical Physics and Biomedical Engineering, Sep. 7-12, 2009, Munich, Germany (Kim S I, Suh T S, Dössel O, Schlegel W C, eds), pp 192-195: Springer Berlin Heidelberg.

Koilkonda R D, Hauswirth W W, Guy J. (2009) Efficient expression of self-complementary AAV in ganglion cells of the ex vivo primate retina. Mol Vis. 15:2796-802.

Kuffler SW. (1953) Discharge patterns and functional organization of mammalian retina. J Neurophysiol 16(1): 37-68.

Lagali P S, Balya D, Awatramani G B, Münch T A, Kim D S, Busskamp V, Cepko C L, Roska B (2008) Light-activated channels targeted to ON bipolar cells restore visual function in retinal degeneration. Nat Neurosci 11:667-675.

Lesica NA et al. (2007) Adaptation to stimulus contrast and correlations during natural visual stimulation. Neuron 55(3): 479-491.

Lettvin et al., (1959) What the frog's eye tells the frog's brain. Proceedings of the Institute of Radio Engineers 47(11): 1940-51.

Liao et al. (2007) In vivo gene delivery in the retina using polyethylenimine. BioTechniques 2007, 42:285-288.

Loewenstein J I, Montezuma S R, Rizzo J F, III (2004) Outer Retinal Degeneration: An Electronic Retinal Prosthesis as a Treatment Strategy. Arch Ophthalmol 122:587-596.

Maguire et al. Safety and efficacy of gene transfer for Leber's congenital amaurosis. N Engl J Med (2008) 358: 2240-2248.

Mancuso et al., (2009) Gene therapy for red-green colour blindness in adult primates. Nature 461(7265): 784-7.

Martin et al. 2002. Gene delivery to the eye using adeno-associated viral vectors. *Methods* 28:267-275.

McGowan M H et al (1998) Characterization of the Mouse Aldose Reductase Gene and Promoter in a Lens Epithelial Cell Line. Mol Vis 1998; 4:2

McLaughlin S K, Collis P, Hermonat P L, Muzyczka N. (1988) Adeno-associated virus general transduction vectors: analysis of proviral structures. J Virol. 62(6):1963-73.

Meytlis M, Bomash I, Pillow J W, Nirenberg S. (2009) Assessing the importance of correlated firing using large populations of neurons. *Society for Neuroscience*. Program No. 165.3.

Morgans C W, et al (2009) TRPM1 is required for the depolarizing light response in retinal ON-bipolar cells. Proc Natl Acad Sci USA 106(45): 19174-8.

Nanduri D, Humayun M, Greenberg R, McMahon M, Weiland J (2008) Retinal prosthesis phosphene shape analysis. In: 30th Annual International Conference of the IEEE Engineering in Medicine and Biology Society, pp 1785-1788. Vancouver, BC.

Nichols Z, Meytlis M, Nirenberg S. (2010) Correlations play a negligible role in coding white noise and natural scene stimuli in complete retinal populations. *Submitted*.

Nirenberg S (2000) Photoablation of cells expressing beta-galactosidase. *Methods Mol Biol*. 135:475-80

Nirenberg S and Cepko, C (1993). Targeted ablation of diverse cell classes in the nervous system in vivo. *J Neurosci*. 13(8):3238-51.

Nirenberg S and Latham PE. (1998) Population coding in the retina. *Curr. Opin. Neurobiol*. 8(4):488-493

Nirenberg S and Meister M. (1997). The light response of retinal ganglion cells is truncated by a displaced amacrine circuit. Neuron 18:637-650

Nirenberg S et al (2001) Retinal ganglion cells act largely as independent encoders. Nature 411(6838):698-701.

Nirenberg S et al. (2010) Heterogeneous response dynamics in retinal ganglion cells: the interplay of predictive coding and adaptation. *J Neurophysiol* 103(6): 3184-94

Norcia, AM, and Tyler, CW (1985) Spatial frequency sweep VEP: visual acuity during the first year of life. Vision Res. 25(10):1399-408

Norcia, AM, et al (1989). Measurement of spatial contrast sensitivity with the swept contrast VEP. Vision Res. 1989; 29(5):627-37.

Pandarinath et al (2010a) A novel mechanism for switching a neural system from one state to another. Front Comput Neurosci. 31; 4:2.

Pandarinath et al (2010b) Symmetry breakdown in the ON and OFF pathways of the retina at night: functional implications. J Neurosci 30(30): 10006-14.

Paninski L, Pillow J, Lewi J. (2007) Statistical models for neural encoding, decoding, and optimal stimulus design. Prog Brain Res. 165:493-507.

Paninski L. (2004) Maximum likelihood estimation of cascade point-process neural encoding models. *Network* 15(4): 243-62

Panzeri S, et al (2007) Correcting for the sampling bias problem in spike train information measures. J. Neurophysiol. 98(3):1064-72. Review.

Pelli D G, Robson J G, & Wilkins A J (1988) The design of a new letter chart for measuring contrast sensitivity. Clinical Vision Sciences 2, 187-199

Perry V H, Silveira L C. (1988) Functional lamination in the ganglion cell layer of the macaque's retina. Neuroscience. 25(1):217-23.

Petrs-Silva et al., (2009) High-efficiency transduction of the mouse retina by tyrosine-mutant AAV serotype vectors. Mol Ther 17(3): 463-71.

Petersen-Jones et al., (2009) AAV retinal transduction in a large animal model species: comparison of a self-complementary AAV2/5 with a single-stranded AAV2/5 vector. Mol Vis 15: 1835-42.

Pillow J W, Shlens J, Paninski L, Sher A, Litke A M, Chichilnisky E J, Simoncelli EP. (2008) Spatio-temporal correlations and visual signalling in a complete neuronal population. Nature 454(7207): 995-9

Prusky G T, et al (2004) Rapid quantification of adult and developing mouse spatial vision using a virtual optomotor system. Invest Ophthalmol Vis Sci. 45(12):4611-6.

Published PCT Application WO 1996013598
Published PCT application WO 1998048027
Published PCT Application WO2000015822
Published PCT application WO2001094605
Published PCT application WO2002082904
Published PCT application WO2003047525
Published PCT application WO2003080648
Published PCT application WO2003093479
Published PCT application WO2003104413
Published PCT application WO2005080573
Published PCT application WO2007127428
Published PCT application WO2010011404

Pun L (1969), *Introduction to Optimization Practice*, ISBN 471-70233-1

Purpura K, Tranchina D, Kaplan E, Shapley RM. (1990) Light adaptation in the primate retina: analysis of changes in gain and dynamics of monkey retinal ganglion cells. Vis Neurosci 4(1): 75-93.

Rolls E T, Baylis G C, Leonard C M. Role of low and high spatial frequencies in the face-selective responses of neurons in the cortex in the superior temporal sulcus in the monkey. Vision Res. 1985; 25(8):1021-35.

Sambrook et al, "Molecular Cloning. A Laboratory Manual", 2d ed., Cold Spring Harbor Laboratory, New York (1989)

Sauer B. (1987) Functional expression of the cre-lox site-specific recombination system in the yeast Saccharomyces cerevisiae. Mol Cell Biol. 7(6):2087-96.

Shapley R M, Victor JD. (1981) How the contrast gain control modifies the frequency responses of cat retinal ganglion cells. J Physiol. 318:161-79.

Sharpee T O et al. (2008) On the Importance of Static Non-linearity in Estimating Spatiotemporal Neural Filters With Natural Stimuli. J Neurophysiol 99(5): 2496-509

Sheridan C (2011) Gene Therapy finds its niche Nature Biotechnology 29(2): 121-128 Siegert S, Scherf B G, Punta K D, Didkovsky N, Heintz N, Roska B (2009). Genetic address book for retinal cell types. *Nature Neuroscience*. 12:1197-1204.

Simoncelli et al. (2004) Characterization of neural responses with stochastic stimuli. The cognitive neurosciences: 327-38

Simonelli et al. (2010) Gene Therapy for Leber's Congenital Amaurosis is Safe and Effective Through 1.5 Years After Vector Administration, *Molecular Therapy* 18 3, 643-650.

Sinclair J R, et al (2004). Selective ablation of a class of amacrine cells alters spatial processing in the retina. J Neurosci. 24(6):1459-67.

Soucy E R et al. (1998) A novel signaling pathway from rod photoreceptors to ganglion cells in mammalian retina. *Neuron* 21:481-493

Stone et al., (1993) Response properties of ganglion cells in the isolated mouse retina. Vis Neurosci 10(1): 31-9.

Strong S P, et al (1998) On the application of information theory to neural spike trains. Pac Symp Biocomput. 621-32.

Thyagarajan S, van Wyk M, Lehmann K, Löwel S, Feng G, Wässle H (2010) Visual function in mice with photoreceptor degeneration and transgenic expression of channelrhodopsin 2 in ganglion cells. J Neurosci 30:8745-8758.

Tomita H, Sugano E, Isago H, Hiroi T, Wang Z, Ohta E, Tamai M (2010) Channelrhodopsin-2 gene transduced into retinal ganglion cells restores functional vision in genetically blind rats. Exp Eye Res 90:429-436.

Troy J B, Bohnsack D L, Chen J, Guo X, Passaglia C L. (2005) Spatiotemporal integration of light by the cat X-cell center under photopic and scotopic conditions. Vis Neurosci 22(4): 493-500.

Troy J B, Bohnsack D L, Diller L C. (1999) Spatial properties of the cat X-cell receptive field as a function of mean light level. Vis Neurosci 16(6): 1089-104.

Turchinovich et al. (2010) Non-viral siRNA delivery into the mouse retina in vivo. *BMC Ophthalmology* 10:25.

U.S. Pat. No. 7,149,586
U.S. Pat. No. 5,856,152
U.S. Pat. No. 5,871,982
U.S. Pat. No. 6,533,798
U.S. Patent Publication 20080221653
U.S. Patent Publication 20080249588
U.S. Patent Publication 20090088399
U.S. Patent Publication 20090326623,
U.S. Patent Publication 20100272688
U.S. Patent Publication Nos. 20070261127

Ueda et al, (1997) The mGluR6 5' upstream transgene sequence directs a cell-specific and developmentally regulated expression in retinal rod and ON-type cone bipolar cells. *J Neurosci.* 17(9):3014-23.

van Adel et al. (2003) Delivery of ciliary neurotrophic factor via lentiviral-mediated transfer protects axotomized retinal ganglion cells for an extended period of time. *Hum. Gene Ther.* 14:103-115.

Victor J D, Shapley R M. (1979) The nonlinear pathway of Y ganglion cells in the cat retina. J Gen Physiol. 74(6):671-89.

Victor JD. (1987) The dynamics of the cat retinal X cell centre. *The Journal of Physiology* 386(1): 219.

Walther W, Stein U. (2000) Viral vectors for gene transfer: a review of their use in the treatment of human diseases. Drugs. 60(2):249-71. Review.

Wassle H. (2004) Parallel processing in the mammalian retina. Nat Rev Neurosci 5(10): 747-57.

Wells et al. (2005) Optical stimulation of neural tissue in vivo. Optics Letters 30(5):504-506, Winter J O, Cogan S F, Rizzo J F I (2007) Retinal prostheses: current challenges and future outlook. J Biomater Sci Polym Ed 18:1031-1055.

Wright AF. (1997) Gene therapy for the eye. Br J Ophthalmol 81(8): 620-623 Review.

Yonehara K, Ishikane H, Sakuta H, Shintani T, Nakamura-Yonehara K, et al. (2009) Identification of Retinal Ganglion Cells and Their Projections Involved in Central Transmission of Information about Upward and Downward Image Motion. PLoS ONE 4(1): e4320.

Yonehara K, Shintani T, Suzuki R, Sakuta H, Takeuchi Y, et al. (2008) Expression of SPIG1 Reveals Development of a Retinal Ganglion Cell Subtype Projecting to the Medial Terminal Nucleus in the Mouse. PLoS ONE 3(2): e1533.

Zhang Y, Ivanova E, Bi A, Pan Z-H (2009) Ectopic expression of multiple microbial rhodopsins restores ON and OFF light responses in retinas with photoreceptor degeneration. J Neurosci 29:9186-9196.

Zrenner E, et al (2009) Subretinal Microelectrode Arrays Allow Blind Retinitis Pigmentosa Patients to Recognize Letters and Combine them to Words. BMEI '09. 2nd International Conference on Biomedical Engineering and Informatics. Issue Date: 17-19 Oct. 2009. ISBN: 978-1-4244-4132-7. Pages 1-4.

What is claimed is:

1. A method comprising:
receiving, by a processing device, raw image data corresponding to a series of raw images; and
processing the raw image data with an encoder of the processing device to generate encoded data, wherein the encoder is characterized by an input/output transformation that substantially mimics the input/output transformation of at least one retinal cell a vertebrate retina;
wherein the processing the raw image data comprises applying a spatiotemporal transformation to a set of images to generate a set of retinal response values, and wherein the applying the spatiotemporal transformation further comprises:
applying a spatiotemporal kernel to the set of images to generate spatially-temporally transformed images; and
applying a nonlinear function to the spatially-temporally transformed images to generate the set of retinal response values;
generating the encoded data based on the set of retinal response values; and
activating a high resolution signaling device according to the encoded data.

2. The method of claim 1, wherein processing the raw image data with an encoder to generate encoded data comprises:
processing the raw image data to generate a plurality of values, X,
transforming the plurality of X values into a plurality of response values, $\lambda_m$, indicative of a corresponding response of a retinal cell in the retina, m, and generating the encoded data based on the response values.

3. The method of claim 2, wherein the response values correspond to retinal cell firing rates.

4. The method of claim 3, wherein the response values correspond to a function of the retinal cell firing rates.

5. The method of claim 3, wherein the response values correspond to retinal cell output pulses.

6. The method of claim 3, wherein the response values correspond to retinal cell generator potential.

7. The method of claim 1, wherein processing the raw image data with an encoder to generate encoded data comprises:
receiving images from the raw image data and, for each image, rescaling the luminance or contrast to generate a rescaled image stream;
receiving a set of N rescaled images from the rescaled image stream and applying the spatiotemporal transformation to the set of N images to generate the set of retinal response values, each value in the set corresponding to a respective one of the retinal cells.

8. The method of claim 7, wherein the response values comprise retina cell firing rates.

9. The method of claim 7 wherein N is at least 5.

10. The method of claim 7 wherein N is at least 20.

11. The method of claim 7, wherein applying the spatiotemporal kernel comprises:

convolving of the N rescaled images with the spatiotemporal kernel to generate N spatially-temporally transformed images.

12. The method of claim 11, wherein applying the spatiotemporal kernel comprises:
   convolving the N rescaled images with a spatial kernel to generate N spatially transformed images;
   convolving the N spatially transformed images with a temporal kernel to generate a temporal transformation output; and
   applying a nonlinear function to the temporal transformation output to generate the set of retinal response values.

13. The method of claim 1, wherein the encoder is characterized by a set of parameters, and wherein the values of the parameters are determined using response data obtained experimentally from a mammalian retina while said retina is exposed to white noise and natural scene stimuli.

14. The method of claim 13, wherein the encoder is configured such that the Pearson's correlation coefficient between a test input stimulus and a corresponding stimulus reconstructed from the encoded data that would be generated by the encoder in response to the test input stimulus is at least about 0.35.

15. The method of claim 13, wherein the encoder is configured such that the Pearson's correlation coefficient between a test input stimulus and a corresponding stimulus reconstructed from the encoded data that would be generated by the encoder in response to the test input stimulus is at least about 0.65.

16. The method of claim 13, wherein the encoder is configured such that the Pearson's correlation coefficient between a test input stimulus and a corresponding stimulus reconstructed from the encoded data that would be generated by the encoder in response to the test input stimulus is at least about 0.95.

17. The method of claim 13, wherein the test input stimulus comprises a series of natural scenes.

* * * * *